United States Patent
Facchetti et al.

(10) Patent No.: US 10,535,822 B2
(45) Date of Patent: Jan. 14, 2020

(54) MOLECULAR AND POLYMERIC SEMICONDUCTORS AND RELATED DEVICES

(71) Applicant: Flexterra, Inc., Skokie, IL (US)

(72) Inventors: Antonio Facchetti, Chicago, IL (US); Zhihua Chen, Skokie, IL (US); Jennifer E. Brown, St. Louis, MO (US)

(73) Assignee: Flexterra, Inc., Skokie, IL (US)

( * ) Notice: Subject to any disclaimer, the term of this patent is extended or adjusted under 35 U.S.C. 154(b) by 212 days.

(21) Appl. No.: 15/430,535

(22) Filed: Feb. 12, 2017

(65) Prior Publication Data
US 2017/0155053 A1 Jun. 1, 2017

Related U.S. Application Data

(63) Continuation of application No. PCT/US2015/044906, filed on Aug. 12, 2015.
(Continued)

(51) Int. Cl.
*H01L 51/00* (2006.01)
*H01L 51/05* (2006.01)
(Continued)

(52) U.S. Cl.
CPC ........ *H01L 51/0036* (2013.01); *C07D 285/14* (2013.01); *C07D 417/14* (2013.01); *C07D 495/04* (2013.01); *C07F 7/0816* (2013.01); *C08G 61/123* (2013.01); *C08G 61/126* (2013.01); *H01L 51/0043* (2013.01);
(Continued)

(58) Field of Classification Search
None
See application file for complete search history.

(56) References Cited

U.S. PATENT DOCUMENTS

| 3,457,073 A | 7/1969 | Delzenne |
| 2004/0058232 A1 | 3/2004 | Kim |

(Continued)

FOREIGN PATENT DOCUMENTS

| CN | 2014040572 A1 | 3/2014 |
| GB | 1176799 A1 | 1/1970 |

(Continued)

OTHER PUBLICATIONS

M. E. Trusova et al., "A Green Procedure for the Diazotizaton-Iodination of Aromatic Amines under Aqueous, Strong-Acid-Free Conditions," Synthesis, 2011(13), 2154-58 (2011).
(Continued)

*Primary Examiner* — Erik Kielin
(74) *Attorney, Agent, or Firm* — McDonnell Boehnen Hulbert & Berghoff LLP

(57) ABSTRACT

The present invention relates to new semiconducting compounds having at least one optionally substituted benzo[d][1,2,3]thiadiazole moiety. The compounds disclosed herein can exhibit high carrier mobility and/or efficient light absorption/emission characteristics, and can possess certain processing advantages such as solution-processability and/or good stability at ambient conditions.

20 Claims, 8 Drawing Sheets

Related U.S. Application Data

(60) Provisional application No. 62/036,621, filed on Aug. 12, 2014, provisional application No. 62/136,441, filed on Mar. 20, 2015.

(51) Int. Cl.

| | |
|---|---|
| *H01L 51/42* | (2006.01) |
| *C07D 285/14* | (2006.01) |
| *C08G 61/12* | (2006.01) |
| *C07D 417/14* | (2006.01) |
| *C07D 495/04* | (2006.01) |
| *C07F 7/08* | (2006.01) |
| *C08L 65/00* | (2006.01) |
| *C08K 3/04* | (2006.01) |

(52) U.S. Cl.
CPC ... *C08G 2261/12* (2013.01); *C08G 2261/124* (2013.01); *C08G 2261/146* (2013.01); *C08G 2261/149* (2013.01); *C08G 2261/1412* (2013.01); *C08G 2261/1424* (2013.01); *C08G 2261/228* (2013.01); *C08G 2261/3223* (2013.01); *C08G 2261/3243* (2013.01); *C08G 2261/3246* (2013.01); *C08G 2261/414* (2013.01); *C08G 2261/91* (2013.01); *C08G 2261/92* (2013.01); *C08K 3/045* (2017.05); *C08L 65/00* (2013.01); *H01L 51/0047* (2013.01); *H01L 51/0541* (2013.01); *H01L 51/0545* (2013.01); *H01L 51/0558* (2013.01); *H01L 51/4253* (2013.01); *Y02E 10/549* (2013.01)

(56) References Cited

U.S. PATENT DOCUMENTS

| | | |
|---|---|---|
| 2011/0156018 A1* | 6/2011 | Moriwaki ............ B82Y 30/00 257/40 |
| 2013/0026459 A1 | 1/2013 | Yoshimura |
| 2016/0108317 A1* | 4/2016 | Kirsch .................. C09B 57/00 136/252 |

FOREIGN PATENT DOCUMENTS

| | | |
|---|---|---|
| WO | 2010077710 A2 | 7/2010 |
| WO | 2011098113 A2 | 8/2011 |
| WO | 2014040572 A1 | 3/2014 |

OTHER PUBLICATIONS

E.R. Ward & D.D. Heard, "1,2,3-Benzothiadiazole, Part II. Electrophilic Substitution in 4- and 6-Amino-1,2,3-benzothiadiazoles," J. Chem. Soc., 1963, 4794-4803 (1963).

International Preliminary Report on Patentability, International Pat. App. PCT/US2015/044906, dated Feb. 14, 2017.

International Search Report and Written Opinion, International Pat. App. PCT/US2015/044906, dated Nov. 3, 2015.

Z. Chen et al., "Benzo[d][1,2,3]thiadiazole (isoBT): Synthesis, Structural Analysis, and Implementation in Semiconducting Polymers," Chem. Mater., 28, 6390-6400 (2016).

\* cited by examiner

MOLECULAR AND POLYMERIC SEMICONDUCTORS AND RELATED DEVICES

CROSS-REFERENCE TO RELATED APPLICATIONS

This application is a continuation of International Application No. PCT/US2015/044906, filed on Aug. 12, 2015, which claims priority to and the benefit of the filing dates of U.S. Provisional Patent Application Ser. No. 62/036,621 filed on Aug. 12, 2014, and U.S. Provisional Patent Application Ser. No. 62/136,441 filed on Mar. 20, 2015, the entire disclosure of each of which is hereby expressly incorporated by reference herein for all uses and purposes.

BACKGROUND

Flexible and printed electronics is a revolutionary new concept for fabricating optoelectronic devices using high-throughput, inexpensive solution processes (e.g., printing methodologies) on flexible plastic foils, which contrasts sharply with the highly specialized and expensive facilities and equipment required for silicon fabrication. By using the appropriate materials, these technologies could enable inexpensive, lightweight, flexible, optically transparent, and unbreakable components for displays, cell phones, medical diagnostics, RFID tags, and solar modules which can then be integrated with textiles, printed batteries, solar cells, and aircraft and satellite structures. The enabling material component of all these technologies (among other essential materials) is the semiconductor where charge transport, light absorption, and/or light generation occur. To broaden device functionalities and applications, two types of semiconductors are required: p-type (hole-transporting) and n-type (electron-transporting). The use and combination of these two types of semiconductors enables the fabrication of elementary electronic building blocks for driving displays, harvesting light, generating light, carrying out logic operations, and sensor functions.

Several p- and n-channel molecular semiconductors have achieved acceptable device performance and stability. For example, OTFTs based on acenes and oligothiophenes (p-channel) and perylenes (n-channel) exhibit carrier mobilities ($\mu$'s)>1 cm$^2$/Vs in ambient conditions. However, molecular semiconductors typically are less easily processable via printing methodologies than polymeric semiconductors due to solution viscosity requirements.

Accordingly, the art desires new semiconducting compounds, particularly those having good stability, processing properties, and/or charge transport characteristics in ambient conditions.

SUMMARY

In light of the foregoing, the present teachings provide organic semiconducting compounds that can address various deficiencies and shortcomings of the prior art, including those outlined above. Compounds according to the present teachings can exhibit properties such as optimized optical absorption, good charge transport characteristics and chemical stability in ambient conditions, low-temperature processability, large solubility in common solvents, and processing versatility (e.g., via various solution processes). As a result, optoelectronic devices such as OPV cells that incorporate one or more of the present compounds as a photoactive layer can exhibit high performance in ambient conditions, for example, demonstrating one or more of low band-gap, high fill factor, high open circuit voltage, and high power conversion efficiency, and preferably all of these criteria. Similarly, other organic semiconductor-based devices such as OTFTs can be fabricated efficiently using the organic semiconductor materials described herein.

Generally, the present teachings provide semiconducting compounds that include one or more divalent benzo[d][1,2,3]thiadiazole moieties. Such divalent benzo[d][1,2,3]thiadiazole moieties can be represented by formula (I):

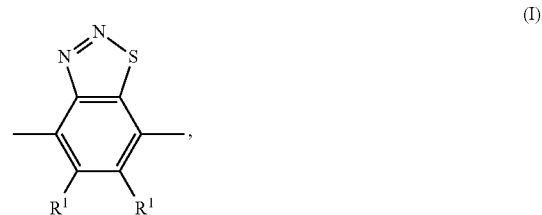

(I)

wherein $R^1$ can be H or a substituent. In some embodiments, the present compound is a polymer having one or more repeating units $M_1$ each of which includes at least one benzo[d][1,2,3]thiadiazole moiety, and where the polymer has a degree of polymerization (n) ranging from at least 3. In certain embodiments, the polymer is a homopolymer including only repeating units $M_1$. In other embodiments, the polymer also includes at least one other repeating unit $M_2$ that does not include any benzo[d][1,2,3]thiadiazole moiety. Such $M_2$ unit can be selected from:

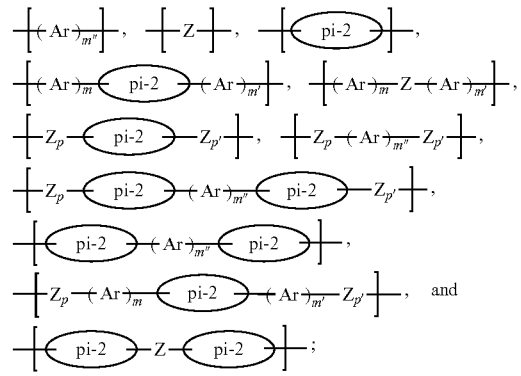

wherein pi-2, Ar, Z, m, m', m", p, and p' are as defined herein. In some embodiments, the present compound is a molecular compound including at least one benzo[d][1,2,3]thiadiazole moiety and a plurality of linear and/or cyclic conjugated moieties, such that the compound as a whole provides a pi-extended conjugated system.

The present teachings also provide methods of preparing such compounds and semiconductor materials based on such compounds, as well as various compositions, composites, and devices that incorporate the compounds and semiconductor materials disclosed herein.

The foregoing as well as other features and advantages of the present teachings will be more fully understood from the following figures, description, examples, and claims.

BRIEF DESCRIPTION OF DRAWINGS

It should be understood that the drawings described below are for illustration purpose only. The drawings are not necessarily to scale, with emphasis generally being placed upon illustrating the principles of the present teachings. The drawings are not intended to limit the scope of the present teachings in any way.

DETAILED DESCRIPTION

Figure 1:
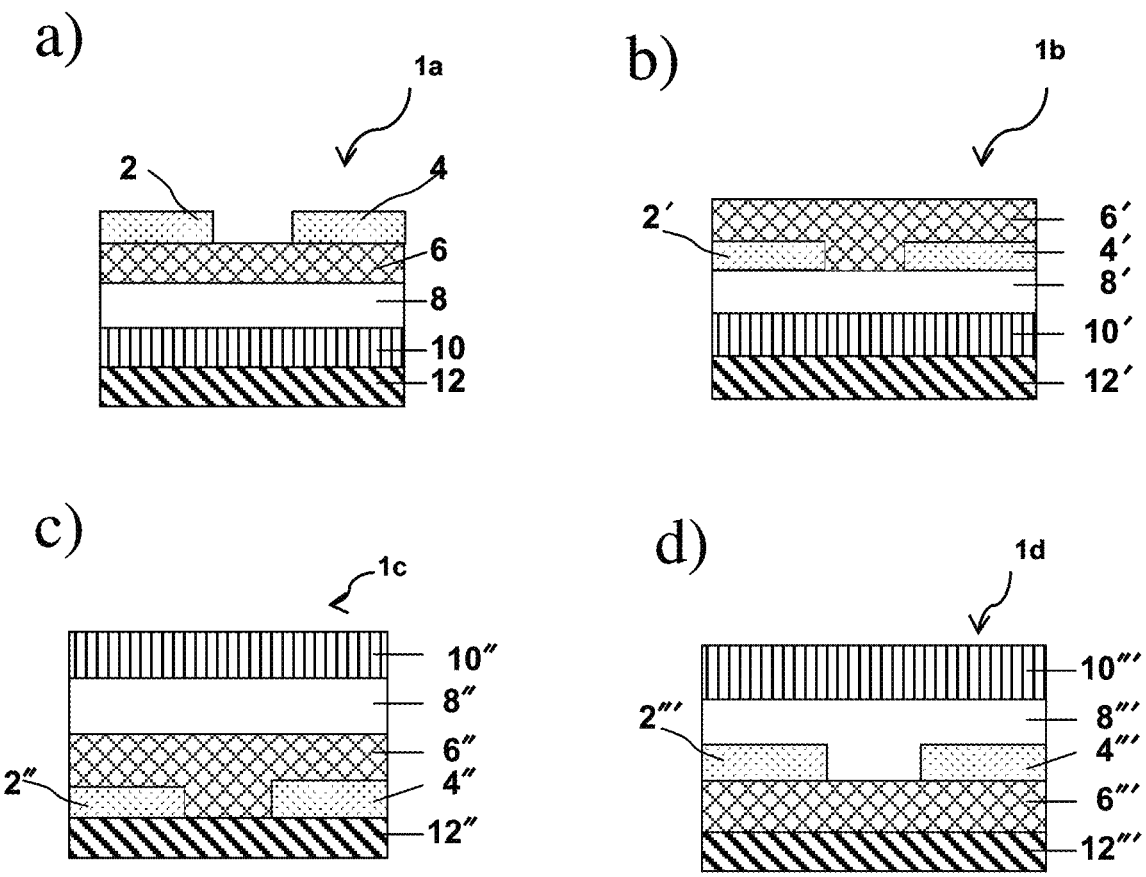
FIG. 1 illustrates four different configurations of thin film transistors: a) bottom-gate top contact, b) bottom-gate bottom-contact, c) top-gate bottom-contact, and d) top-gate top-contact; each of which can be used to incorporate one or more compounds of the present teachings, particularly as the channel (semiconductor) materials.

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, a "p-type semiconductor material" or a "donor" material refers to a semiconductor material, for example, an organic semiconductor material, having holes as the majority current or charge carriers. In some embodiments, when a p-type semiconductor material is deposited on a substrate, it can provide a hole mobility in excess of about $10^{-5}$ $cm^2/Vs$. In the case of field-effect devices, a p-type semiconductor also can exhibit a current on/off ratio of greater than about 10.

As used herein, an "n-type semiconductor material" or an "acceptor" material refers to a semiconductor material, for example, an organic semiconductor material, having electrons as the majority current or charge carriers. In some embodiments, when an n-type semiconductor material is deposited on a substrate, it can provide an electron mobility in excess of about $10^{-5}$ $cm^2/Vs$. In the case of field-effect devices, an n-type semiconductor also can exhibit a current on/off ratio of greater than about 10.

As used herein, "mobility" refers to a measure of the velocity with which charge carriers, for example, holes (or units of positive charge) in the case of a p-type semiconductor material and electrons (or units of negative charge) in the case of an n-type semiconductor material, move through the material under the influence of an electric field. This parameter, which depends on the device architecture, can be measured using a field-effect device or space-charge limited current measurements.

As used herein, a compound can be considered "ambient stable" or "stable at ambient conditions" when a transistor incorporating the compound as its semiconducting material exhibits a carrier mobility that is maintained at about its initial measurement when the compound is exposed to ambient conditions, for example, air, ambient temperature, and humidity, over a period of time. For example, a compound can be described as ambient stable if a transistor incorporating the compound shows a carrier mobility that does not vary more than 20% or more than 10% from its initial value after exposure to ambient conditions, including, air, humidity and temperature, over a 3 day, 5 day, or 10 day period.

As used herein, fill factor (FF) is the ratio (given as a percentage) of the actual maximum obtainable power, ($P_m$ or $V_{mp}*J_{mp}$), to the theoretical (not actually obtainable) power, ($J_{sc}*V_{oc}$). Accordingly, FF can be determined using the equation:

$$FF=(V_{mp}*J_{mp})/(J_{sc}*V_{oc})$$

where $J_{mp}$ and $V_{mp}$ represent the current density and voltage at the maximum power point (PA respectively, this point being obtained by varying the resistance in the circuit until $J*V$ is at its greatest value; and $J_{sc}$ and $V_{oc}$ represent the short circuit current and the open circuit voltage, respectively. Fill factor is a key parameter in evaluating the performance of solar cells. Commercial solar cells typically have a fill factor of about 0.60% or greater.

As used herein, the open-circuit voltage ($V_{oc}$) is the difference in the electrical potentials between the anode and the cathode of a device when there is no external load connected.

As used herein, the power conversion efficiency (PCE) of a solar cell is the percentage of power converted from incident light to electrical power. The PCE of a solar cell can be calculated by dividing the maximum power point ($P_m$) by the input light irradiance (E, in $W/m^2$) under standard test conditions (STC) and the surface area of the solar cell ($A_c$ in $m^2$). STC typically refers to a temperature of 25° C. and an irradiance of 1000 $W/m^2$ with an air mass 1.5 (AM 1.5) spectrum.

As used herein, a component (such as a thin film layer) can be considered "photoactive" if it contains one or more compounds that can absorb photons to produce excitons for the generation of a photocurrent.

As used herein, "solution-processable" refers to compounds (e.g., polymers), materials, or compositions that can be used in various solution-phase processes including spin-coating, printing (e.g., inkjet printing, gravure printing, offset printing and the like), spray coating, electrospray coating, drop casting, dip coating, and blade coating.

As used herein, a "polymeric compound" (or "polymer") refers to a molecule including a plurality of one or more repeating units connected by covalent chemical bonds. A polymeric compound can be represented by the general formula:

wherein M is the repeating unit or monomer. The polymeric compound can have only one type of repeating unit as well as two or more types of different repeating units. When a polymeric compound has only one type of repeating unit, it can be referred to as a homopolymer. When a polymeric compound has two or more types of different repeating units, the term "copolymer" or "copolymeric compound" can be used instead. For example, a copolymeric compound can include repeating units

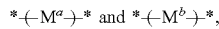

where $M^a$ and $M^b$ represent two different repeating units. Unless specified otherwise, the assembly of the repeating units in the copolymer can be head-to-tail, head-to-head, or tail-to-tail. In addition, unless specified otherwise, the copolymer can be a random copolymer, an alternating copolymer, or a block copolymer. For example, the general formula:

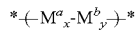

can be used to represent a copolymer of $M^a$ and $M^b$ having x mole fraction of $M^a$ and y mole fraction of $M^b$ in the copolymer, where the manner in which comonomers $M^a$ and $M^b$ is repeated can be alternating, random, regiorandom, regioregular, or in blocks. In addition to its composition, a polymeric compound can be further characterized by its degree of polymerization (n) and molar mass (e.g., number average molecular weight ($M_n$) and/or weight average molecular weight ($M_w$) depending on the measuring technique(s)).

As used herein, "heteroatom" refers to an atom of any element other than carbon or hydrogen and includes, for example, nitrogen, oxygen, silicon, sulfur, phosphorus, and selenium.

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as described herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula $-C_zH_{2z+1-t}X^0_t$, where $X^0$, at each occurrence, is F, Cl, Br or I, z is an integer in the range of 1 to 40, and t is an integer in the range of 1 to 81, provided that t is less than or equal to 2z+1. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxyl, hexoxyl groups, and the like. The alkyl group in the —O-alkyl group can be substituted as described herein.

As used herein, "alkylthio" refers to an —S-alkyl group. Examples of alkylthio groups include, but are not limited to, methylthio, ethylthio, propylthio (e.g., n-propylthio and isopropylthio), t-butylthio, pentylthio, hexylthio groups, and the like. The alkyl group in the —S-alkyl group can be substituted as described herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$ alkenyl group), for example, 2 to 20 carbon atoms (i.e., $C_{2-20}$ alkenyl group). In some embodiments, alkenyl groups can be substituted as described herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include ethynyl, propynyl, butynyl, pentynyl, hexynyl, and the like. The one or more triple carbon-carbon bonds can be internal (such as in 2-butyne) or terminal (such as in 1-butyne). In various embodiments, an alkynyl group can have 2 to 40 carbon atoms (i.e., $C_{2-40}$ alkynyl group), for example, 2 to 20 carbon atoms (i.e., $C_{2-20}$ alkynyl group). In some embodiments, alkynyl groups can be substituted as described herein. An alkynyl group is generally not substituted with another alkynyl group, an alkyl group, or an alkenyl group.

As used herein, a "cyclic moiety" can include one or more (e.g., 1-6) carbocyclic or heterocyclic rings. In embodiments where the cyclic moiety is a "polycyclic moiety," the "polycyclic moiety" can include two or more rings fused to each other (i.e., sharing a common bond) and/or connected to each other via a spiro atom. The cyclic moiety can be a cycloalkyl group, a heterocycloalkyl group, an aryl group, or a heteroaryl group (i.e., can include only saturated bonds, or can include one or more unsaturated bonds regardless of aromaticity), and can be optionally substituted as described herein. In embodiments where the cyclic moiety is a "monocyclic moiety," the "monocyclic moiety" can include a 3-20 membered carbocyclic or heterocyclic ring. A monocyclic moiety can include a $C_{6-20}$ aryl group (e.g., $C_{6-14}$ aryl group) or a 5-20 membered heteroaryl group (e.g., 5-14 membered heteroaryl group), each of which can be optionally substituted as described herein.

As used herein, "cycloalkyl" refers to a non-aromatic carbocyclic group including cyclized alkyl, alkenyl, and alkynyl groups. In various embodiments, a cycloalkyl group can have 3 to 20 carbon atoms, for example, 3 to 14 carbon atoms (i.e., $C_{3-14}$ cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as described herein.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 20 ring atoms, for example, 3 to 14 ring atoms (i.e., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 22 carbon atoms in its ring system (e.g., $C_{6-14}$ aryl group), which can include multiple fused rings. In some embodiments, a polycyclic aryl group can have from 8 to 22 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic) and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "arylalkyl" refers to an -alkyl-aryl group, where the arylalkyl group is covalently linked to the defined chemical structure via the alkyl group. An arylalkyl group is within the definition of a —Y—$C_{6-14}$ aryl group, where Y is as defined herein. An example of an arylalkyl group is a benzyl group (—$CH_2$—$C_6H_5$). An arylalkyl group can be optionally substituted, i.e., the aryl group and/or the alkyl group, can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group, as a whole, can have, for example, 5 to 22 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

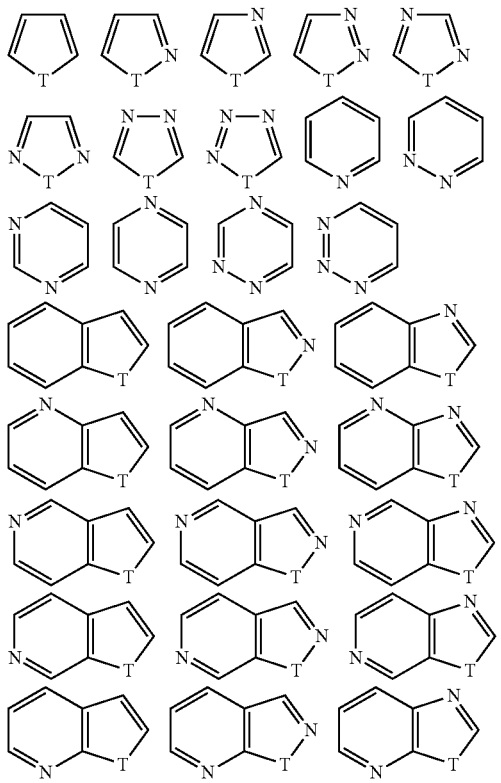

where T is O, S, NH, N-alkyl, N-aryl, N-(arylalkyl) (e.g., N-benzyl), SiH$_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

Compounds of the present teachings can include a "divalent group" defined herein as a linking group capable of forming a covalent bond with two other moieties. For example, compounds of the present teachings can include a divalent $C_{1-20}$ alkyl group (e.g., a methylene group), a divalent $C_{2-20}$ alkenyl group (e.g., a vinylyl group), a divalent $C_{2-20}$ alkynyl group (e.g., an ethynylyl group), a divalent $C_{6-14}$ aryl group (e.g., a phenylyl group); a divalent 3-14 membered cycloheteroalkyl group (e.g., a pyrrolidylyl), and/or a divalent 5-14 membered heteroaryl group (e.g., a thienylyl group).

The electron-donating or electron-withdrawing properties of several hundred of the most common substituents, reflecting all common classes of substituents have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein.

It should be understood that the term "electron-accepting group" can be used synonymously herein with "electron acceptor" and "electron-withdrawing group". In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogen or halo (e.g., F, Cl, Br, I), —NO$_2$, —CN, —NC, —S(R$^o$)$_2^+$, —N(R$^o$)$_3^+$, —SO$_3$H, —SO$_2$R$^o$, —SO$_3$R$^o$, —SO$_2$NHR$^o$, —SO$_2$N(R$^o$)$_2$, —COOH, —COR$^o$, —COOR$^o$, —CONHR$^o$, —CON(R$^o$)$_2$, $C_{1-40}$ haloalkyl groups, $C_{6-14}$ aryl groups, and 5-14 membered electron-poor heteroaryl groups; where R$^o$ is a $C_{1-20}$ alkyl group, a $C_{2-20}$ alkenyl group, a $C_{2-20}$ alkynyl group, a $C_{1-20}$ haloalkyl group, a $C_{1-20}$ alkoxy group, a $C_{6-14}$ aryl group, a $C_{3-14}$ cycloalkyl group, a 3-14 membered cycloheteroalkyl group, and a 5-14 membered heteroaryl group, each of which can be optionally substituted as described herein. For example, each of the $C_{1-20}$ alkyl group, the $C_{2-20}$ alkenyl group, the $C_{2-20}$ alkynyl group, the $C_{1-20}$ haloalkyl group, the $C_{1-20}$ alkoxy group, the $C_{6-14}$ aryl group, the $C_{3-14}$ cycloalkyl group, the 3-14 membered cycloheteroalkyl group, and the 5-14 membered heteroaryl group can be optionally substituted with 1-5 small electron-withdrawing groups such as F, Cl, Br, —NO$_2$, —CN, —NC, —S(R$^o$)$_2^+$, —N(R$^o$)$_3^+$, —SO$_3$H, —SO$_2$R$^o$, —SO$_3$R$^o$, —SO$_2$NHR$^o$, —SO$_2$N(R$^o$)$_2$, —COOH, —COR$^o$, —COOR$^o$, —CONHR$^o$, and —CON(R$^o$)$_2$.

It should be understood that the term "electron-donating group" can be used synonymously herein with "electron donor". In particular, an "electron-donating group" or an "electron-donor" refers to a functional group that donates electrons to a neighboring atom more than a hydrogen atom would if it occupied the same position in a molecule. Examples of electron-donating groups include —OH, —OR$^o$, —NH$_2$, —NHR$^o$, —N(R$^o$)$_2$, and 5-14 membered electron-rich heteroaryl groups, where R$^o$ is a $C_{1-20}$ alkyl group, a $C_{2-20}$ alkenyl group, a $C_{2-20}$ alkynyl group, a $C_{6-14}$ aryl group, or a $C_{3-14}$ cycloalkyl group.

Various unsubstituted heteroaryl groups can be described as electron-rich (or π-excessive) or electron-poor (or π-deficient). Such classification is based on the average electron density on each ring atom as compared to that of a carbon atom in benzene. Examples of electron-rich systems include 5-membered heteroaryl groups having one heteroatom such as furan, pyrrole, and thiophene; and their benzofused counterparts such as benzofuran, benzopyrrole, and benzothiophene. Examples of electron-poor systems include 6-membered heteroaryl groups having one or more heteroatoms such as pyridine, pyrazine, pyridazine, and pyrimidine; as well as their benzofused counterparts such as quinoline, isoquinoline, quinoxaline, cinnoline, phthalazine, naphthyridine, quinazoline, phenanthridine, acridine, and purine. Mixed heteroaromatic rings can belong to either class depending on the type, number, and position of the one or more heteroatom(s) in the ring. See Katritzky, A. R and Lagowski, J. M., *Heterocyclic Chemistry* (John Wiley & Sons, New York, 1960).

At various places in the present specification, substituents of monomers A and B are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes, azo, and imines). It also should be understood that compounds of the present teachings encompass all possible regioisomers in pure form and mixtures thereof. It may be possible to separate such isomers, for example, using standard separation procedures known to those skilled in the art, for example, column chromatography, thin-layer chromatography, simulated moving-bed chromatography, and high-performance liquid chromatography. However, mixtures of regioisomers can be used similarly to the uses of each individual regioisomer of the present teachings.

It is specifically contemplated that the depiction of one regioisomer includes any other regioisomers and any regioisomeric mixtures unless specifically stated otherwise.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halogen (e.g., Cl, Br, I), azide ($N_3$), thiocyanate (SCN), nitro ($NO_2$), cyanate (CN), water ($H_2O$), ammonia ($NH_3$), and sulfonate groups (e.g., $OSO_2$—R, wherein R can be a $C_{1-10}$ alkyl group or a $C_{6-14}$ aryl group each optionally substituted with 1-4 groups independently selected from a $C_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

Throughout the specification, structures may or may not be presented with chemical names. Where any question arises as to nomenclature, the structure prevails.

The present teachings relate to molecular and polymeric compounds that can be used as organic semiconductor materials. The present compounds can have good solubility in various common organic solvents and good stability in air. When incorporated into optical, electronic or optoelectronic devices including, but not limited to, organic photovoltaic or solar cells, organic light emitting diodes, and organic field effect transistors, the present compounds can confer various desirable performance properties.

More specifically, the present teachings provide semiconducting compounds that include one or more optionally substituted benzo[d][1,2,3]thiadiazole moieties. The optionally substituted benzo[d][1,2,3]thiadiazole moieties can be represented by formula (I):

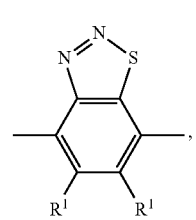

(I)

wherein:

$R^1$, at each occurrence, independently can be selected from H, halogen, —CN, $NO_2$, $R^2$, -L-$R^3$, OH, $OR^2$, $OR^3$, $NH_2$, $NHR^2$, $N(R^2)_2$, $NR^2R^3$, $N(R^3)_2$, SH, $SR^2$, $SR^3$, $S(O)_2OH$, —$S(O)_2OR^2$, —$S(O)_2OR^3$, C(O)H, C(O)$R^2$, C(O)$R^3$, C(O)OH, C(O)$OR^2$, C(O)$OR^3$, C(O)$NH_2$, C(O)$NHR^2$, C(O)N($R^2$)$_2$, C(O)N$R^2R^3$, C(O)N($R^3$)$_2$, $SiH_3$, $SiH(R^2)_2$, $SiH_2(R^2)$, and $Si(R^2)_3$, wherein L is selected from a divalent $C_{1-40}$ alkyl group, a divalent $C_{2-40}$ alkenyl group, a divalent $C_{1-40}$ haloalkyl group, and a covalent bond; $R^2$ is selected from a $C_{1-40}$ alkyl group, a $C_{2-40}$ alkenyl group, a $C_{2-40}$ alkynyl group, and a $C_{1-40}$ haloalkyl group; and $R^3$ is selected from a $C_{3-10}$ cycloalkyl group, a $C_{6-14}$ aryl group, a $C_{6-14}$ haloaryl group, a 3-12 membered cycloheteroalkyl group, and a 5-14 membered heteroaryl group, each of which optionally is substituted with 1-5 substituents selected from halogen, —CN, $NO_2$, $R^2$, $OR^2$, and $SR^2$.

In preferred embodiments, each $R^1$ independently can be selected from H, F, Cl, Br, I, —CN, —$NO_2$, $R^2$, $OR^2$, and $SR^2$, where $R^2$ can be selected from a linear or branched $C_{1-10}$ alkyl group, a linear or branched $C_{2-10}$ alkenyl group, and a linear or branched $C_{1-10}$ haloalkyl group. In certain embodiments, both $R^1$ are H. In particular embodiments, $R^1$ can be selected from H, F, Cl, Br, I, —CN, —NO$_2$, CH$_3$, OCH$_3$, CF$_3$, and a phenyl group, where at least one of R$^1$ is not H.

In some embodiments, the present compound is a polymer having one or more repeating units M$_1$, where each M$_1$ includes at least one optionally substituted benzo[d][1,2,3]thiadiazole moiety represented by formula (I), and where the polymer has a degree of polymerization (n) ranging from at least 3.

Other than benzo[d][1,2,3]thiadiazole moieties, repeating units M$_1$ optionally can include one or more spacers (Sp) which can be either non-cyclic (Z) or cyclic, particularly monocyclic (Ar) or polycyclic (pi-2), which together with the benzo[d][1,2,3]thiadiazole moieties provide a pi-extended conjugated group. For example, M$_1$ can be selected from:

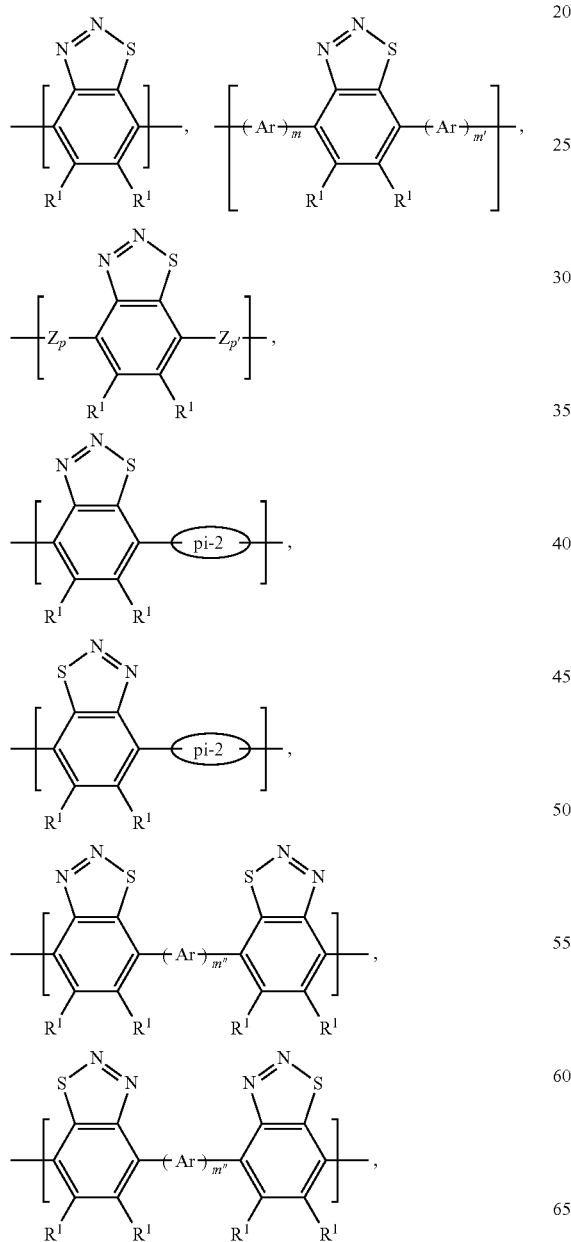

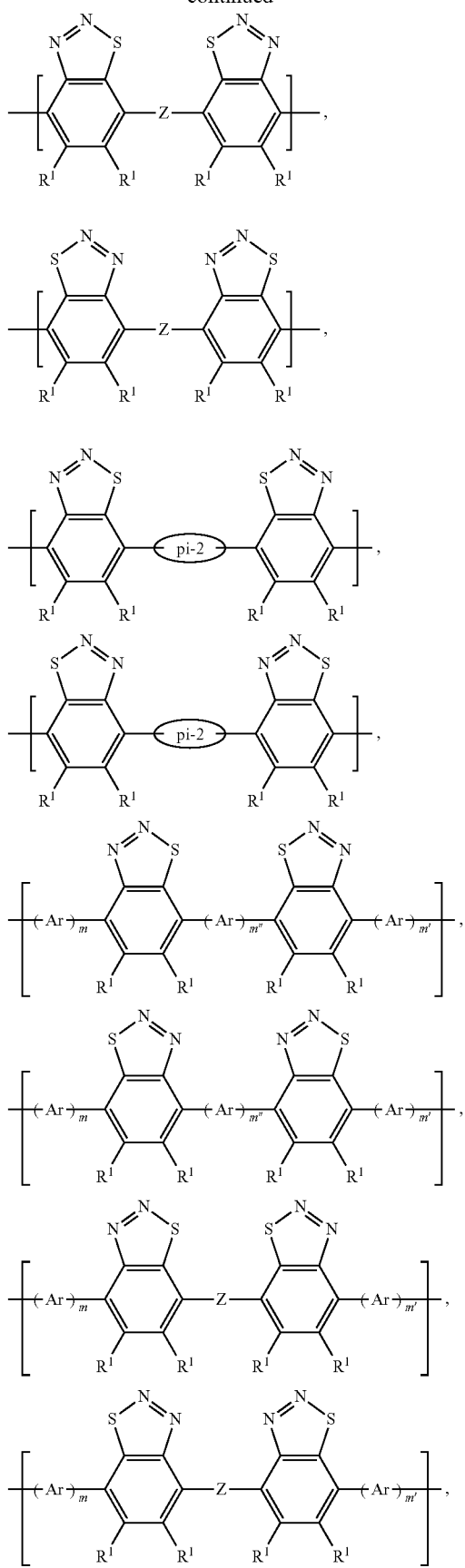

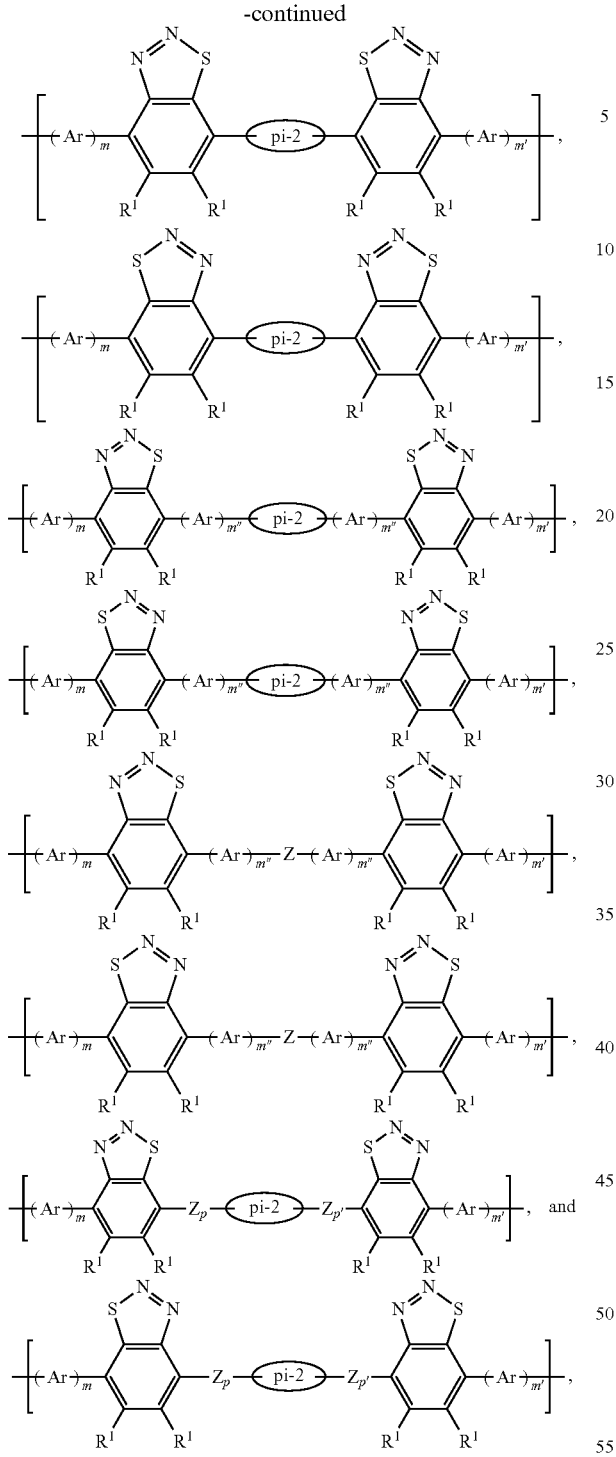

wherein:
pi-2 is an optionally substituted conjugated polycyclic moiety;
Ar, at each occurrence, is independently an optionally substituted 5- or 6-membered aryl or heteroaryl group;
Z is a conjugated noncyclic linker;
m and m' independently are 0, 1, 2, 3, 4, 5 or 6, provided that at least one of m and m' is not 0;
m" is 1, 2, 3, 4, 5 or 6; and
p and p' independently are 0 and 1, provided that at least one of p and p' is 1.

To illustrate, the polycyclic conjugated moiety, pi-2, can be an optionally substituted $C_{8-26}$ aryl group or 8-26 membered heteroaryl group. For example, pi-2 can have a planar and pi-extended conjugated cyclic core which can be optionally substituted as disclosed herein. Examples of suitable cyclic cores include naphthalene, anthracene, tetracene, pentacene, perylene, pyrene, coronene, fluorene, indacene, indenofluorene, and tetraphenylene, as well as their analogs in which one or more carbon atoms can be replaced with a heteroatom such as O, S, Si, Se, N, or P.

In certain embodiments, pi-2 can be selected from:

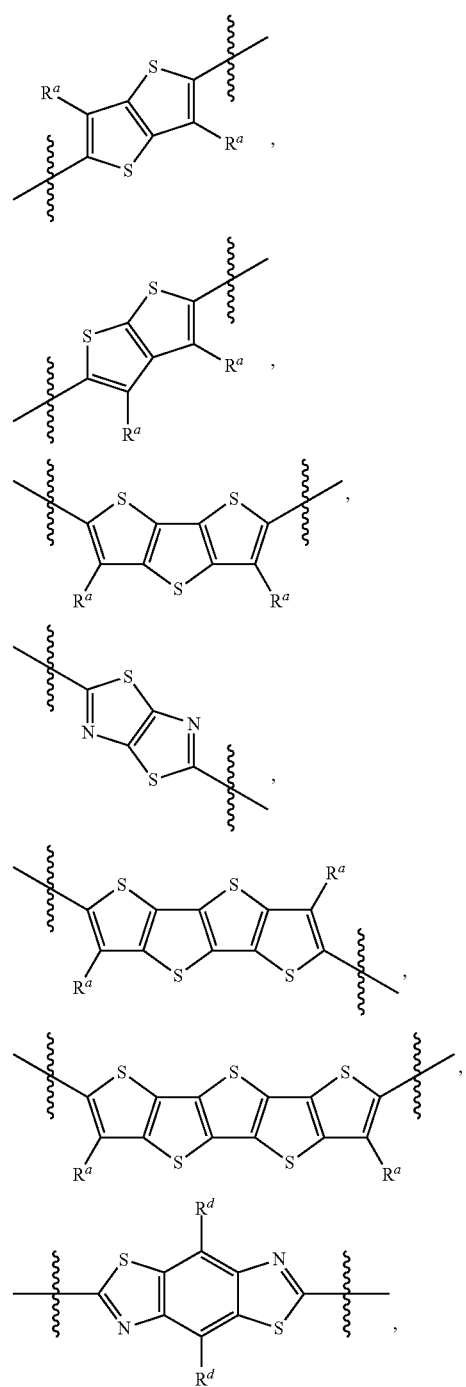

-continued
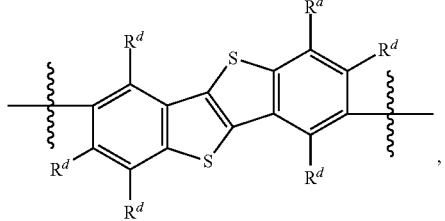,
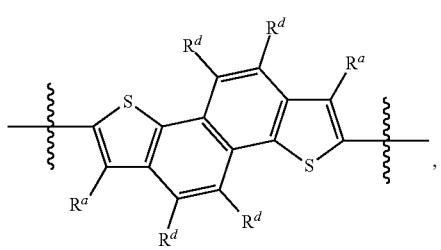,
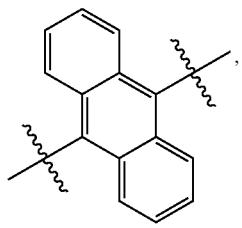,
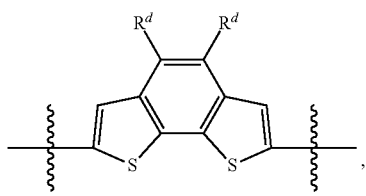,
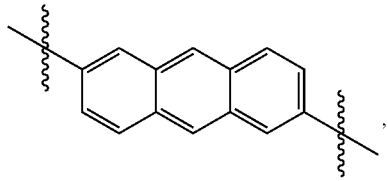,
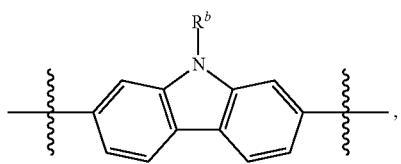,
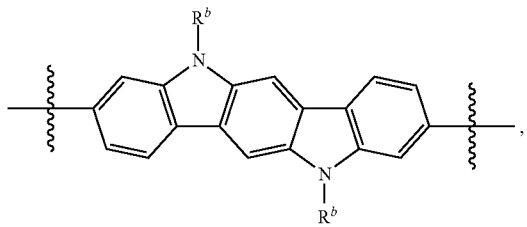,
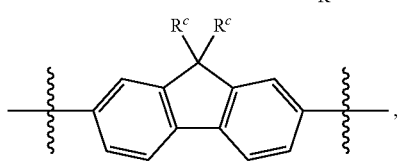,
-continued
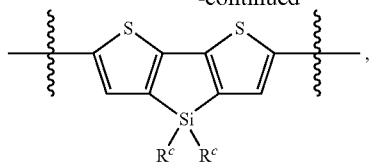,
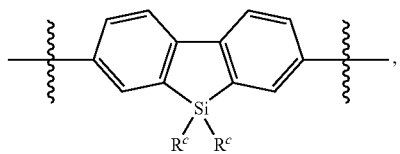,
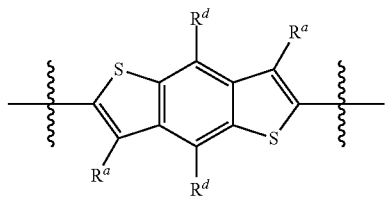,
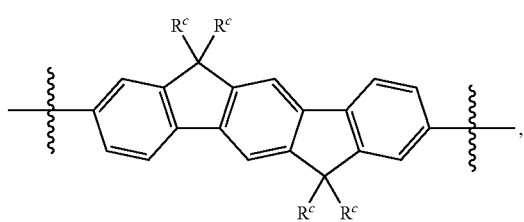,
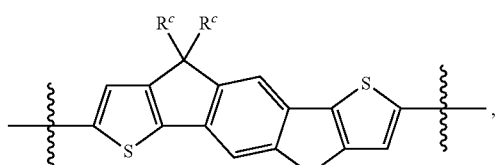,
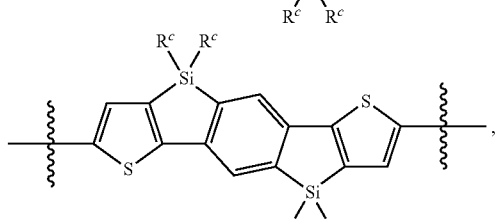,
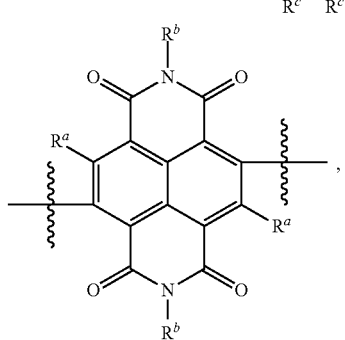,

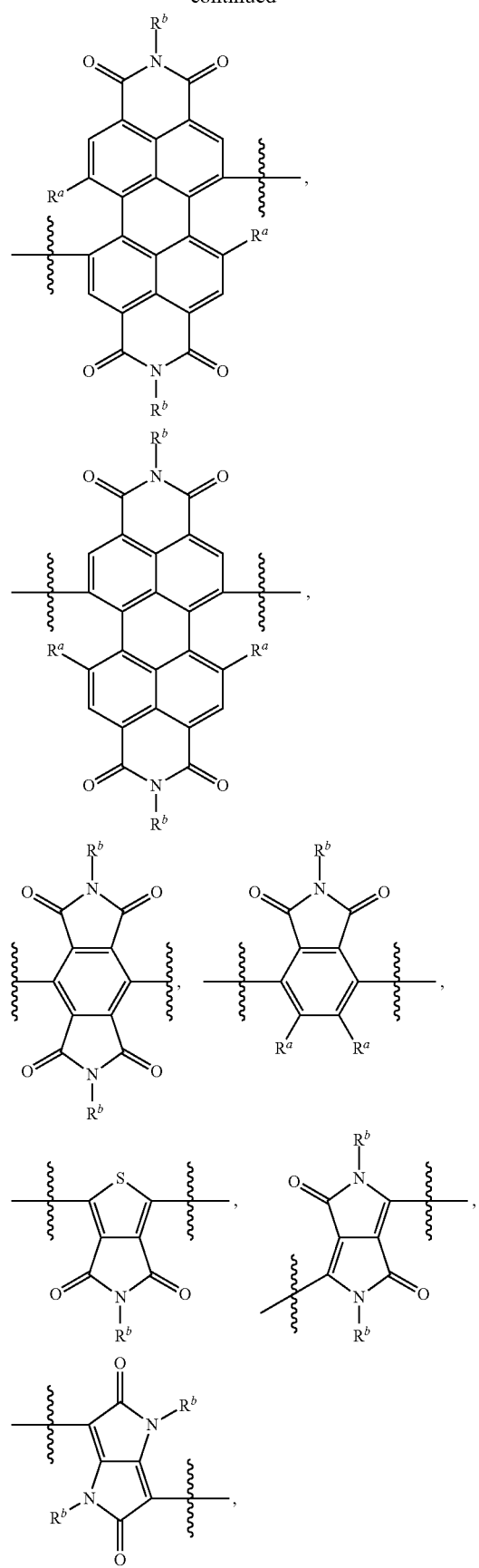
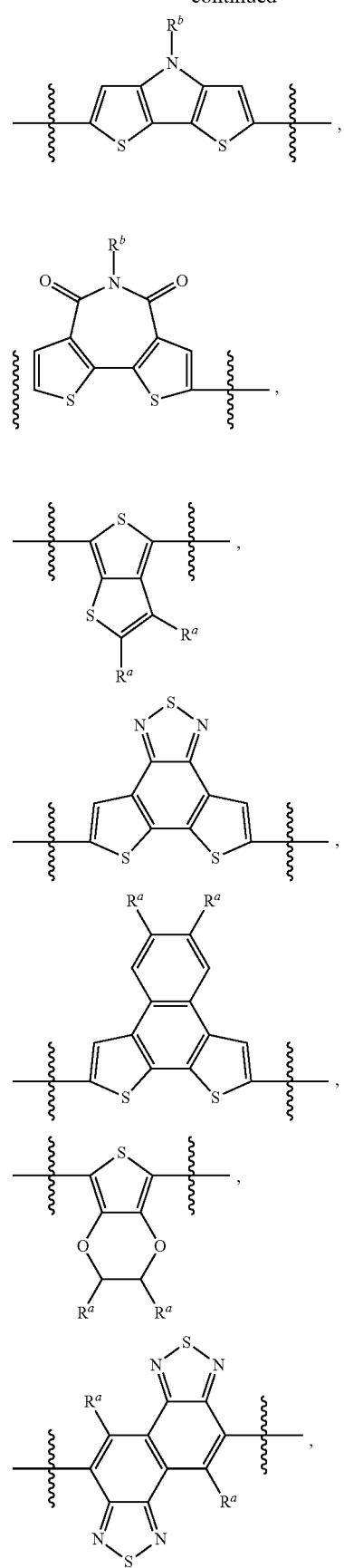

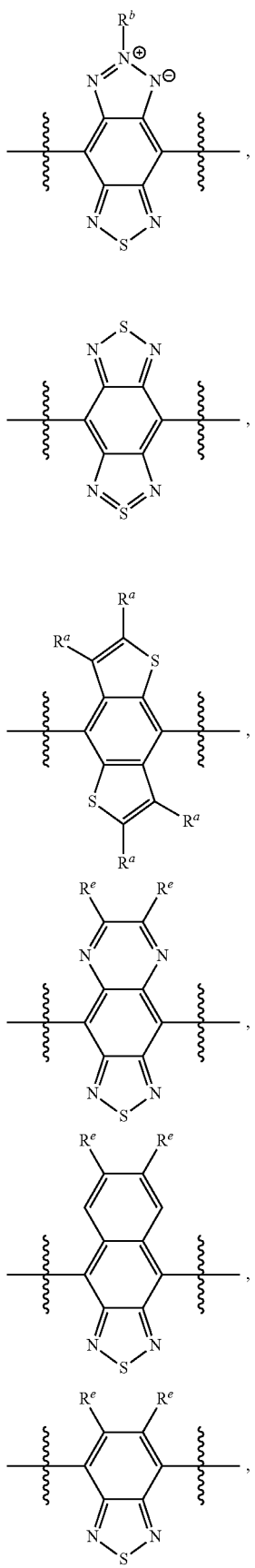

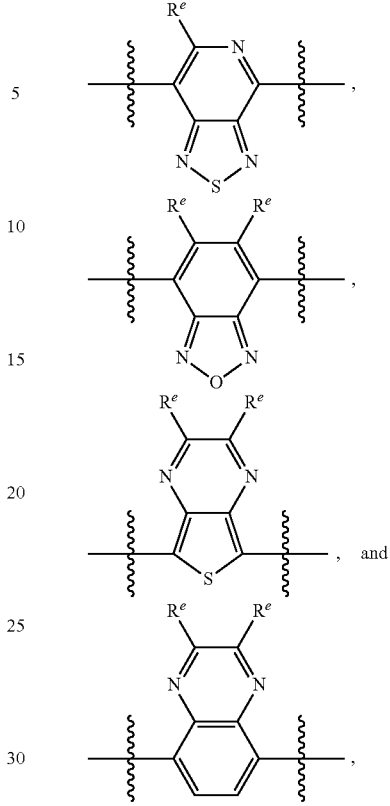

wherein:
R$^a$ is selected from the group consisting of H, F, Cl, —CN, R, —OR, —SR, —C(O)R, —OC(O)R, and —C(O)OR;
R$^b$ is selected from the group consisting of H, R, and -L-R$^f$;
R$^c$ is H or R;
R$^d$ is selected from the group consisting of H, F, Cl, —CN, R, —OR, —SR, —C(O)R, —OC(O)R, —C(O)OR, and -L-R$^f$;
R$^e$ is selected from the group consisting of H, F, Cl, —CN, R, —OR, —SR, —C(O)R, —OC(O)R, —C(O)OR, and R$^f$;
R$^f$ is a C$_{6-20}$ aryl group or a 5-20-membered heteroaryl group, each optionally substituted with 1-8 groups independently selected from the group consisting of F, Cl, —CN, R, —OR, and —SR;
L is selected from the group consisting of —O—, —S—, —C(O)—, —OC(O)—, —C(O)O—, and a covalent bond; and
R is selected from the group consisting of a C$_{1-40}$ alkyl group, a C$_{1-40}$ haloalkyl group, a C$_{2-40}$ alkenyl group, and a C$_{2-40}$ alkynyl group.

The monocyclic conjugated moiety, Ar, at each occurrence, independently can be an optionally substituted 5- or 6-membered (hetero)aryl group. For example, Ar can be selected from the group consisting of a phenyl group, a thienyl group, a thiazolyl group, an isothiazolyl group, a thiadiazolyl group, a furyl group, an oxazolyl group, an isoxazolyl group, an oxadiazolyl group, a pyrrolyl group, a triazolyl group, a tetrazolyl group, a pyrazolyl group, an imidazolyl group, a pyridyl group, a pyrimidyl group, a pyridazinyl group, and a pyrazinyl group, each of which optionally can be substituted with 1-4 R$^5$ groups independently selected from a halogen, CN, a C$_{1-40}$ alkyl group, a C$_{1-40}$ haloalkyl group, a C$_{1-40}$ alkoxy group, and a C$_{1-40}$ alkylthio group.

By way of example, each Ar in $(Ar)_m$, $(Ar)_{m'}$, and/or $(Ar)_{m''}$ that is present (i.e., when m, m', and/or m" is 1, 2, 3, 4, 5 or 6) can be represented by:

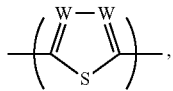

where each W independently can be selected from N, CH, and $CR^4$, wherein $R^4$ can be selected from F, Cl, —CN, $R^2$, $OR^2$, $SR^2$, $C(O)R^2$, $OC(O)R^2$, and $C(O)OR^2$, where $R^2$ is as defined herein. To illustrate further, $(Ar)_m$, $(Ar)_{m'}$, or $(Ar)_{m''}$ when present can be selected from:

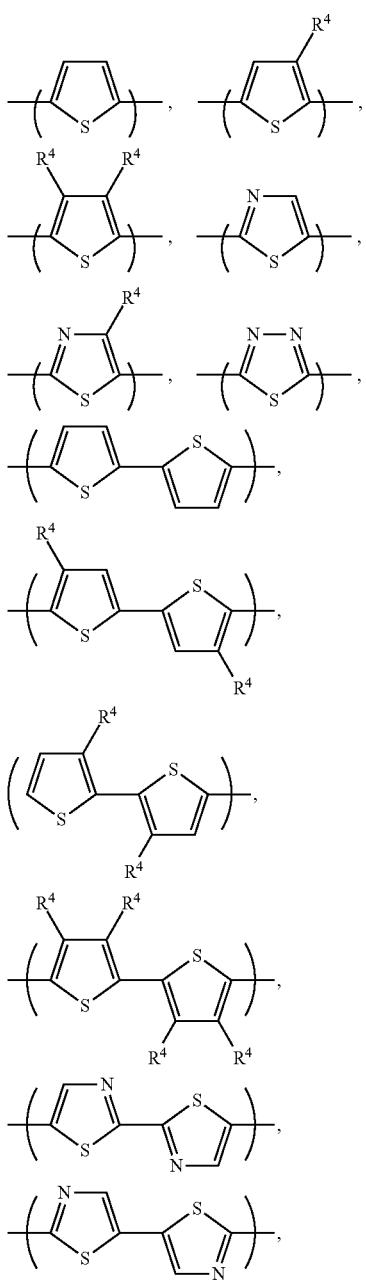

-continued

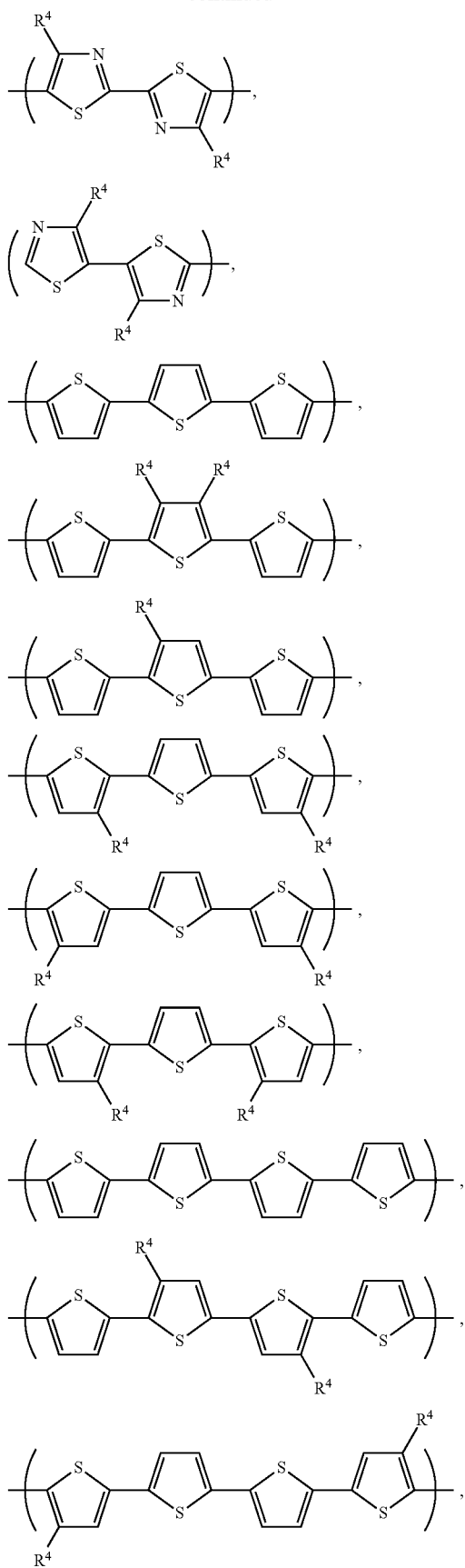

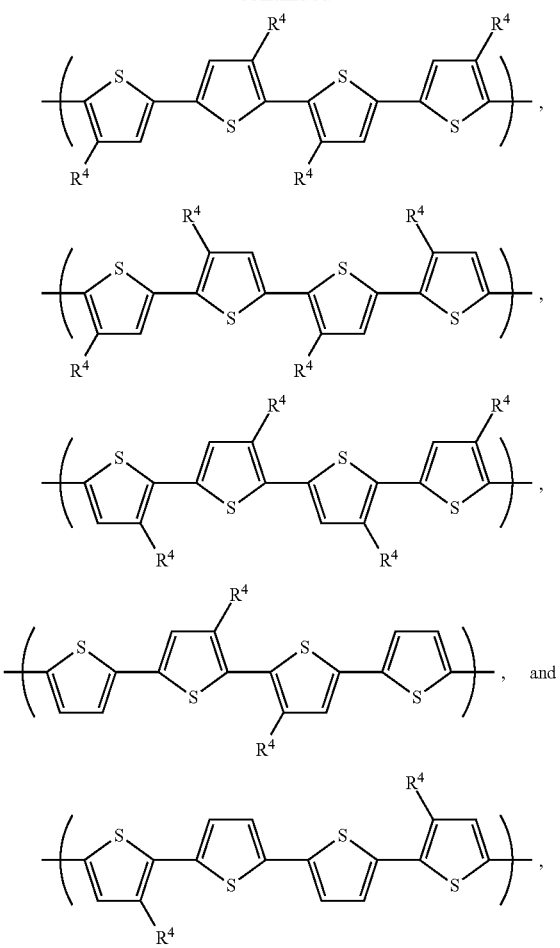

where, for example, each R⁴ independently is selected from F, Cl, CN, $R^2$, $OR^2$, and $SR^2$, where $R^2$ is a linear or branched $C_{1-40}$ alkyl or haloalkyl group.

The conjugated noncyclic linker, Z, can include one or more double or triple bonds. For example, Z can be a divalent ethenyl group (i.e., having one double bond), a divalent ethynyl group (i.e., having one tripe bond), a $C_{4-40}$ alkenyl or alkynyl group that includes two or more conjugated double or triple bonds, or some other linear or branched conjugated systems that can include heteroatoms such as Si, N, P, and the like. In certain embodiments, Z can be selected from:

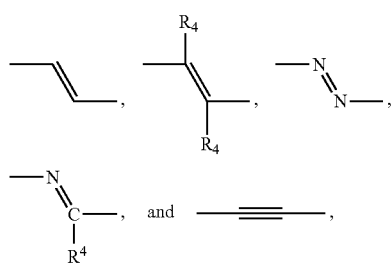

wherein R⁴ is as defined herein. In particular embodiments, Z can be selected from:

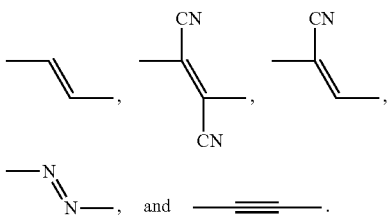

In preferred embodiments, the present polymer includes a repeating unit $M_1$ selected from the group consisting of:

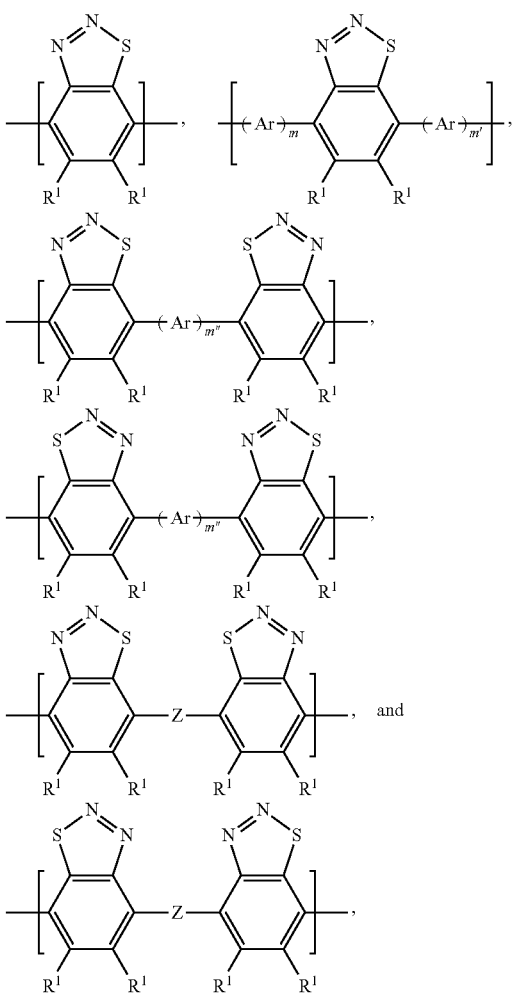

where Ar, Z, m, m', and m" are as defined herein.

More preferably, $M_1$ is selected from:

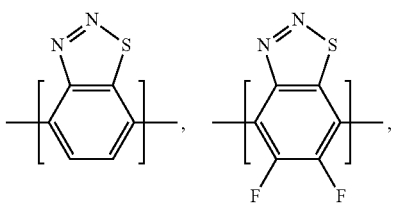

-continued

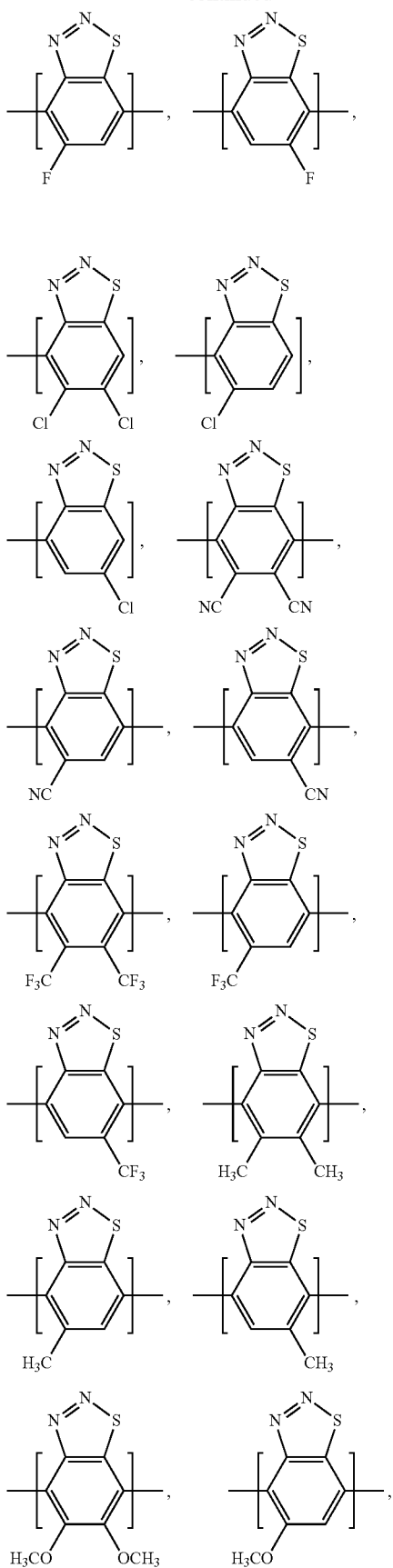

-continued

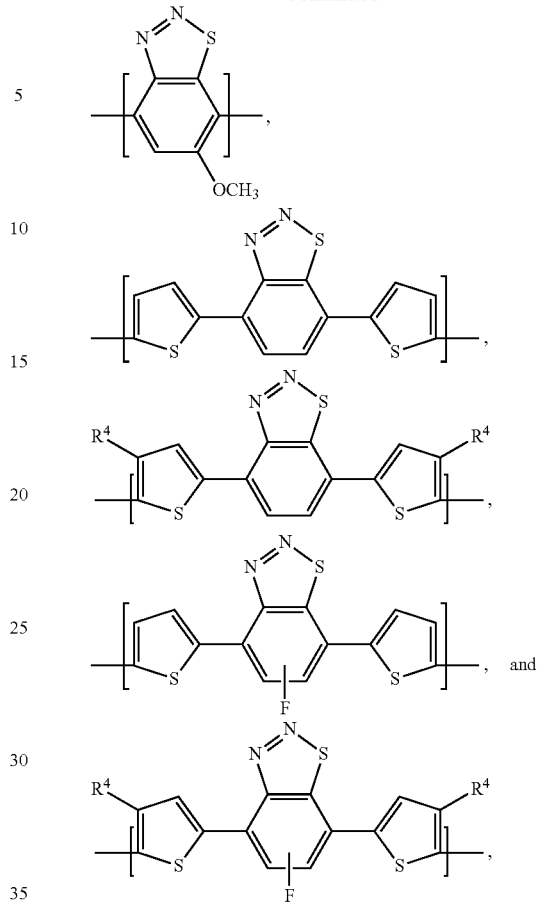

wherein $R^4$ can be selected from $R^2$, $OR^2$, and $SR^2$, where $R^2$ is a linear or branched $C_{1-40}$ alkyl or haloalkyl group.

In certain embodiments, the present polymer can be a homopolymer including only identical repeating units $M_1$. In other embodiments, the polymer can be a copolymer including two or more different repeating units $M_1$. In yet other embodiments, the polymer can be a copolymer including at least one repeating unit $M_1$ and at least one other repeating unit $M_2$ that does not include any benzo[d][1,2,3]thiadiazole moiety. Such $M_2$ units can include one or more non-cyclic (Z), monocyclic (Ar), and/or polycyclic (pi-2) conjugated linkers, which together provide a pi-extended conjugated group. For example, $M_2$ can be selected from:

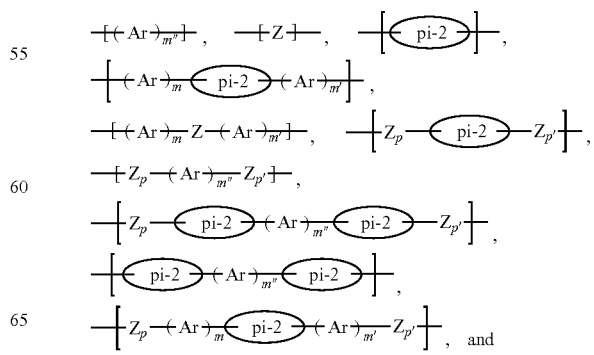

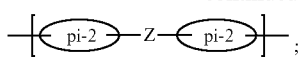
wherein pi-2, Ar, Z, m, m', m", p, and p' are as defined herein.
To illustrate, in certain embodiments, $M_2$ can have the formula:
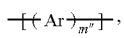
wherein m" is selected from 1, 2, 3, or 4; and Ar is as defined herein. For example, $M_2$ can be selected from the group consisting of:
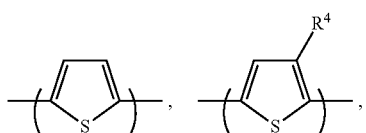
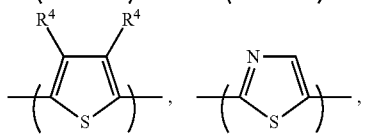
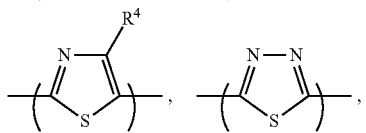
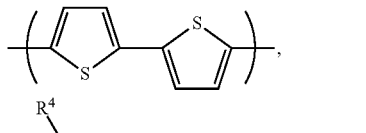
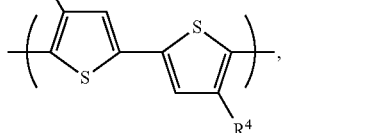
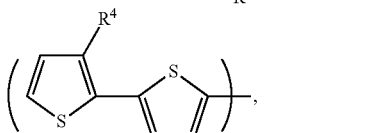
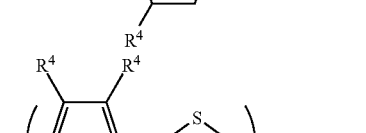
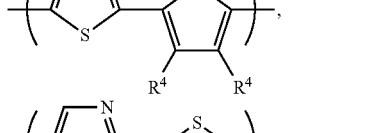
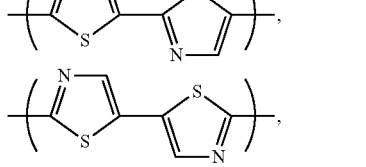
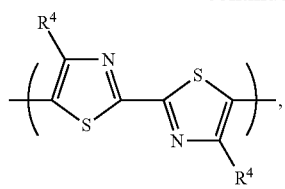
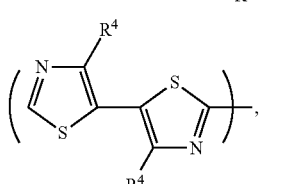
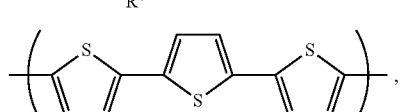
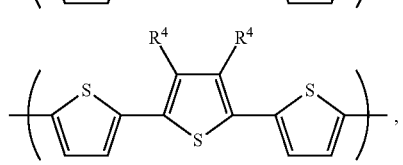
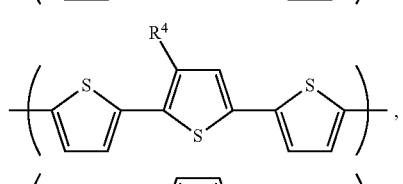
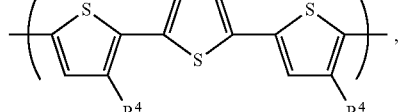
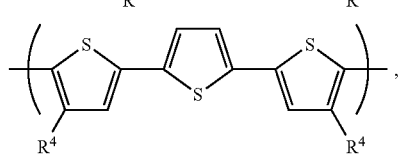
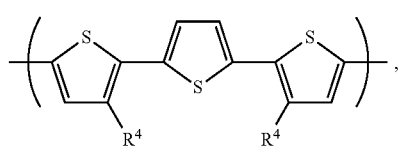
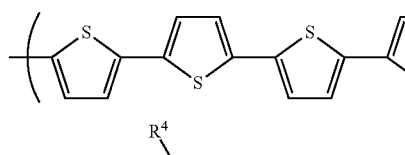
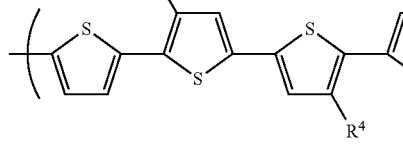
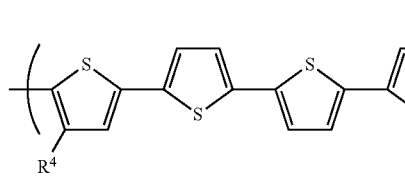

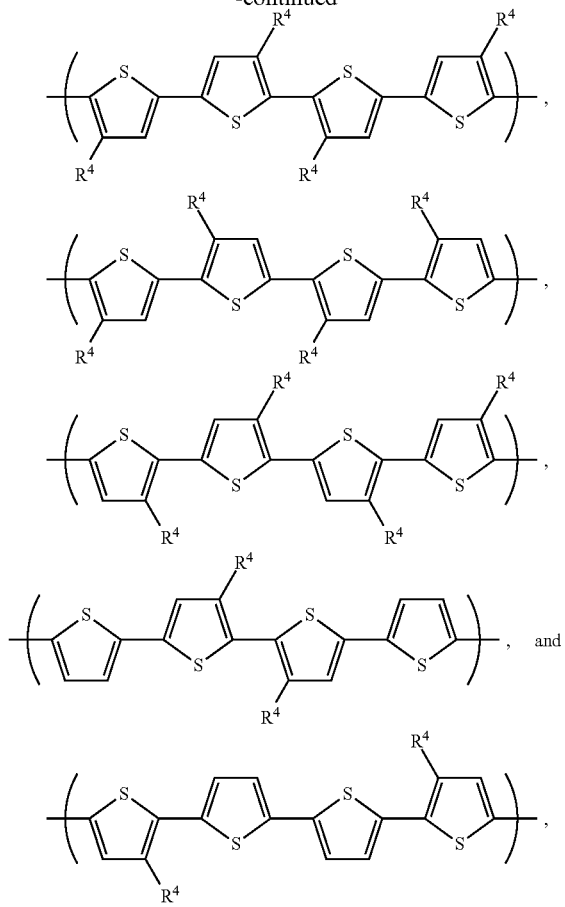
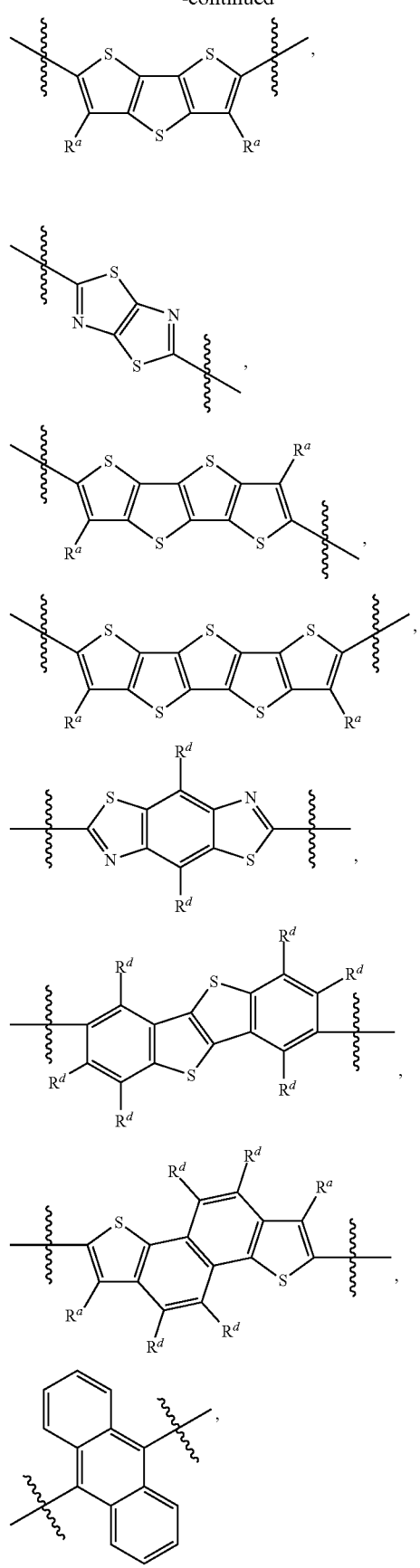
where, for example, each $R^4$ independently is selected from F, Cl, CN, $R^2$, $OR^2$, and $SR^2$, where $R^2$ is a linear or branched $C_{1-40}$ alkyl or haloalkyl group.
In other embodiments, $M_2$ can have the formula:
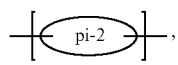
wherein pi-2 can be selected from:
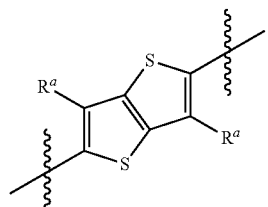
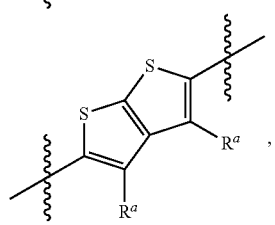
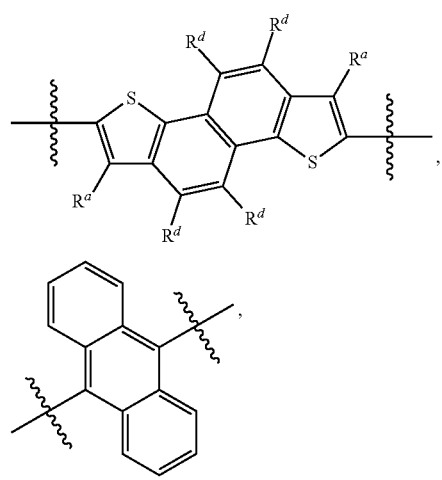
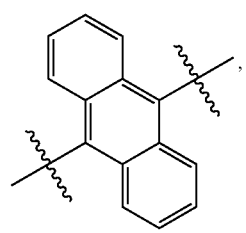

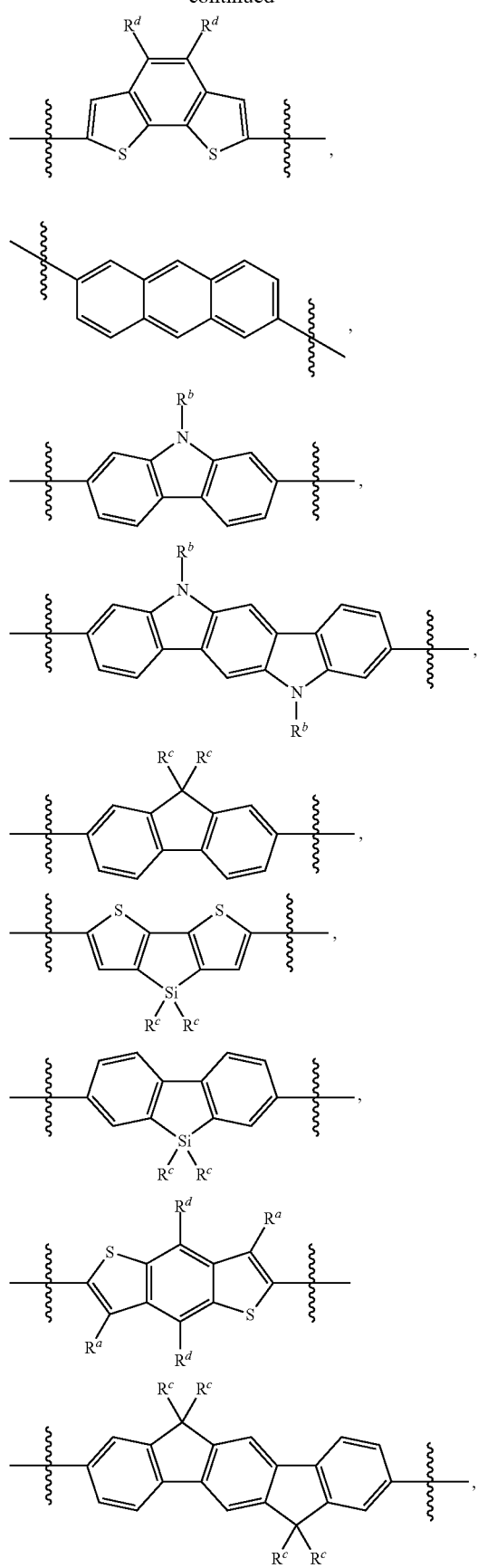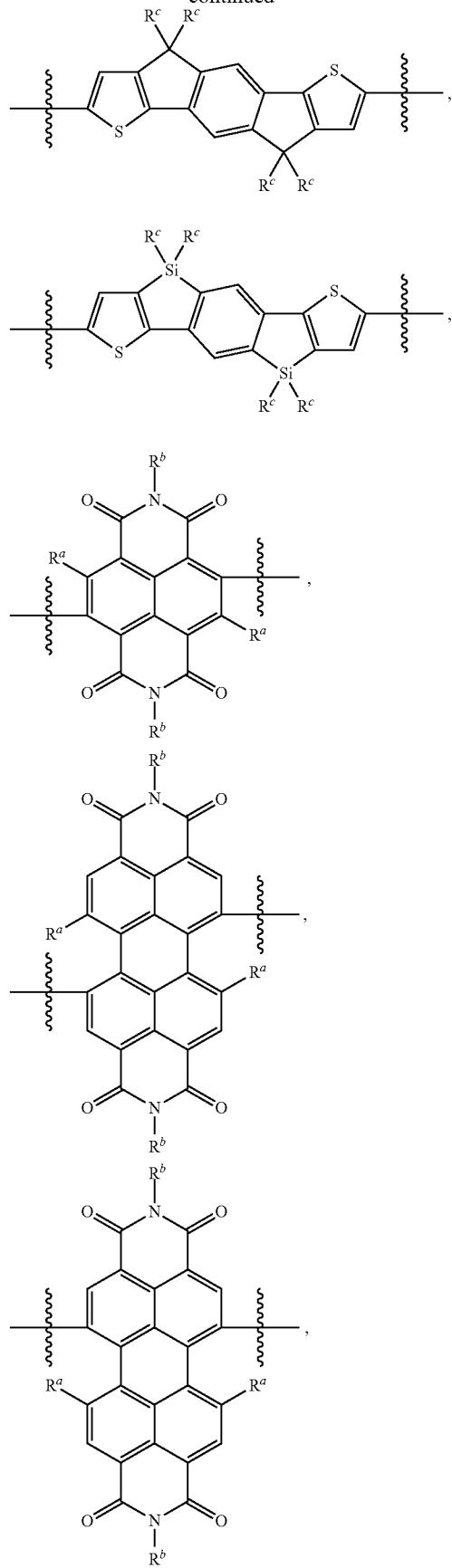

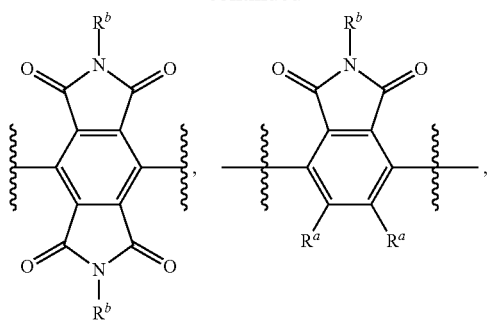
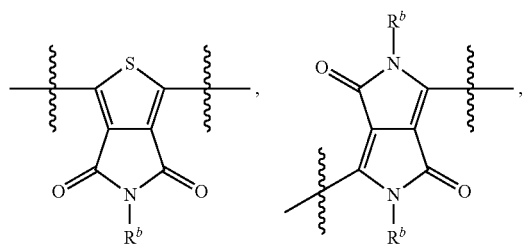
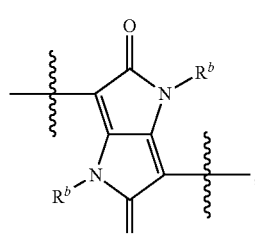
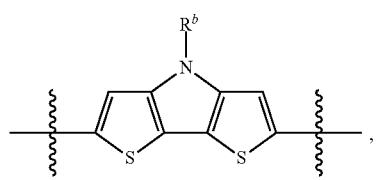
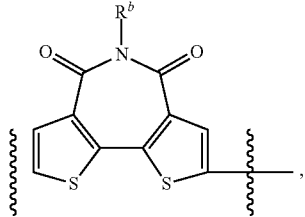
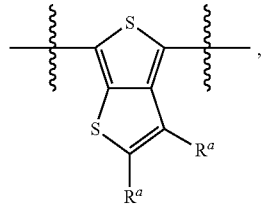
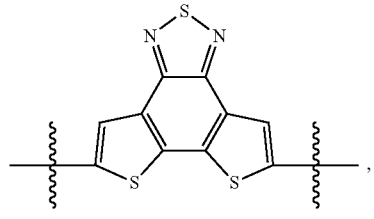
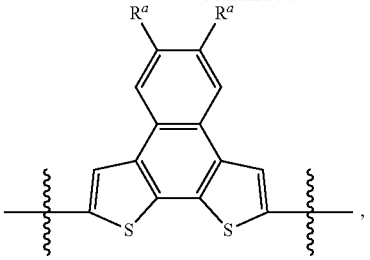
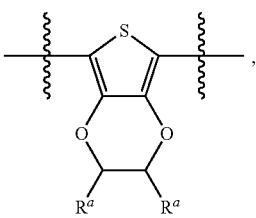
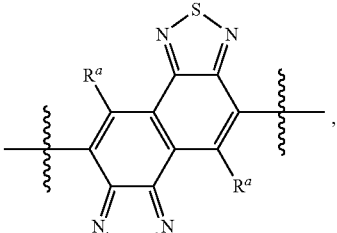
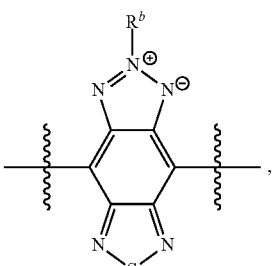
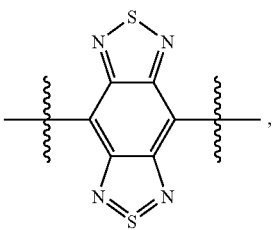
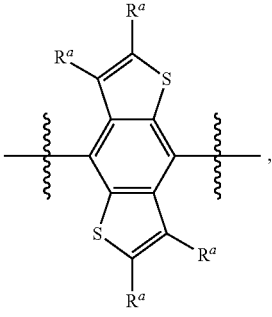

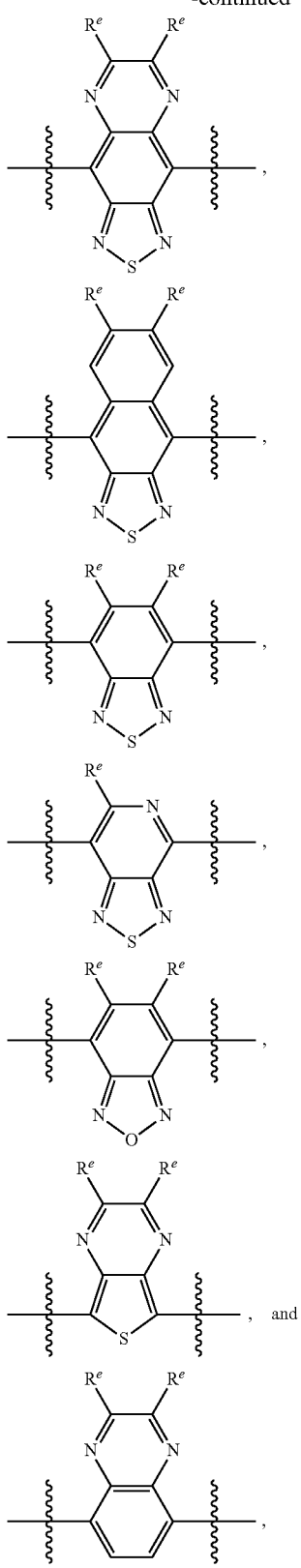, and wherein:
$R^a$ is selected from the group consisting of H, F, Cl, —CN, R, —OR, —SR, —C(O)R, —OC(O)R, and —C(O)OR;
$R^b$ is selected from the group consisting of H, R, and -L-$R^f$;
$R^c$ is H or R;
$R^d$ is selected from the group consisting of H, F, Cl, —CN, R, —OR, —SR, —C(O)R, —OC(O)R, —C(O)OR, and -L-$R^f$;
$R^e$ is selected from the group consisting of H, F, Cl, —CN, R, —OR, —SR, —C(O)R, —OC(O)R, —C(O)OR, and $R^f$;
$R^f$ is a $C_{6-20}$ aryl group or a 5-20-membered heteroaryl group, each optionally substituted with 1-8 groups independently selected from the group consisting of F, Cl, —CN, R, —OR, and —SR;
L is selected from the group consisting of —O—, —S—, —C(O)—, —OC(O)—, —C(O)O—, and a covalent bond; and
R is selected from the group consisting of a $C_{1-40}$ alkyl group, a $C_{1-40}$ haloalkyl group, a $C_{2-40}$ alkenyl group, and a $C_{2-40}$ alkynyl group.

In yet other embodiments, $M_2$ can have the formula:

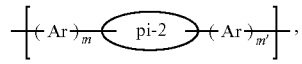

wherein Ar, pi-2, m and m' are as defined herein. Preferably, $(Ar)_m$ and $(Ar)_{m'}$ are selected from:

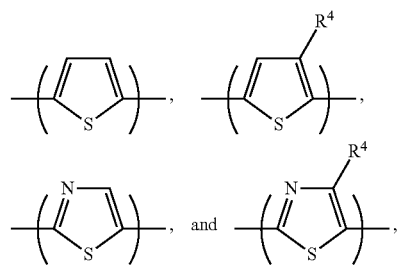

where $R^4$ is as defined herein, and pi-2 is selected from:

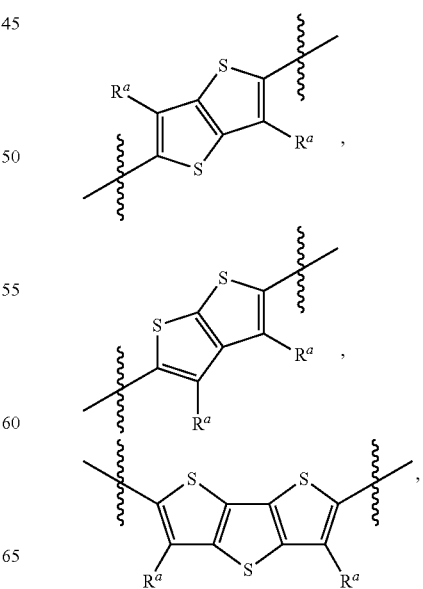

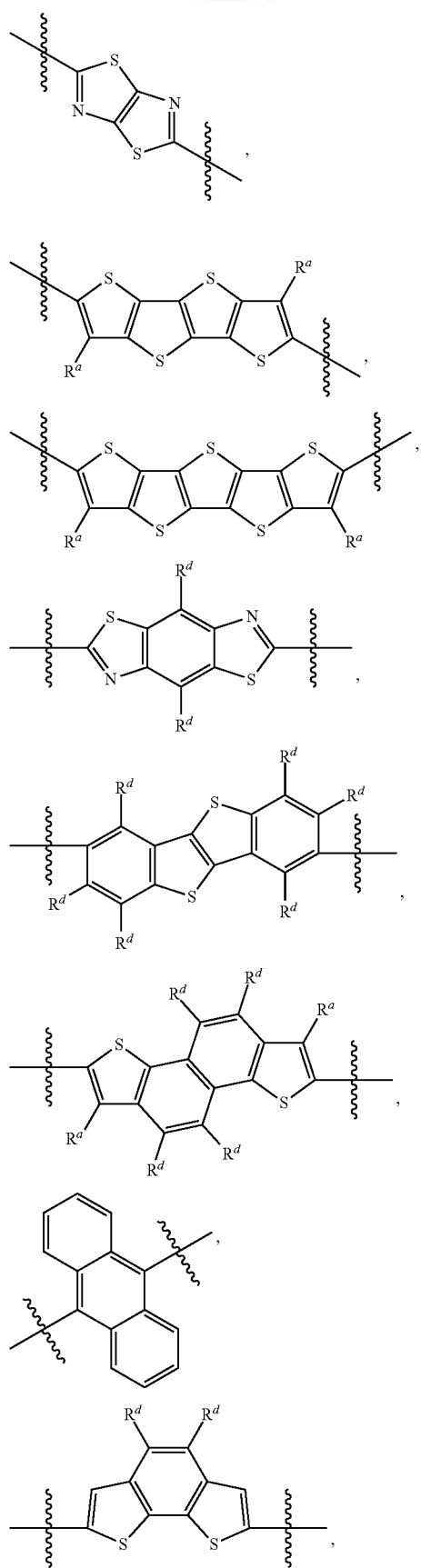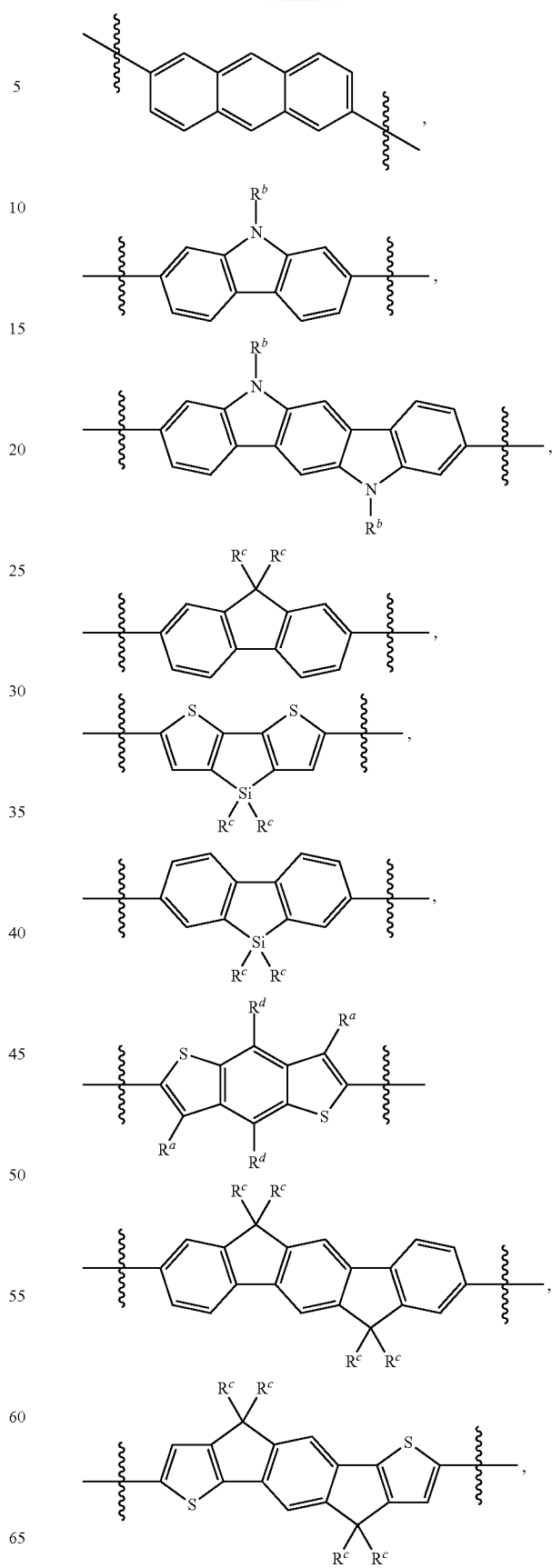

-continued
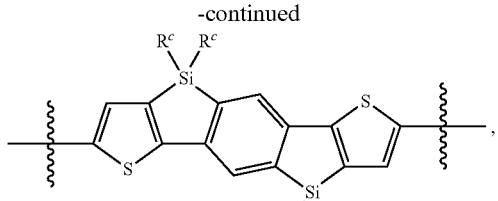
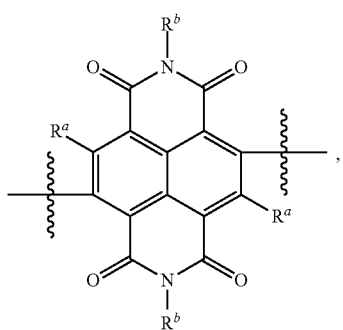
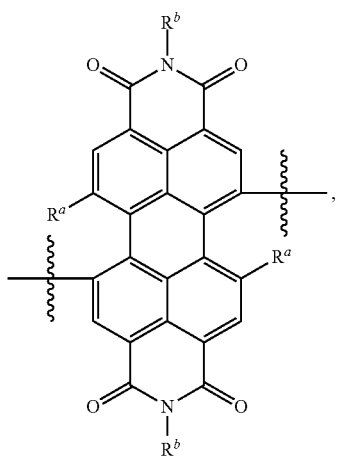
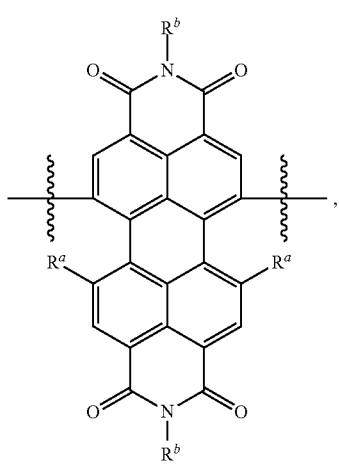
-continued
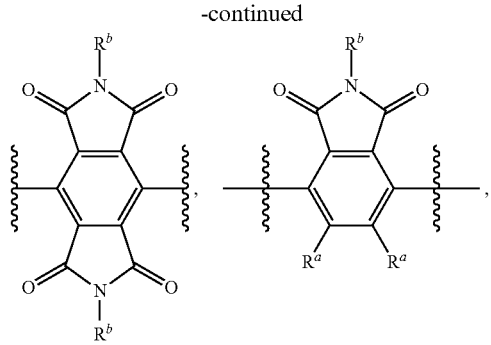
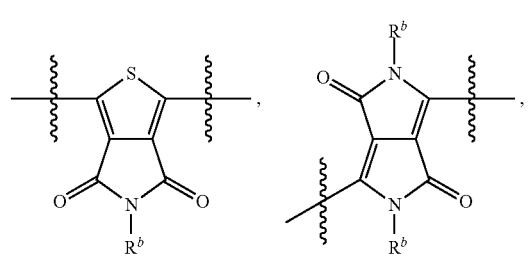
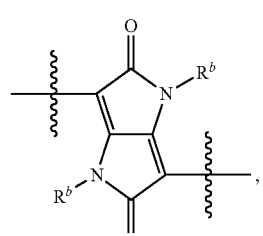
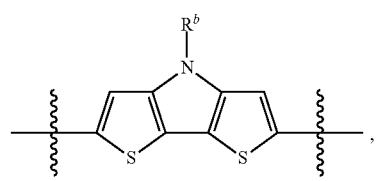
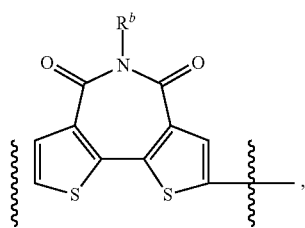
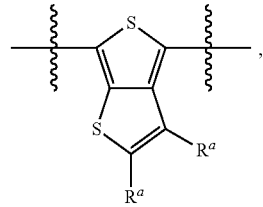
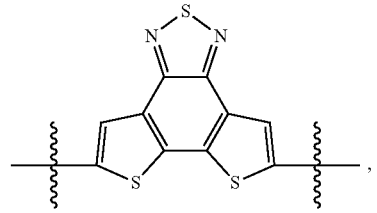

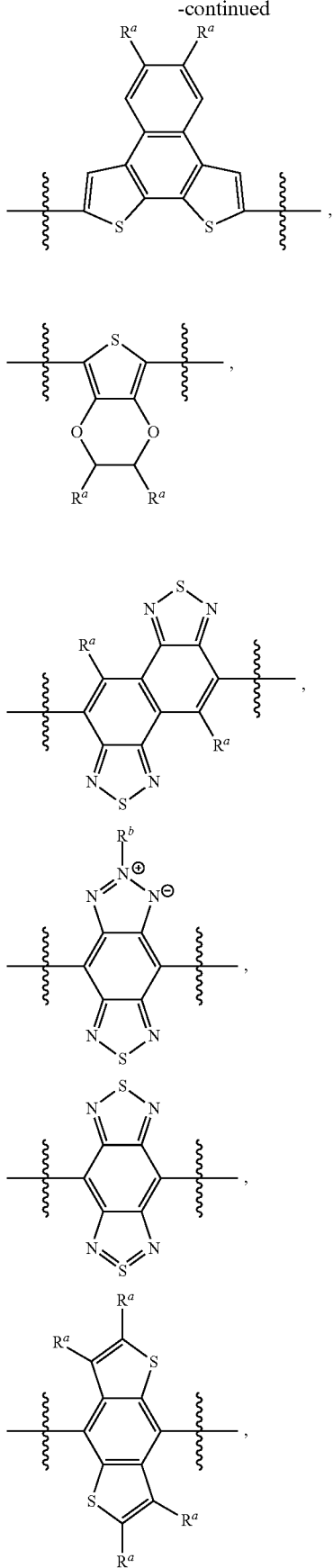
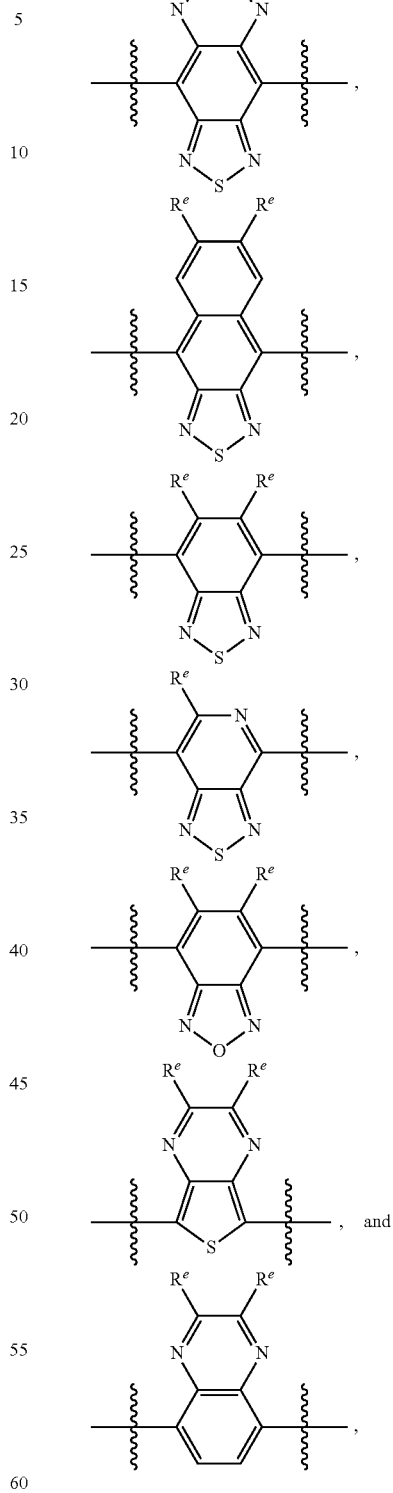
wherein:
$R^a$ is selected from the group consisting of H, F, Cl, —CN, R, —OR, —SR, —C(O)R, —OC(O)R, and —C(O)OR;
$R^b$ is selected from the group consisting of H, R, and -L-$R^f$;
$R^e$ is H or R;

$R^d$ is selected from the group consisting of H, F, Cl, —CN, R, —OR, —SR, —C(O)R, —OC(O)R, —C(O)OR, and -L-$R^f$;

$R^e$ is selected from the group consisting of H, F, Cl, —CN, R, —OR, —SR, —C(O)R, —OC(O)R, —C(O)OR, and $R^f$;

$R^f$ is a $C_{6-20}$ aryl group or a 5-20-membered heteroaryl group, each optionally substituted with 1-8 groups independently selected from the group consisting of F, Cl, —CN, R, —OR, and —SR;

L is selected from the group consisting of —O—, —S—, —C(O)—, —OC(O)—, —C(O)O—, and a covalent bond; and R is selected from the group consisting of a $C_{1-40}$ alkyl group, a $C_{1-40}$ haloalkyl group, a $C_{2-40}$ alkenyl group, and a $C_{2-40}$ alkynyl group.

In other embodiments, $M_2$ can have a formula selected from:

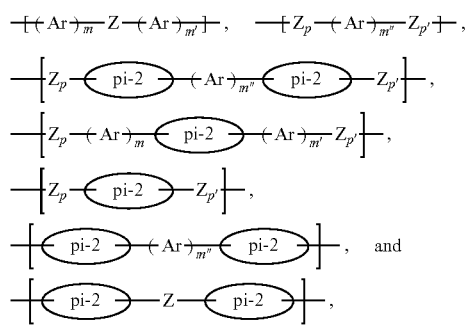

wherein m, m' and m" independently are 1, 2, 3 or 4; and Ar, pi-2 and Z are as defined herein. In such embodiments, $M_2$ can be selected from the group consisting of:

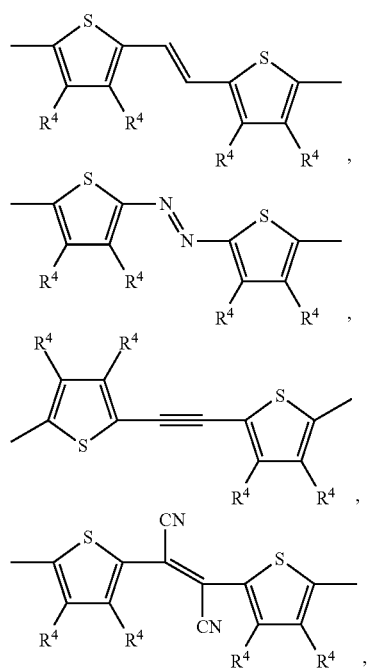

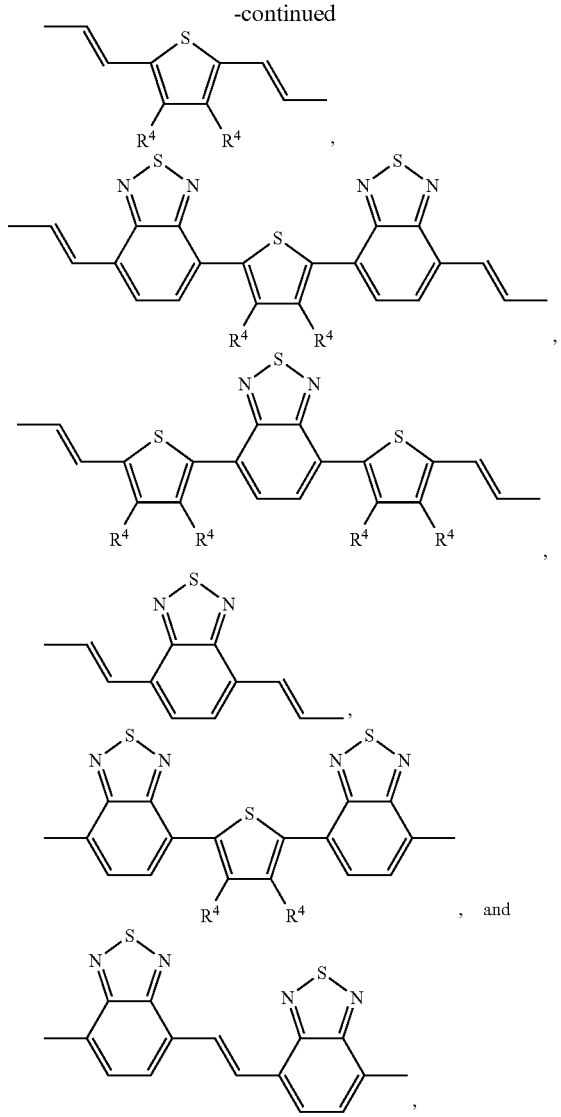

wherein $R^4$ is as defined herein.

In preferred embodiments, the present polymers are copolymers of $M_1$ and at least one $M_2$, where $M_2$ is selected from:

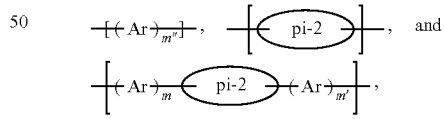

where pi-2, Ar, m, m', and m'" are as defined herein.

Certain embodiments of the present copolymers can be represented by a formula selected from the group consisting of:

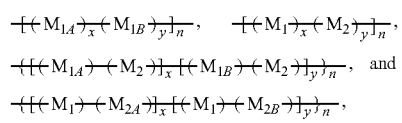

where $M_{1A}$ and $M_{1B}$ represent different repeating units $M_1$, and $M_{2A}$ and $M_{2B}$ represent different repeating units $M_2$, x and y are real numbers representing molar ratios, and n is the degree of polymerization. To illustrate, $M_{1A}$ and $M_{1B}$ can be:

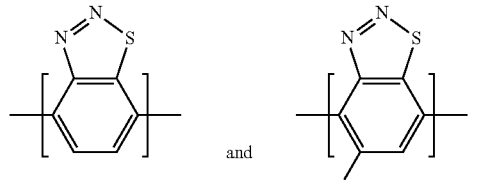
and

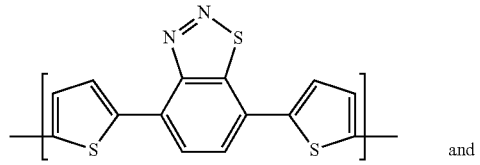
and

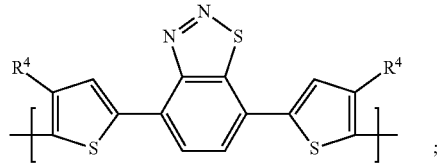
;

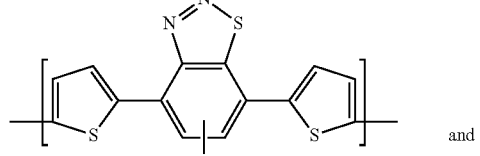
;

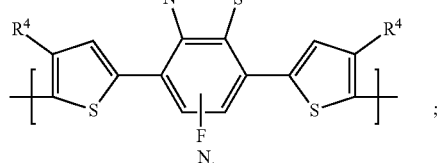
and

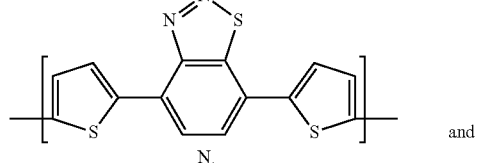
;

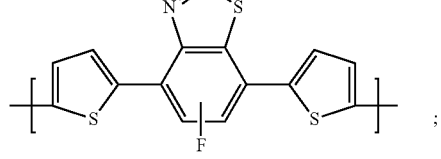
and

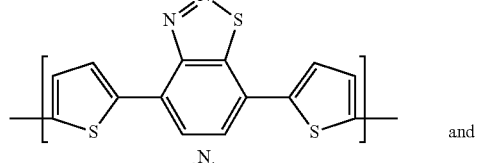
;

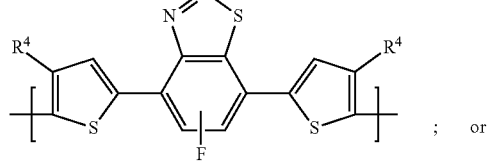
; or

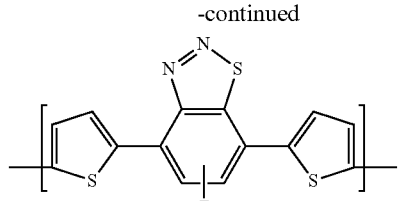
and

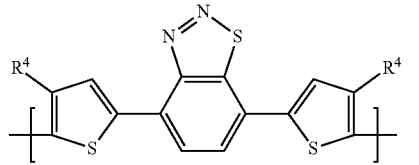
;

where $R^4$ can be selected from $R^2$, $OR^2$, and $SR^2$, where $R^2$ is a linear or branched $C_{1-40}$ alkyl or haloalkyl group. To illustrate further, $M_{2A}$ and $M_{2B}$ can be:

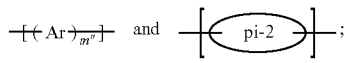

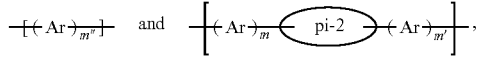

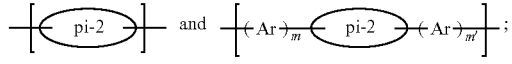

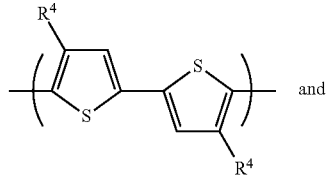
and

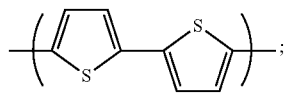
;

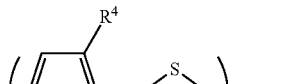
and

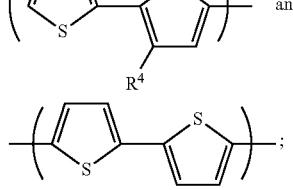
;

or two repeating units represented by:

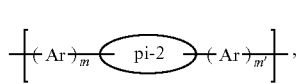
, where in $M_{2A}$, Ar is

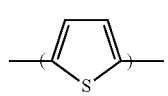

and in $M_{2B}$, Ar is

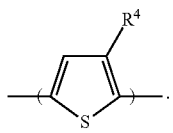

For the various polymers described above, the degree of polymerization (n) can be an integer between 3 and 1,000. In some embodiments, n can be 4-1,000, 5-1,000, 6-1,000, 7-1,000, 8-1,000, 9-1,000, or 10-1,000. For example, n can be 8-500, 8-400, 8-300, or 8-200. In certain embodiments, n can be 8-100. Embodiments of the present compounds including two or more different repeating units can have such repeating units repeating in a random or alternating manner, and the mole fraction of the two units can be between about 0.05 and about 0.95. For example, the respective mole fractions (x and y) of the two units can be between about 0.1 and about 0.9, between about 0.2 and about 0.8, between about 0.3 and about 0.7, between about 0.4 and about 0.6, or between about 0.45 and about 0.55. In certain embodiments, the present polymers can include the same mole fraction of the first unit as the second unit (i.e., x=y=0.5).

In some embodiments, the present compound can be a molecular compound including at least one benzo[d][1,2,3]thiadiazole moiety and a plurality of linear and/or cyclic conjugated moieties, such that the compound as a whole provides a pi-extended conjugated system.

To illustrate, exemplary small-molecule semiconducting compounds including at least one benzo[d][1,2,3]thiadiazole moiety and monomers for preparing the polymers described herein can be represented by the following formulae:

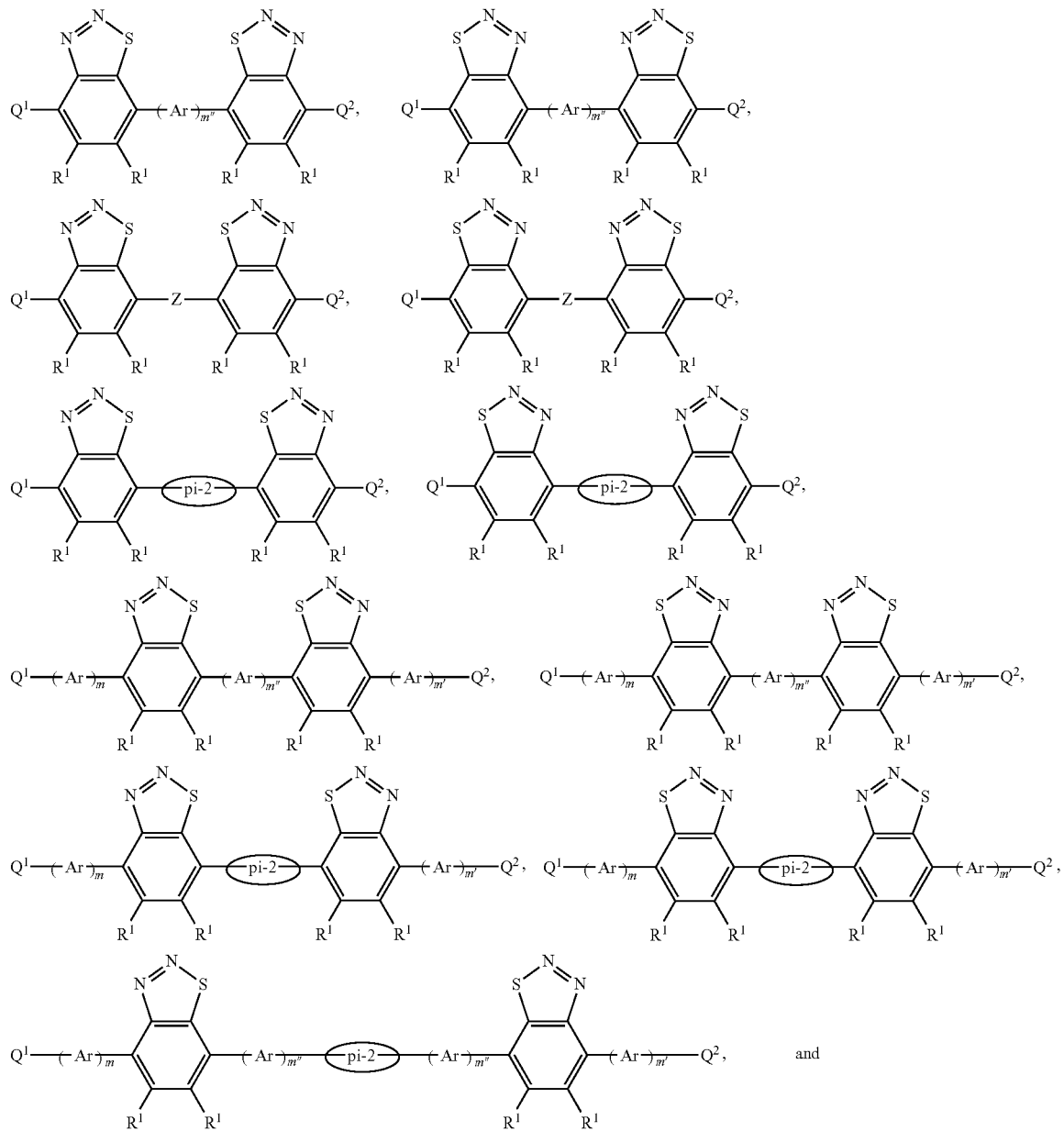

-continued

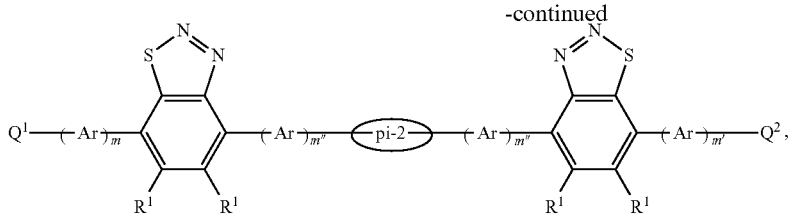

where $Q^1$ can be $X^1$ or $T^1$, $Q^2$ can be $X^2$ or $T^2$, where $X^1$ and $X^2$ can be identical or different reactive groups such as a halide, an organotin group, a boronate, or a polymerizable group, $T^1$ and $T^2$ can be identical or different terminal groups selected from H, $R^2$, and $C(O)R^2$, where $R^2$ is a $C_{1-40}$ alkyl or haloalkyl group, and pi-2, Ar, Z, m, m', m'', p, and p' are as defined herein.

Certain embodiments of molecular semiconducting compounds according to the present teachings can be represented by a formula selected from:

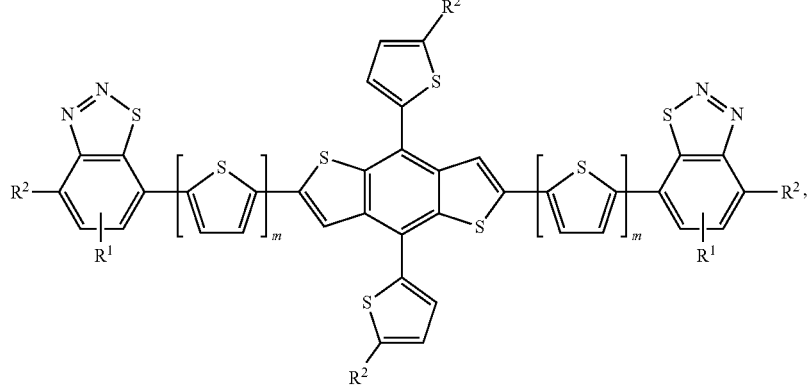
where $R^1$, $R^2$, m and m' are as defined herein.
Specific exemplary molecular semiconducting compounds according to the present teachings include:
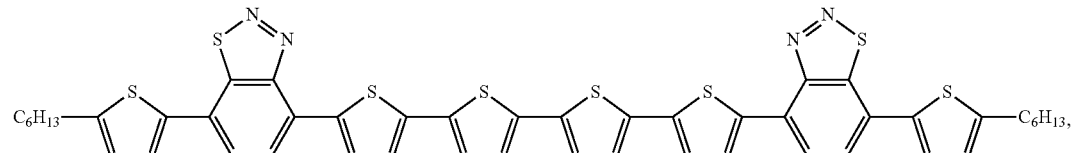
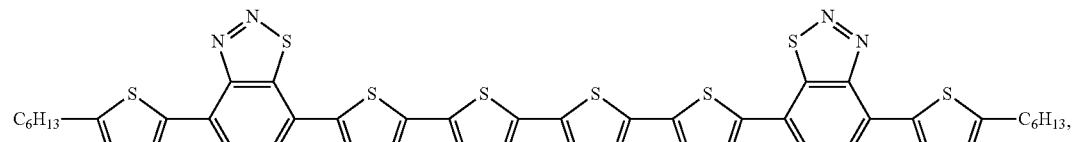
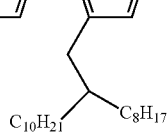
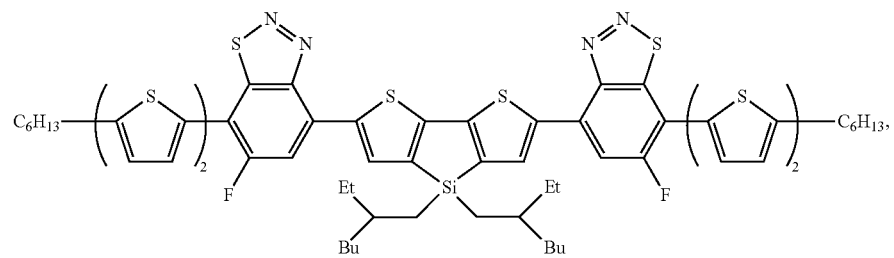
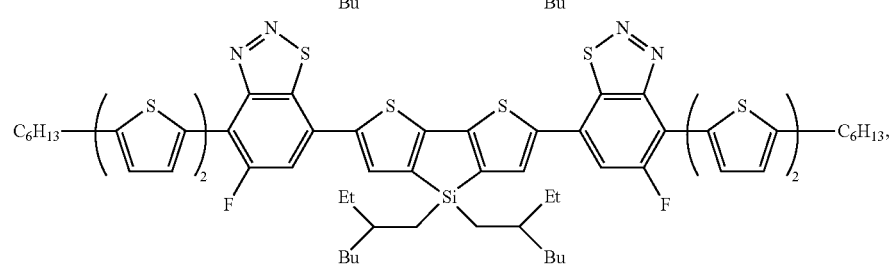

-continued

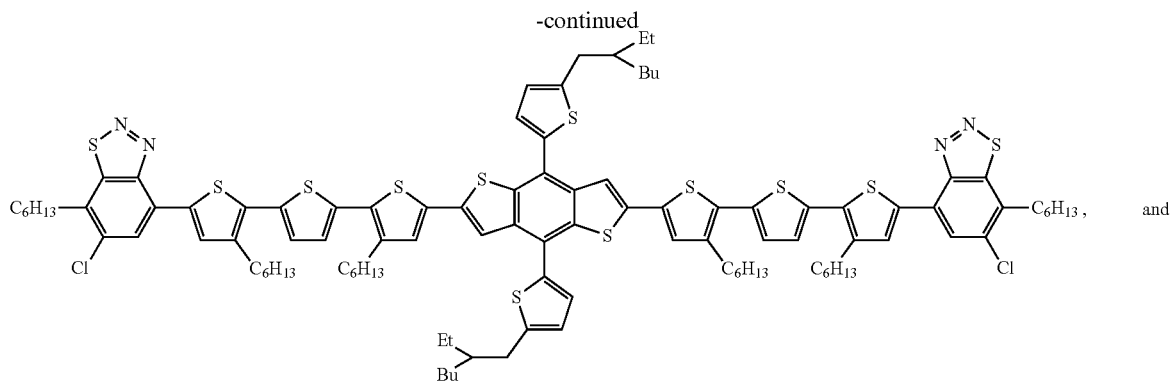

and

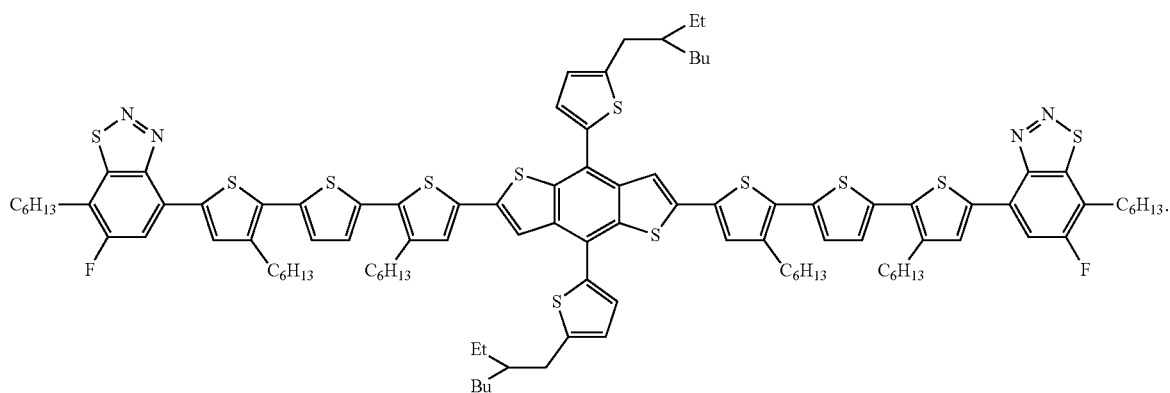

Benzo[d][1,2,3]thiadiazole and monomers including benzo[d][1,2,3]thiadiazole according to the present teachings can be prepared using the synthetic routes described hereinbelow. Other monomers according to the present teachings can be commercially available, known in the literature, or can be prepared from readily prepared intermediates by employing standard synthetic methods and procedures known to those skilled in the art. Standard synthetic methods and procedures for the preparation of organic molecules and functional group transformations and manipulations can be readily obtained from the relevant scientific literature or from standard textbooks in the field.

Synthesis of benzo[d][1,2,3]thiadiazole

Unsubstituted benzo[d][1,2,3]thiadiazole can be synthesized according, but not limited to, the following routes as described in the literature.

Scheme 1A

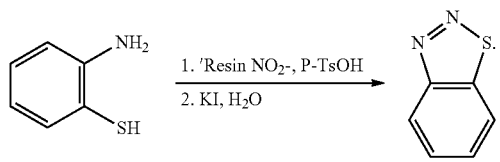

See Trusova, M.E. et al., *Synthesis*, No. 13, 2154-2158 (2011)

Scheme 1B

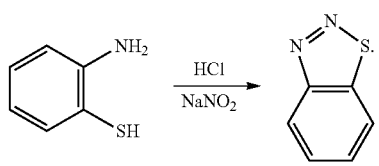

See Ward, E.R. et al., *J. Chem. Soc.*, 2374-2379 (1962)

Scheme 1C

See Hünig, S. et al., *Justus Liebigs Annalen der Chemie*, 738, 192-194 (1970)

Because the reaction intermediate is the diazonium salt of 2-aminobenzenethiol, any reagent capable of forming an aryl diazonium salt from the arylamine can be used for preparing the benzo[d][1,2,3]thiadiazole ring and its derivatives. Examples of diazotation methodologies can be found in Butler, R. N., *Chemical Reviews*, 75(2): 241-257 (1975); and in O'Leary, P., *Sci. Synth.*, 31b, 1361-1400 (2007).

Synthesis of 5- and 6-substituted benzo[d][1,2,3]thiadiazoles

Following the same approach, 5- and 6-substituted benzo[d][1,2,3]thiadiazole derivatives can be synthesized starting from the corresponding functionalized aminobenzenethiols.

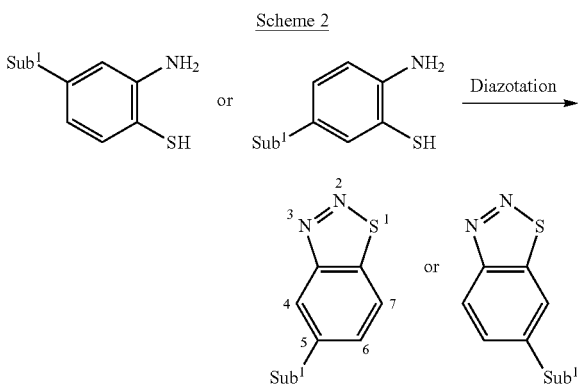

For example, the following aminobenzenethiols are either commercially available or known in the literature.

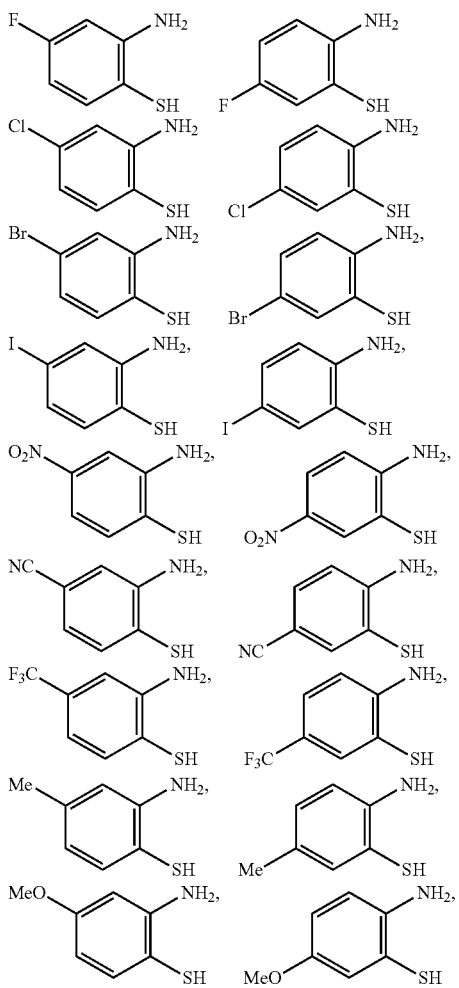

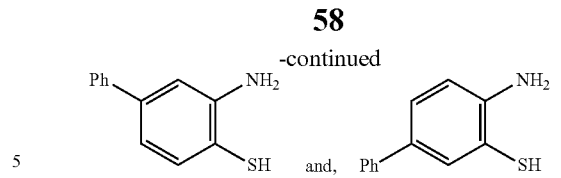

Exemplary diazotation reactions on 5- and 6-substituted benzo[d][1,2,3]thiadiazoles are described in Lionel, G. D., Ph.D. Dissertation, Cornell University, 1973. Specifically, diazotation reactions on 2-amino-5-methoxybenzenethiol can be found in Poesche, W. H., *J. Chem. Soc. B,* 368-373 (1971).

Unsubstituted and 5- or 6-substituted benzo[d][1,2,3] thiadiazoles can be halogenated or otherwise provided with reactive groups (Q) to enable coupling with the various Sp groups (Ar, Z, and/or pi-2) described herein. For example, monohalogenated benzo[d][1,2,3]thiadiazole derivatives at either the 4- or 7-position can be useful synthones for the synthesis of benzo[d][1,2,3]thiadiazole-based small-molecule semiconductors or regioregular polymers.

Synthesis of 4- and 7-Substituted Benzo[d][1,2,3]Thiadiazoles and Dibrominated Derivatives Referring to Schemes 3 and 4 below, 4-bromobenzo[d][1,2,3]thiadiazole can be synthesized from 2-amino-3-bromobenzenethiol (see Uematsu, T. et al., *Jpn. Kokai Tokkyo Koho,* JP 54145678 A, (1979)), whereas 7-bromobenzo[d][1,2,3]thiadiazole can be synthesized from 2-amino-6-bromobenzenethiol (see Wang, A. et al., *Bioorganic & Medicinal Chemistry Letters,* 20(4), 1432-1435 (2010)):

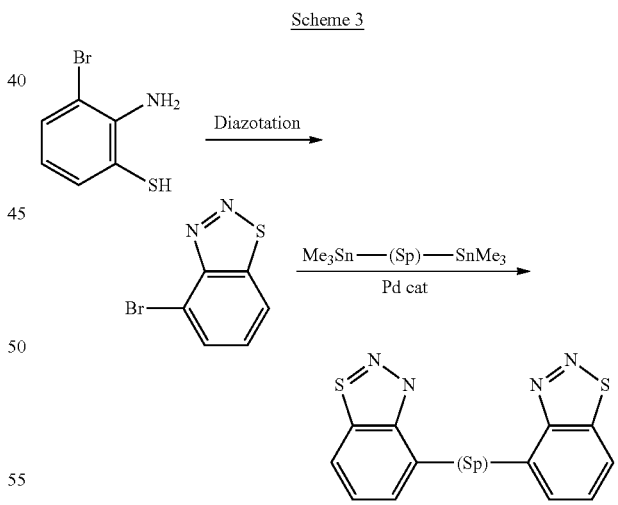

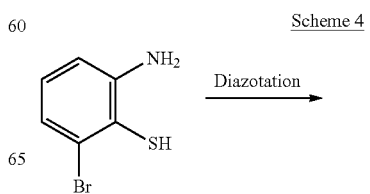

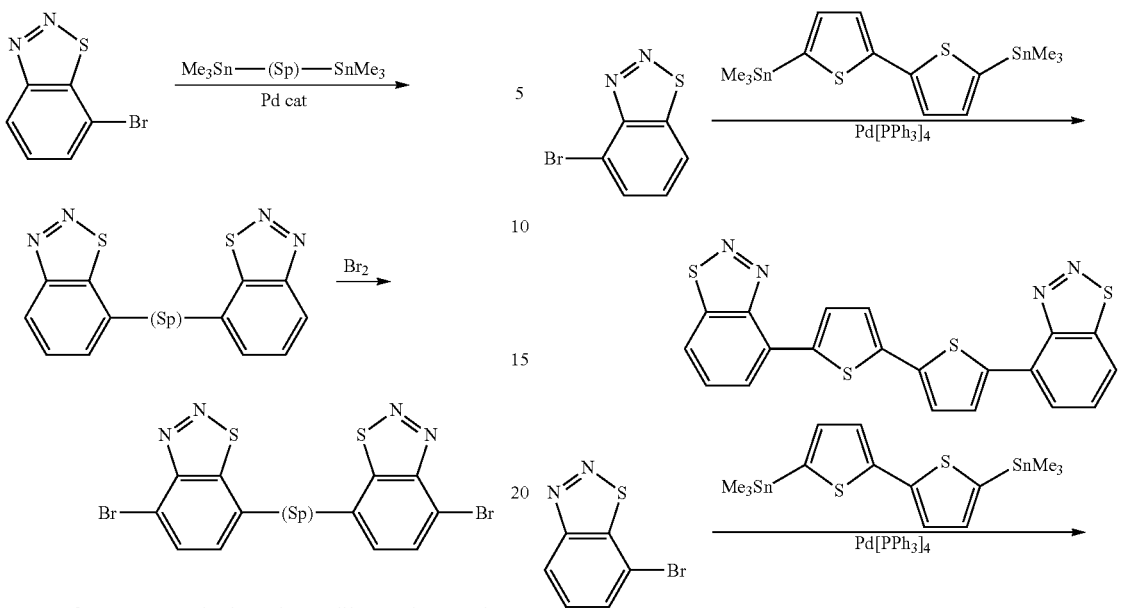

In the case of a 5- or 6-substituted-4,7-dibromobenzo[d][1,2,3]thiadiazole (e.g. 5- or 6-fluoro-4,7-dibromobenzo[d][1,2,3]thiadiazole), the reaction with the distannyl derivative could be regioselective affording the dibrominated compound directly as shown below:

Scheme 5

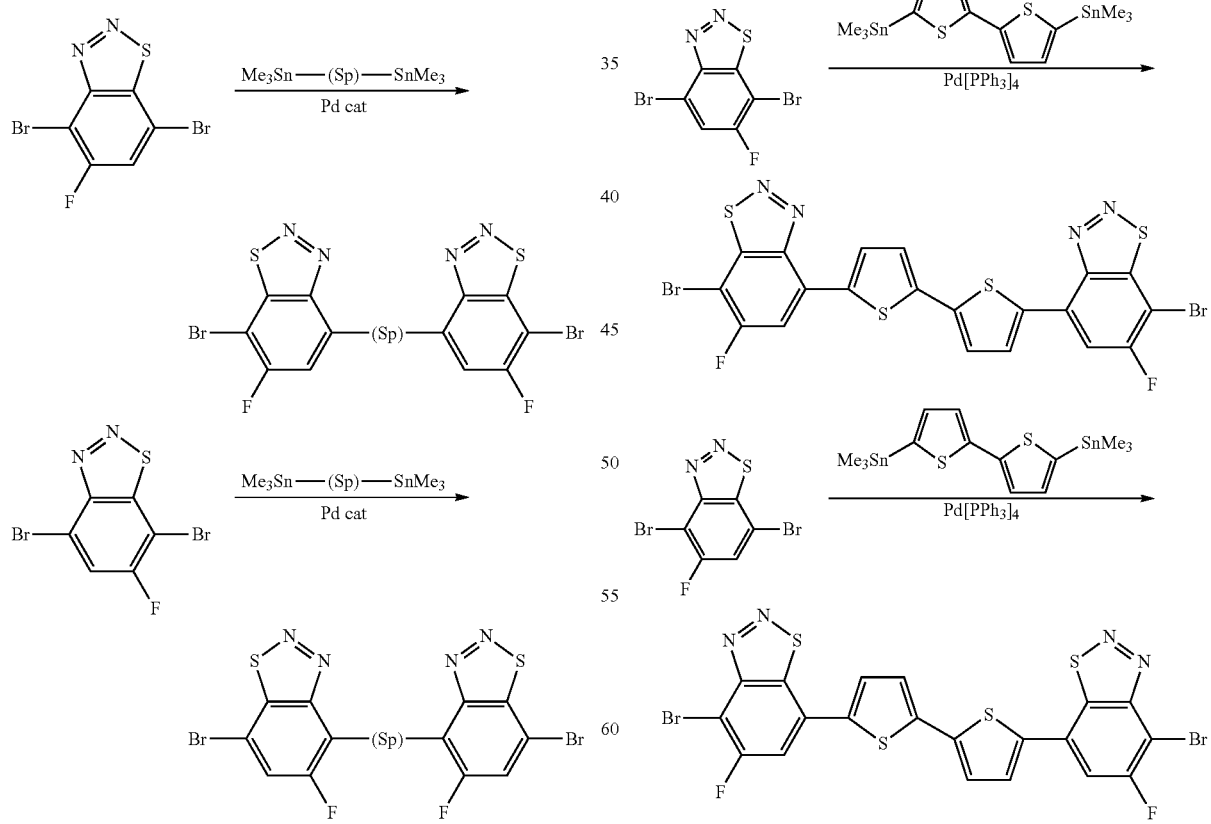

As example, Sp can be $(Ar)_{m'}$, where Ar is thienyl and m is 2:

For embodiments where the present compound is a polymer having the $M_1$ unit:

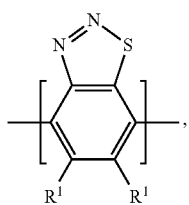

benzo[d][1,2,3]thiadiazoles that are brominated or otherwise derivatized with reactive groups at both the 4- and 7-positions can serve as a key building block.

Synthesis of 4,7-dibromobenzo[d][1,2,3]thiadiazole 4,7-Dibromobenzo[d][1,2,3]thiadiazole can be synthesized, for example, according to Schemes 6A, 6B, and 6C below:

Scheme 6A. Bromination

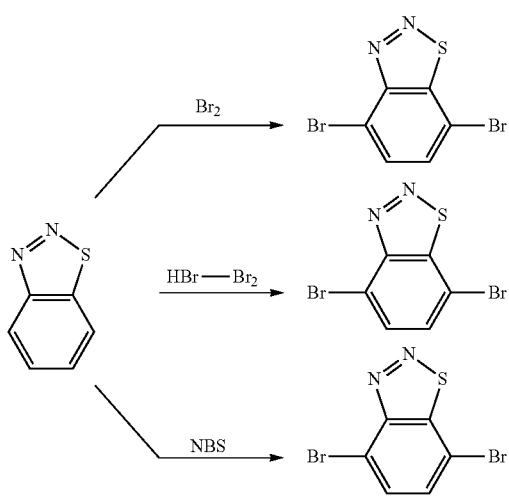

Scheme 6B. Diazotatioin

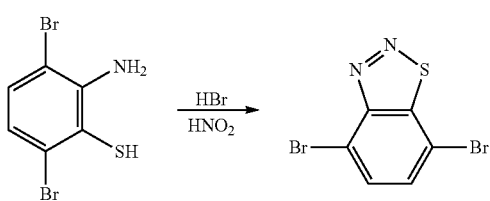

Scheme 6C. Dehalogenation

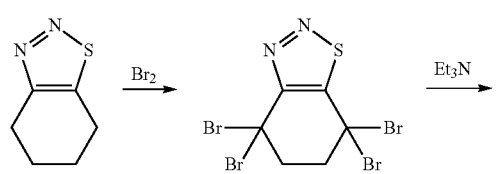

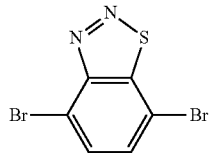

Synthesis and bromination of the starting compound is described in Zimmer, O. et al., *Liebigs Annalen der Chemie*, (4), 683-98 (1982)

Other polymerizable derivatives of benzo[d][1,2,3]thiadiazole include 4,7-distannylated benzo[d][1,2,3]thiadiazoles and 4,7-diborylated benzo[d][1,2,3]thiadiazoles.

Synthesis of 4,7-dimetallatedbenzo[d][1,2,3]thiadiazoles

Metallated derivatives can be synthesized according to Schemes 7 and 8 below.

Scheme 7. Stannylation

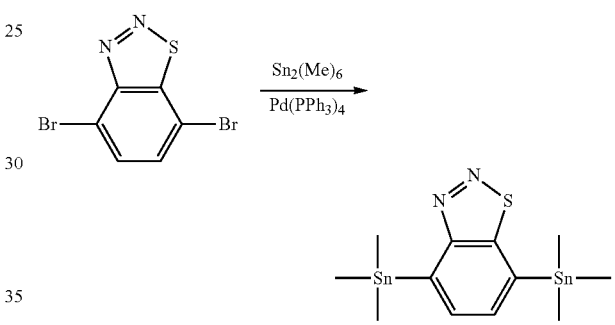

Conditions for catalytic stannylation are described in Woo, C. H. et al., *JACS*, 130(48), 16324-16329 (2008).

Scheme 8. Borylation

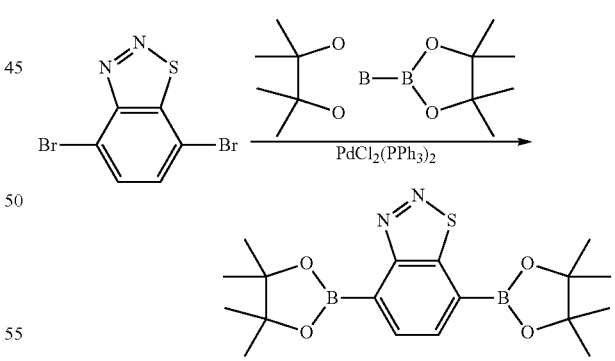

Conditions for catalytic borylation are described in Zhao, Y. et al., *Tetrahedron*, 68(44), 9113-9118 (2012).

The brominated or metallated benzo[d][1,2,3]thiadiazole derivatives then can be used as an $M_1$ unit for copolymerization with an $M_2$ unit having complementary reactive groups. Or, the brominated or metallated benzo[d][1,2,3]thiadiazole can be reacted with one or more Sp groups having complementary reactive groups to provide a pi-extended semiconducting compound. Suitable complementary reactive groups used in various coupling or polymerization reactions are well known in the art. In particular, Stille coupling or Suzuki coupling reactions can be used as described in Yamamoto, *J. Organomet. Chem.*, 653: 195-199 (2002); Walton et al., *Polymer Chemistry* (Fred J. Davis ed. 2004), p. 158-187; and Galbrecht et al., *Macromolecular Rapid Communications*, 28(4): 387-394 (2007).

The homopolymerization of $M_1$ and the copolymerization of $M_1$ and $M_2$ can be achieved via various reactions known to those skilled in the art, including procedures analogous to those described in, the entire disclosure of each of which is incorporated by reference herein for all purposes. to prepare polymeric compounds according to the present teachings with high molecular weights and in high yields ($\geq$75%) and purity, as confirmed by $^1$H NMR spectra, elemental analysis, and/or GPC measurements. Scheme 9 below outlines several exemplary reactions that can be used to polymerize $M_1$ by itself or copolymerize $M_1$ with $M_2$. It should be understood that the polymerizable groups (e.g., $SnR_3$, $BR_2$, MgX, ZnX, and Br, where X is a halogen and R is an alkyl group) can be reversed between $M_1$ and $M_2$.

Scheme 9

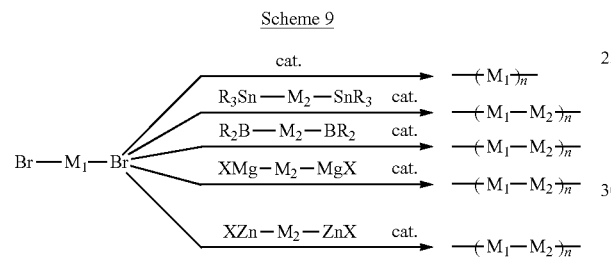

Without wishing to be bound by any particular theory, it is believed that polymers of the present teachings that have a regioregular polymeric backbone can lead to higher molecular weights, a more π-conjugated structure and, consequently better charge transport efficiencies. Accordingly, in preparing the present polymers, the present teachings can include isolating a particular average molecular weight fractions, and/or enriching and/or isolating a particular stereoisomer of $M_1$ and/or $M_2$ that has two or more stereoisomers.

Schemes 10 and 11 below illustrate specific routes to representative copolymers according to the present teachings.

Synthesis of Copolymers Including Repeating Units $M_1$

Scheme 10

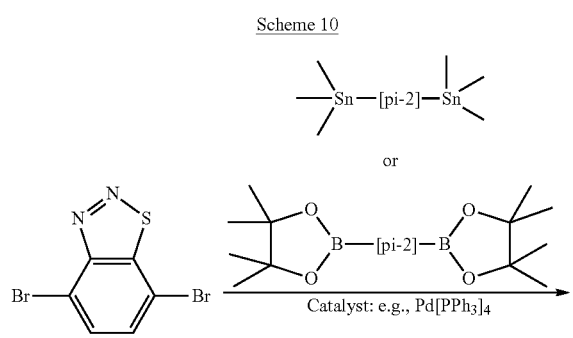

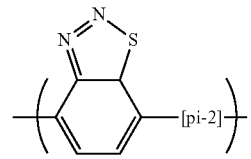

Synthesis of Regioregular Copolymers Including Repeating Units $M_1$

Scheme 11

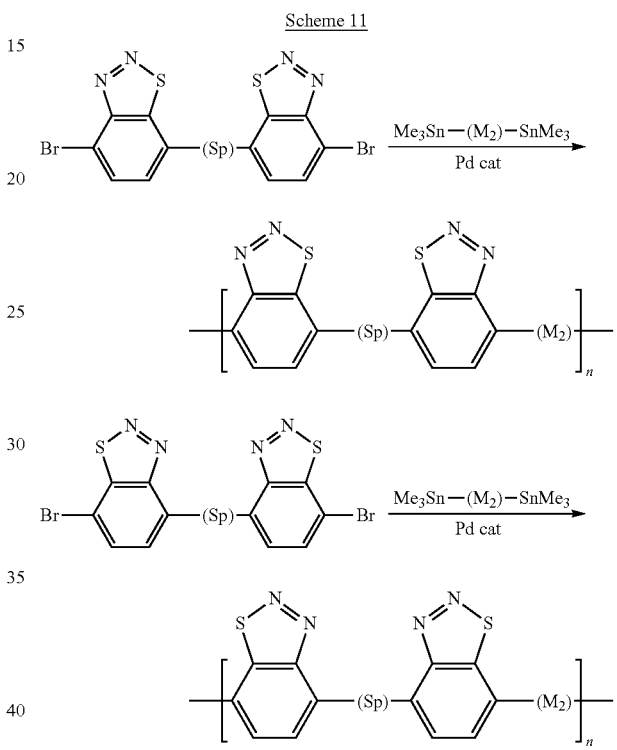

Synthesis of Copolymers Including a Repeating Unit $M_1$ that has One or More Sp Groups The reactions described in Scheme 9 above can be used analogously to couple a dibrominated benzo[d][1,2,3]thiadiazole derivative (vis-à-vis $M_1$ in Scheme 9) to an Sp group (vis-à-vis $M_2$ in Scheme 9) having complementary reactive groups to provide a more extended $M_1$ unit such as:

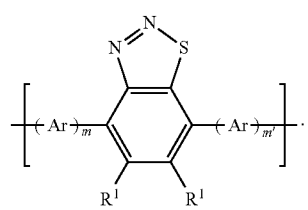

For example, a dibrominated benzo[d][1,2,3]thiadiazole derivative can be coupled to two $R^3$-substituted thienyl groups to provide the monomer:

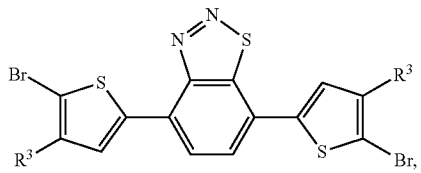
which then can be used to copolymerize with a repeating unit pi-2 as shown Scheme 12 below, where $R^3$ is a 2-decyldodecyl group:
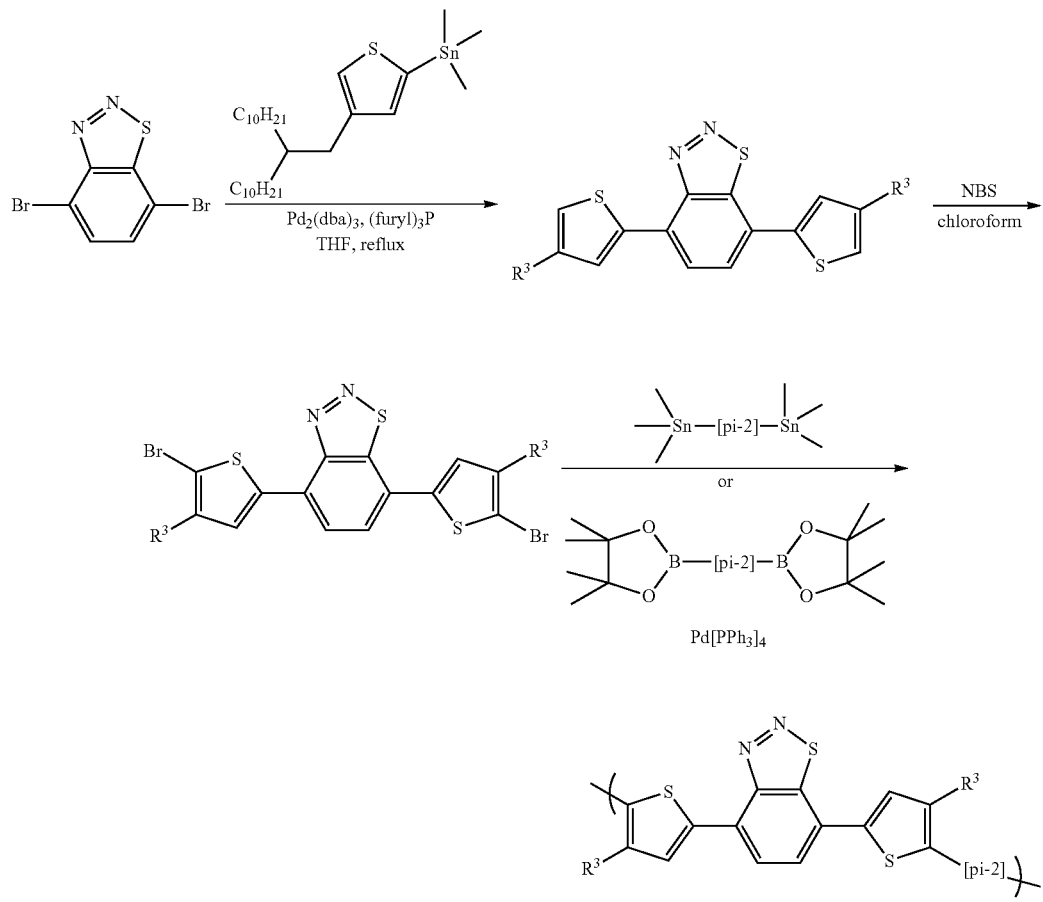
Synthesis of Small-Molecule Including Repeating Units $M_1$
Schemes 13, 14 and 15 provide exemplary synthetic procedures to representative molecular semiconducting compounds according to the present teachings.
Scheme 13
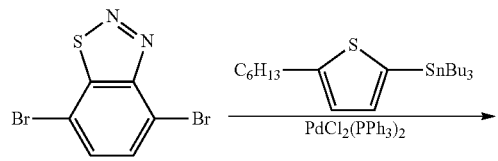

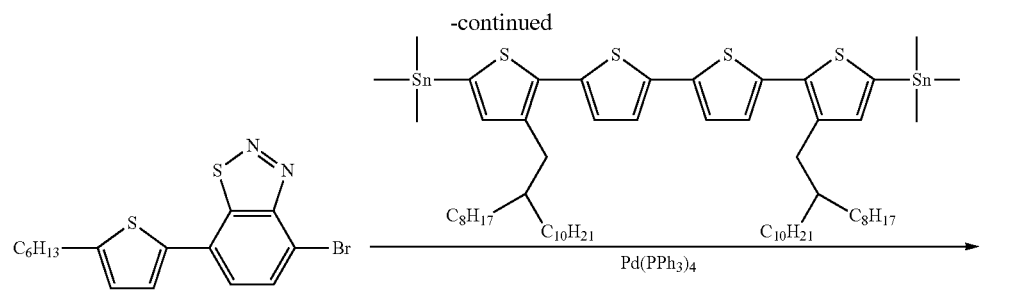
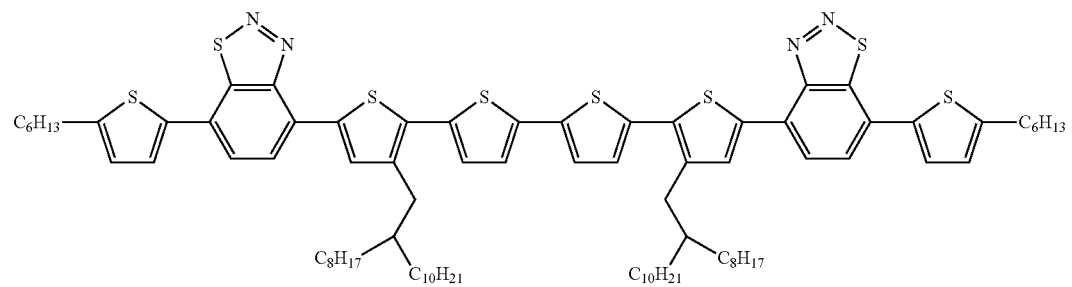
Scheme 14
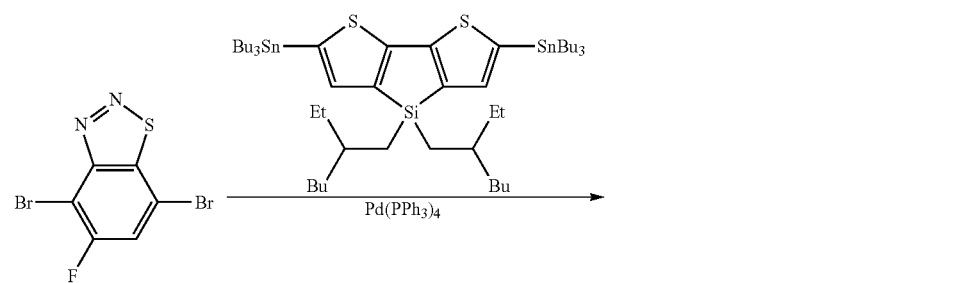
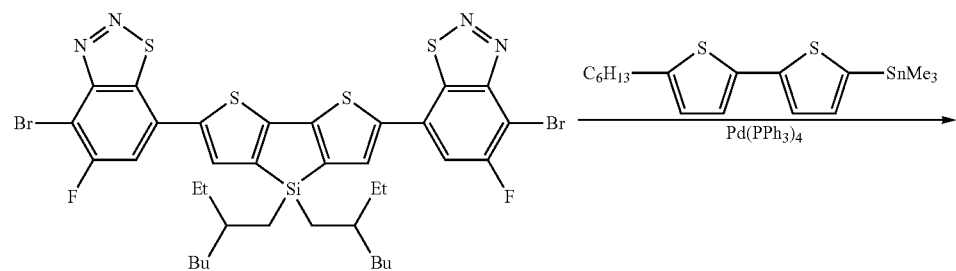
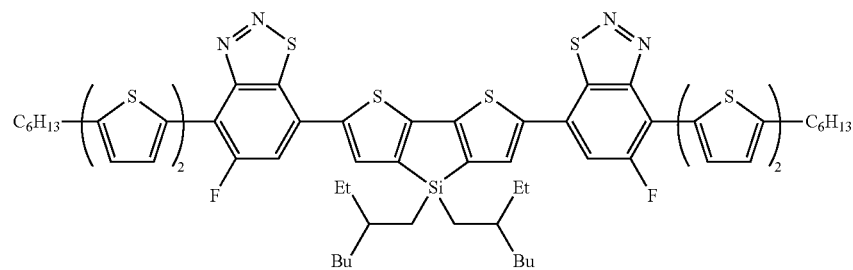

Scheme 15
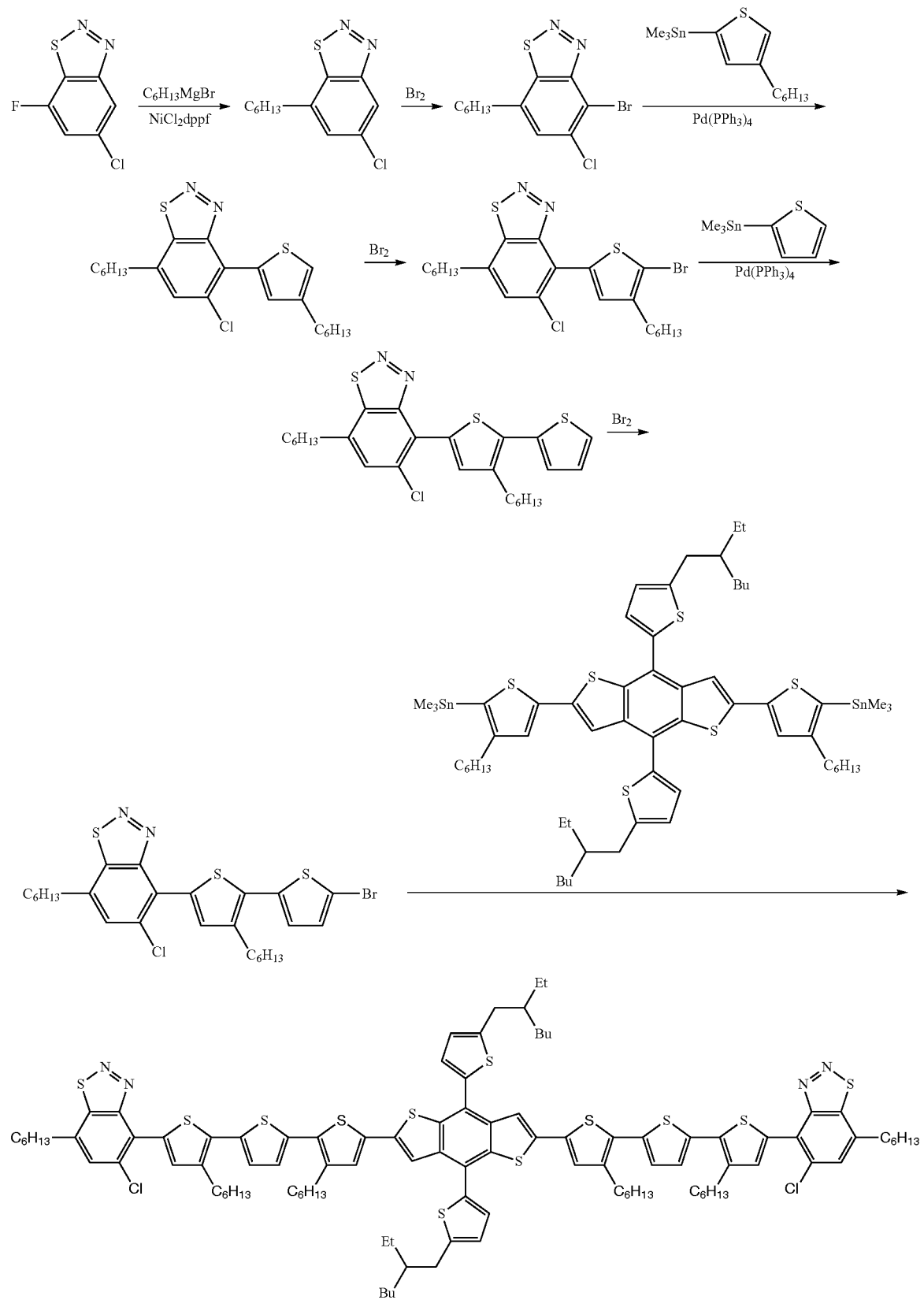

The semiconducting compounds disclosed herein can be stable in ambient conditions ("ambient stable") and soluble in common solvents. As used herein, a compound can be considered electrically "ambient stable" or "stable at ambient conditions" when the carrier mobility or the reduction-potential of the compound is maintained at about its initial measurement when the compound is exposed to ambient conditions, for example, air, ambient temperature, and humidity, over a period of time. For example, a compound according to the present teachings can be described as ambient stable if its carrier mobility or redox potential does not vary more than 20% or more than 10% from its initial value after exposure to ambient conditions, including, air, humidity and temperature, over a 3 day, 5 day, or 10 day period. In addition, a compound can be considered ambient stable if the optical absorption of the corresponding film does not vary more than 20% (preferably, does not vary more than 10%) from its initial value after exposure to ambient conditions, including air, humidity and temperature, over a 3 day, 5 day, or 10 day period.

OTFTs based on the present compounds can have long-term operability and continued high-performance in ambient conditions. For example, OTFTs based on certain embodiments of the present compounds can maintain satisfactory device performance in highly humid environment. Certain embodiments of the present compounds also can exhibit excellent thermal stability over a wide range of annealing temperatures. Photovoltaic devices can maintain satisfactory power conversion efficiencies over an extended period of time.

As used herein, a compound can be considered soluble in a solvent when at least 0.1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone, and methyl ethyl ketone; ethers such as tetrahydrofuran, dioxane, bis(2-methoxyethyl) ether, diethyl ether, di-isopropyl ether, and t-butyl methyl ether; alcohols such as methanol, ethanol, butanol, and isopropyl alcohol; aliphatic hydrocarbons such as hexanes; esters such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone. The present compounds can have room temperature solubilities in conventional organic solvents such as xylene, dichlorobenzene (DCB), and other chlorinated hydrocarbons (CHCs) as high as 60 g/L.

The present compounds can be fabricated into various articles of manufacture using solution processing techniques in addition to other more expensive processes such as vapor deposition. Various solution processing techniques have been used with organic electronics. Common solution processing techniques include, for example, spin coating, drop-casting, zone casting, dip coating, blade coating, or spraying. Another example of solution processing technique is printing. As used herein, "printing" includes a noncontact process such as inkjet printing, microdispensing and the like, and a contact process such as screen-printing, gravure printing, offset printing, flexographic printing, lithographic printing, pad printing, microcontact printing and the like.

Compounds of the present teachings can be used to prepare semiconductor materials (e.g., compositions and composites), which in turn can be used to fabricate various articles of manufacture, structures, and devices. In some embodiments, semiconductor materials incorporating one or more compounds of the present teachings can exhibit n-type semiconductor activity, ambipolar activity, light absorption, and light emission.

The present teachings, therefore, further provide methods of preparing a semiconductor material. The methods can include preparing a composition that includes one or more compounds disclosed herein dissolved or dispersed in a liquid medium such as a solvent or a mixture of solvents, depositing the composition on a substrate to provide a semiconductor material precursor, and processing (e.g., heating) the semiconductor precursor to provide a semiconductor material (e.g., a thin film semiconductor) that includes a compound disclosed herein. In various embodiments, the liquid medium can be an organic solvent, an inorganic solvent such as water, or combinations thereof. In some embodiments, the composition can further include one or more additives independently selected from viscosity modulators, detergents, dispersants, binding agents, compatibilizing agents, curing agents, initiators, humectants, antifoaming agents, wetting agents, pH modifiers, biocides, and bacteriostats. For example, surfactants and/or polymers (e.g., polystyrene, polyethylene, poly-alpha-methylstyrene, polyisobutene, polypropylene, polymethylmethacrylate, and the like) can be included as a dispersant, a binding agent, a compatibilizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying.

Various articles of manufacture including electronic devices, optical devices, and optoelectronic devices, such as thin film semiconductors, field effect transistors (e.g., thin film transistors), photovoltaics, photodetectors, organic light emitting devices such as organic light emitting diodes (OLEDs) and organic light emitting transistors (OLETs), complementary metal oxide semiconductors (CMOSs), complementary inverters, diodes, capacitors, sensors, D flip-flops, rectifiers, and ring oscillators, that make use of the compounds disclosed herein are within the scope of the present teachings as are methods of making the same. The present compounds can offer processing and operation advantages in the fabrication and/or the use of these devices. For example, articles of manufacture such as the various devices described herein can include a composite having a semiconductor material of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), and self-assembled superlattice/self-assembled nanodielectric (SAS/SAND) materials (e.g., described in Yoon, M-H. et al., *PNAS*, 102 (13): 4678-4682 (2005), the entire disclosure of which is incorporated by reference herein), as well as hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANI), polypyrrole (PPy)). One or more of the composites described herein can be embodied within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Other articles of manufacture in which compounds of the present teachings are useful are photovoltaics or solar cells. Particularly, polymers of the present teachings can exhibit broad optical absorption and/or a tuned redox properties and bulk carrier mobilities, making them desirable for such applications. For example, the polymers described herein can be used as a donor (p-type) semiconductor in a photovoltaic design, which includes an adjacent n-type semiconductor material that forms a p-n junction. The polymers can be in the form of a thin film semiconductor, which can be deposited on a substrate to form a composite. Exploitation of polymers of the present teachings in such devices is within the knowledge of a skilled artisan.

Accordingly, another aspect of the present teachings relates to methods of fabricating an organic field effect transistor that incorporates a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures. FIG. 1 illustrates the four common types of OFET structures: (a) bottom-gate top-contact structure, (b) bottom-gate bottom-contact structure, (c) top-gate bottom-contact structure, and (d) top-gate top-contact structure. As shown in FIG. 1, an OFET can include a dielectric layer (e.g., shown as 8, 8', 8'', and 8'' in FIGS. 1*a*, 1*b*, 1*c*, and 1*d*, respectively), a semiconductor/channel layer (e.g., shown as 6, 6', 6'', and 6'' in FIGS. 1*a*, 1*b*, 1*c*, and 1*d*, respectively), a gate contact (e.g., shown as 10, 10', 10'', and 10'' in FIGS. 1*a*, 1*b*, 1*c*, and 1*d*, respectively), a substrate (e.g., shown as 12, 12', 12'', and 12'' in FIGS. 1*a*, 1*b*, 1*c*, and 1*d*, respectively), and source and drain contacts (e.g., shown as 2, 2', 2'', 2'', 4, 4', 4'', and 4'' in FIGS. 1*a*, 1*b*, 1*c*, and 1*d*, respectively).

In certain embodiments, OTFT devices can be fabricated with the present semiconducting compounds on doped silicon substrates, using $SiO_2$ as the dielectric, in top-contact geometries. In particular embodiments, the active semiconductor layer which incorporates at least a semiconducting compound of the present teachings can be deposited at room temperature or at an elevated temperature. In other embodiments, the active semiconductor layer which incorporates at least one semiconducting compound of the present teachings can be applied by spin-coating or printing as described herein. For top-contact devices, metallic contacts can be patterned on top of the films using shadow masks.

In certain embodiments, OTFT devices can be fabricated with the present compounds on plastic foils, using polymers as the dielectric, in top-gate bottom-contact geometries. In particular embodiments, the active semiconducting layer which incorporates at least a semiconducting compound of the present teachings can be deposited at room temperature or at an elevated temperature. In other embodiments, the active semiconducting layer which incorporates at least a semiconducting compound of the present teachings can be applied by spin-coating or printing as described herein. Gate and source/drain contacts can be made of Au, other metals, or conducting polymers and deposited by vapor-deposition and/or printing.

Figure 2:
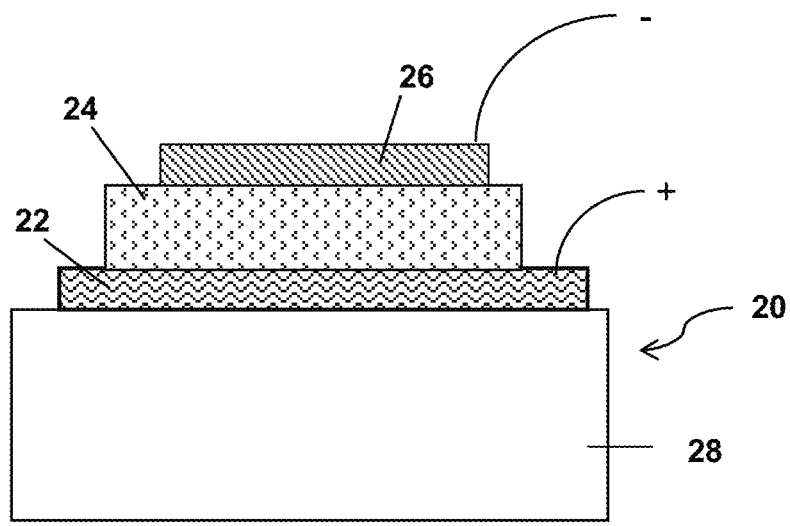
FIG. 2 illustrates a representative structure of a bulk-heterojunction organic photovoltaic device (also known as a solar cell), which can incorporate one or more compounds of the present teachings as the donor and/or acceptor materials.
Figure 3:
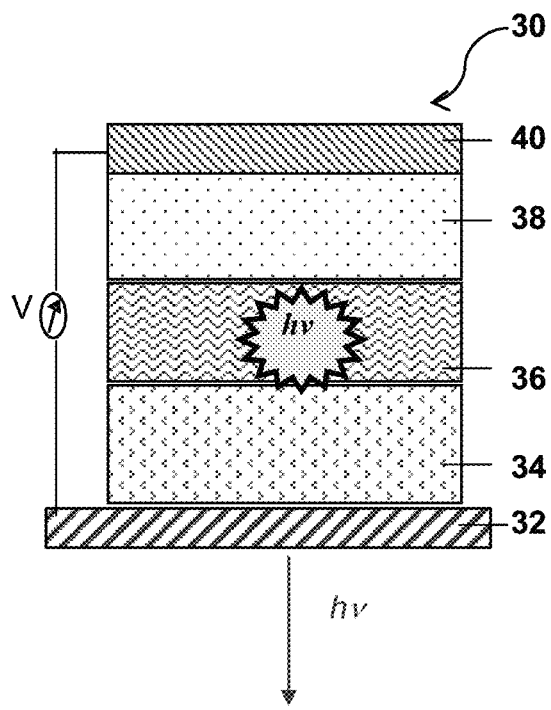
FIG. 3 illustrates a representative structure of an organic light-emitting device which can incorporate one or more compounds of the present teachings as electron-transporting and/or emissive and/or hole-transporting materials.

Similarly, another aspect of the present teachings relates to methods of fabricating an organic light-emitting transistor, an organic light-emitting diode (OLED), or an organic photovoltaic device that incorporates one or more semiconductor materials of the present teachings. FIG. 2 illustrates a representative structure of a bulk-heterojunction organic photovoltaic device (also known as solar cell) which can incorporate one or more semiconducting compounds of the present teachings as the donor material. As shown, a representative solar cell generally includes a substrate 20 (e.g., glass), an anode 22 (e.g., ITO), a cathode 26 (e.g., aluminium or calcium), and an active layer 24 between the anode and the cathode which can incorporate one or more semiconducting compounds of the present teachings as the electron donor (p-channel) materials. FIG. 3 illustrates a representative structure of an OLED which can incorporate one or more semiconducting compounds of the present teachings as electron-transporting and/or emissive and/or hole-transporting materials. As shown, an OLED generally includes a substrate 30 (not shown), a transparent anode 32 (e.g., ITO), a cathode 40 (e.g., metal), and one or more organic layers which can incorporate one or more semiconducting compounds of the present teachings as hole-transporting (n-channel) (layer 34 as shown) and/or emissive (layer 36 as shown) and/or electron-transporting (p-channel) materials (layer 38 as shown).

The following examples are provided to illustrate further and to facilitate the understanding of the present teachings and are not in any way intended to limit the invention. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

All reagents were purchased from commercial sources and used without further purification unless otherwise noted. Reagents 3, 4, and 5 were synthesized according to procedures similar to those reported in the literature. See (a) Yue, W.; Zhao, Y.; Tian, H.; Song, D.; Xie, Z.; Yan, D.; Geng, Y.; Wang, F. *Macromolecules* 2009, 42, 6510; (b) Zhu, Z.; Drees, M.; Pan, H.; Yao, Y.; Yan, H.; Lu, S.; Facchetti, A. US2010/135701, 2010; (c) Hou, J.; Park, M.-H.; Zhang, S.; Yao, Y.; Chen. L.-M.; Li, J.-H.; Yang, Y. *Macromolecules* 2008, 41, 6012; (d) Watson, M. D. US2010/0252112, 2010; and (e) Janietz, S.; Barche, J.; Wedel, A.; Sainova, D. *Macromol. Chem. Phys.* 2004, 205, 1916. Conventional Schlenk techniques were used and reactions were carried out under $N_2$ unless otherwise noted.

Characterization data are provided in some cases by $^1$H-NMR, optical absorption spectroscopy, and cyclic voltammetry. NMR spectra were recorded on an Inova 500 NMR spectrometer ($^1$H, 500 MHz). UV-vis spectra were recorded on a Cary 50 UV-vis spectrophotometer. Cyclic voltammetry measurement was carried out under nitrogen at a scan rate of 50 mV/s using a BAS-CV-50W voltammetric analyzer. A platinum disk working electrode, a platinum wire counter electrode and a silver wire reference electrode were employed and Fc/Fc⁻ (0.54 V vs SCE) was used as reference for all measurements.

Example 1. Synthesis of 4,7-dibromobenzo[d][1,2,3]thiadiazole

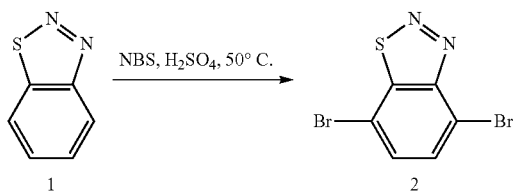 [SMILES: c1ccc2snnc2c1 ; Brc1ccc(Br)c2snnc12]

Benzo[1,2,3]thiadiazole (1, 193 mg, 1.4 mmol) was dissolved in concentrated sulfuric acid (95-98%, 20 mL) and NBS (556 mg, 3.1 mmol) was then added in one portion. The resulting solution was heated to 50° C. and maintained at this temperature overnight. Upon cooling to rt, the reaction mixture was poured onto ice water (about 100 mL). This mixture was extracted with chloroform (100 mL), and the organic layer was washed with additional water (3×100 mL), dried over anhydrous magnesium sulfate, and concentrated in vacuo, leading to a beige solid as the product (2, 370 mg, 89.8%). $^1$H NMR (CDCl3, 400 MHz): 7.69-7.71 (d, J=8.0 Hz, 1H), 7.65-7.67 (d, J=8.0 Hz, 1H).

Example 2. Synthesis of Polymer P1

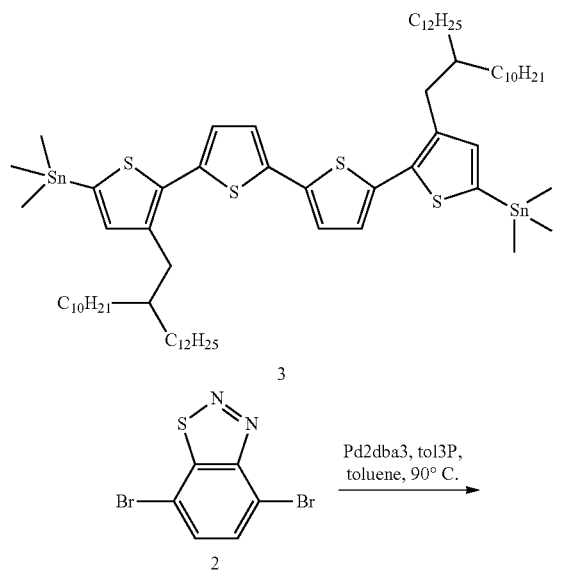

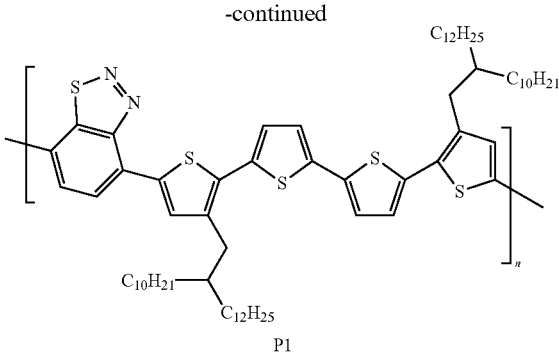

Compound 2 (34.3 mg, 0.12 mmol) and reagent 3 (155.6 mg, 0.12 mmol) were added to a Schlenk flask with tris(dibenzylideneacetone)dipalladium(0) (2.2 mg, 0.0024 mmol) and tri(o-tolyl)phosphine (5.7 mg, 0.018 mmol). The flask was subject to vacuum and then backfilled with Ar, and this cycle was repeated four times. Under Ar, anhydrous toluene (15 mL) was added, and the resulting mixture was heated to 90° C. and maintained at this temperature for about 20 h. Bromobenzene (0.5 mL) was added to the reaction mixture and it was maintained at 90° C. for an additional 4 h. Upon cooling to rt, the reaction mixture was precipitated in methanol (about 200 mL), and the precipitate was collected by filtration and washed with methanol. This crude product was then subject to Soxhlet extraction with methanol (21 h), ethyl acetate (20 h), and finally extracted with chloroform. Upon cooling to rt, the chloroform extract was concentrated to about 5 mL, which was precipitated in methanol (about 100 mL). The precipitate was collected by filtration, washed with methanol, and dried in vacuum, leading to a dark red/brown solid as the polymer product P1 (87.8 mg, 66.3%). HOMO Energy: −5.62 eV; LUMO Energy: −3.77 eV; Optical band gap: 1.85 eV.

Figure 4:
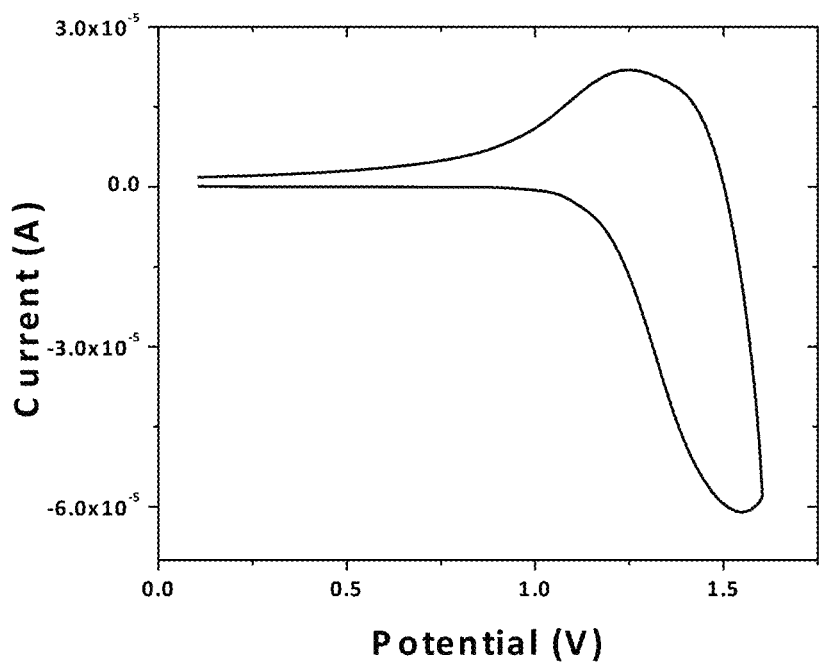
FIG. 4 shows a cyclic voltammogram of an exemplary polymer, P1, according to the present teaching in $CH_2Cl_2$.

FIG. 4 shows a cyclic voltammogram of P1 in $CH_2Cl_2$.

Example 3. Synthesis of Polymer P2

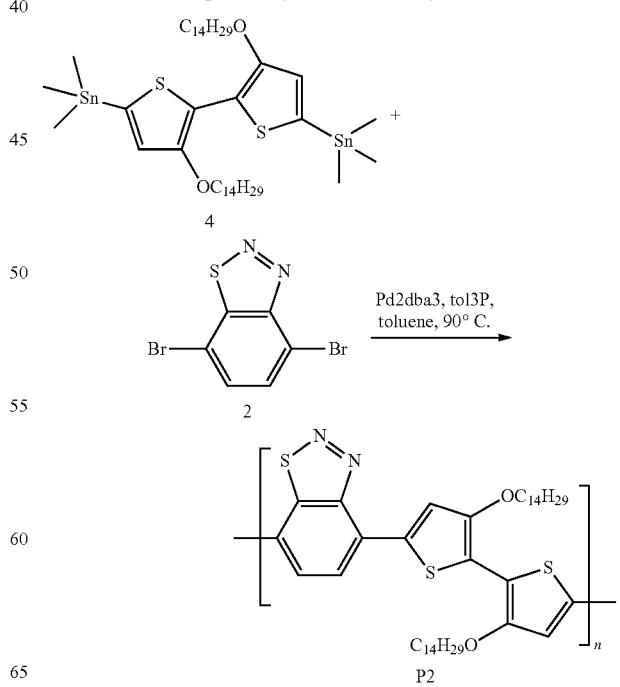

Compound 2 (30.7 mg, 0.10 mmol) and reagent 4 (95.7 mg, 0.10 mmol) were added to a Schlenk flask with tris(dibenzylideneacetone)dipalladium(0) (1.9 mg, 0.0021 mmol) and tri(o-tolyl)phosphine (5.1 mg, 0.017 mmol). The flask was subject to vacuum and then backfilled with Ar. This cycle was repeated four times. While under Ar, anhydrous toluene (10 mL) was added. The resulting mixture was heated to about 90° C. and maintained at this temperature for 15 h. Bromobenzene (0.5 mL) was added to the reaction mixture and heating was continued at 90° C. for an additional 4 h. Upon cooling to rt, the reaction mixture was precipitated in methanol (150 mL). The precipitate was collected by filtration and washed with methanol. This crude product was then purified by Soxhlet extraction with methanol (19 h), ethyl acetate (25 h), and hexanes (21 h), leading to dark solid as the product P2 after drying (41.4 mg, 54.8%). HOMO Energy: −4.82 eV; LUMO Energy: −3.33 eV; Optical band gap: 1.49 eV.

Figure 5:
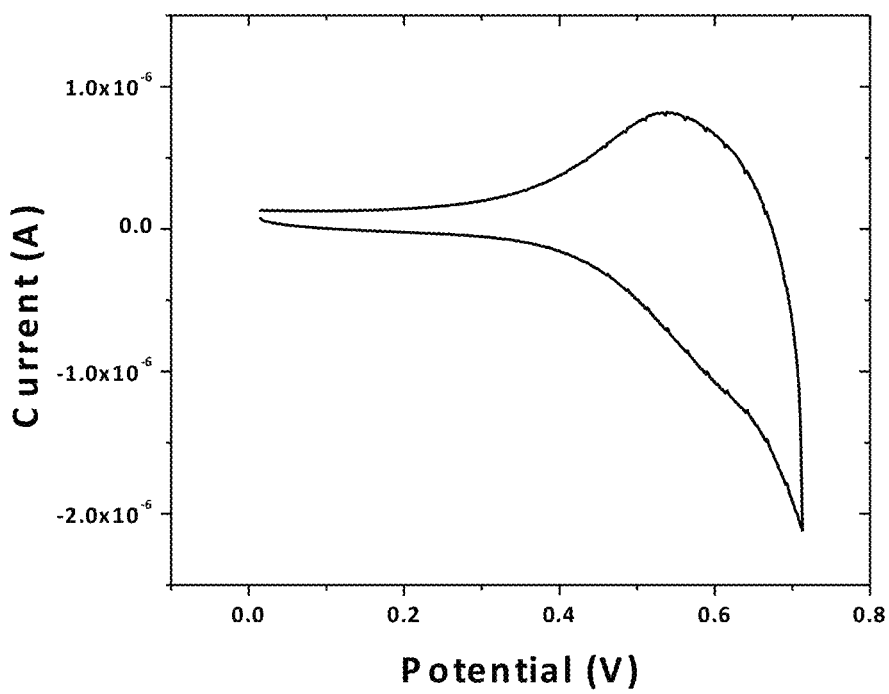
FIG. 5 shows a cyclic voltammogram of another exemplary polymer, P2, according to the present teaching in $CH_2Cl_2$.

FIG. 5 shows a cyclic voltammogram of P2 in $CH_2Cl_2$.

Example 4. Synthesis of Polymer P3

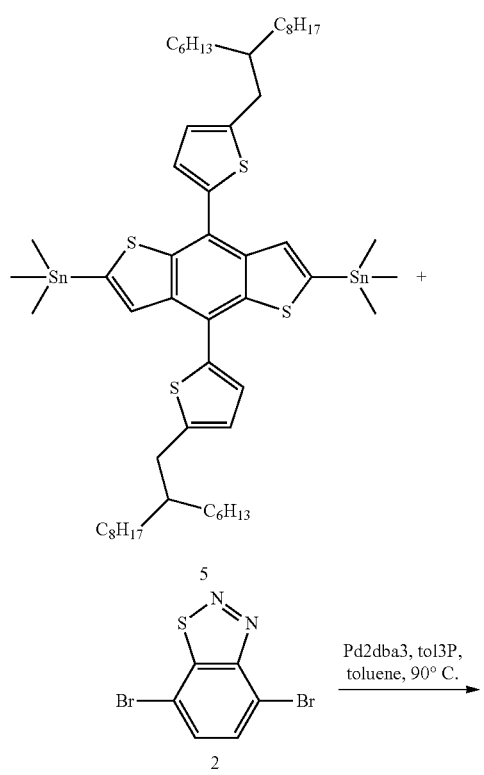

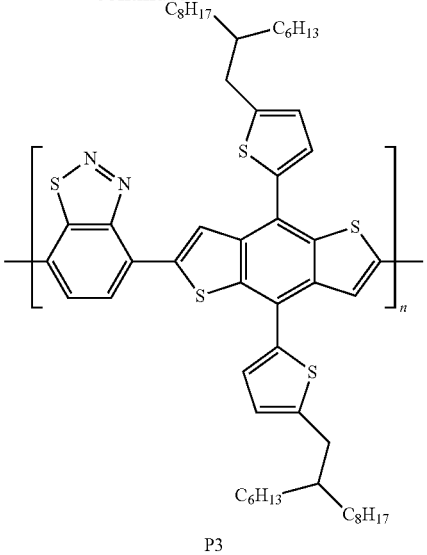

P3

Compound 2 (36.6 mg, 0.12 mmol) and reagent 5 (148 mg, 0.13 mmol) were added to an air-free flask with tris(dibenzylideneacetone)dipalladium(0) (4.8 mg, 0.0052 mmol) and tri(o-tolyl)phosphine (6.4 mg, 0.021 mmol). The flask was subject to vacuum and then backfilled with Ar, and this cycle was repeated four times. While under Ar, anhydrous chlorobenzene (15 mL) was added, and the resulting mixture was heated to about 90° C. and maintained at this temperature for 18 h. Bromobenzene (0.5 mL) was added to the reaction mixture and heating was continued at 90° C. for an additional 3 h. Upon cooling to rt, the reaction mixture was precipitated in methanol (100 mL). The precipitate was collected by filtration and washed with methanol. This crude product was then subject to Soxhlet extraction with methanol (16 h) and ethyl acetate (16 h). Finally, it was extracted with chloroform. Upon cooling to rt, the chloroform extract was concentrated to about 5 mL, which was precipitated in methanol (200 mL). The precipitate was collected by filtration, washed with methanol, and dried in vacuum, leading to a dark red solid as the product P3 (108.1 mg, 93.2%). The optical band-gap of P3 was estimated to be about −1.95 eV.

Example 5. Synthesis of Polymer P4

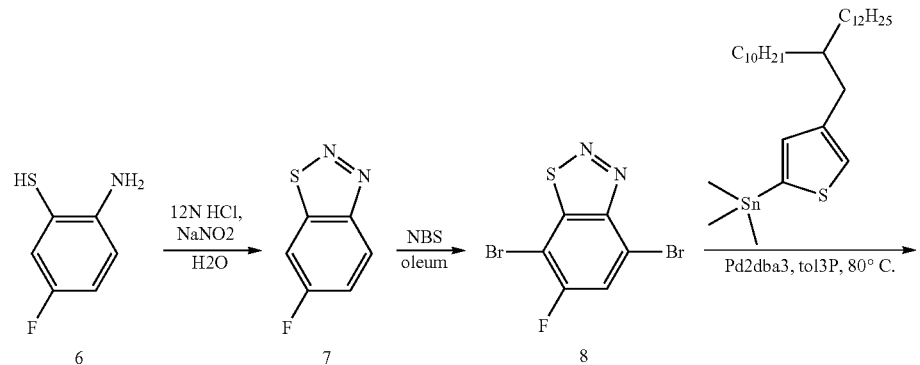

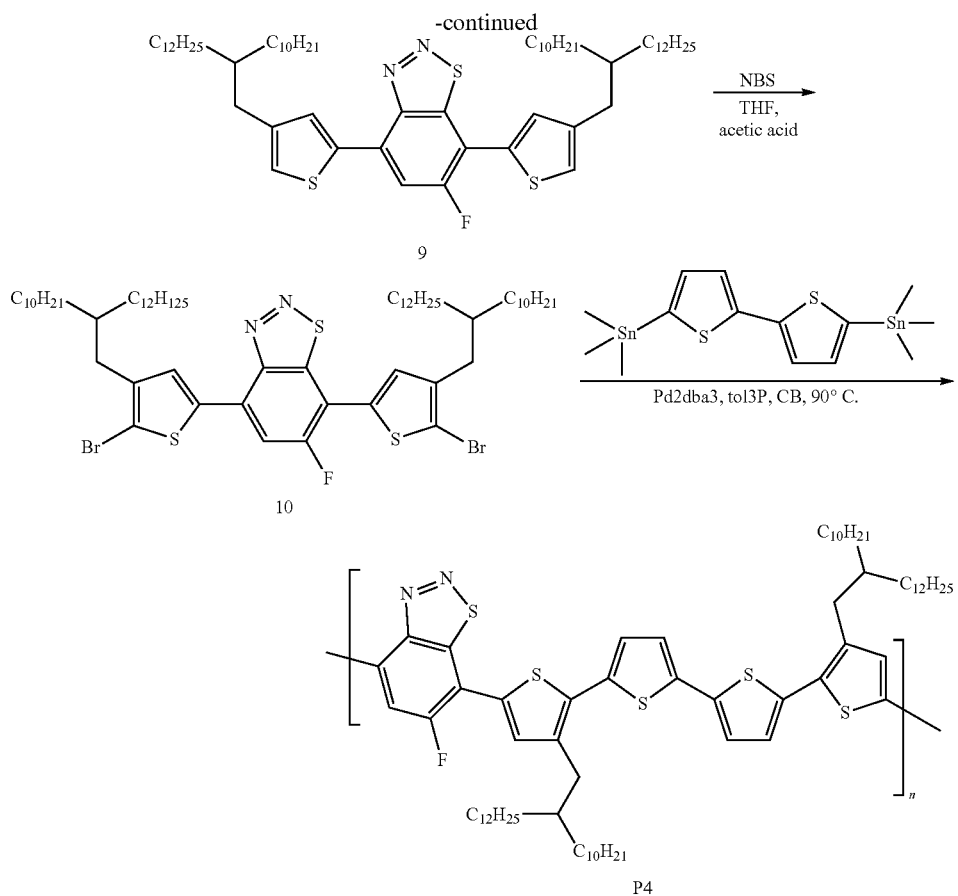

Step 1: To a mixture of compound 6 (875 mg, 5.98 mmol) in water (6 mL) was added 12M HCl (1.5 mL) slowly at room temperature. Sodium nitrite (620 mg, 8.98 mmol) was then added slowly at room temperature. THF (3 mL) was added to aid solubility and the reaction was stirred at room temperature overnight. To the above solution was added 10% potassium carbonate (~7 mL) until the pH was ~9. The material was extracted with DCM and washed with water. The organic layer was dried over $Na_2SO_4$, filtered, and concentrated to a tan powder (720 mg, 78%). $^1$H NMR, 400 MHz, $CDCl_3$: 7.41 (1H, m, br), 7.78 (1H, dd, J=7.6 Hz, J=2.4 Hz), 8.61 (1H, dd, J=9.2 Hz, J=4.4 Hz). $^{19}$F NMR. $CDCl_3$: −109.15 (1F, m).

Step 2: Compound 7 (600 mg, 3.9 mmol) was dissolved in oleum (60 mL). NBS (1.5 g, 8.6 mmol) was added in one portion and the reaction mixture was heated to 60° C. overnight. The solution was then cooled to room temperature and poured over 500 mL ice water. The product was extracted with DCM and washed with $H_2O$ until the $H_2O$ layer was neutral. The organic layer was dried over $Na_2SO_4$, filtered, and concentrated to yield a tan powder as the compound 3 (950 mg, 80%), which was directly used in the next step without further purification. $^1$H NMR, 400 MHz, $CDCl_3$. 7.67 (1H, d, J=8 Hz).

Step 3: Compound 8 (600 mg, 1.92 mmol), 4-(2-decyltetradecyl)-2-trimethylstannyl thiophene (2.47 g, 4.23 mmol), $Pd_2dba_3$ (70 mg, 0.08 mmol), and tri(2-furyl)phosphine (70 mg, 0.31 mmol) were added to an air-free flask which was then purged and back-filled 4 cycles with vacuum/Ar. Under Ar, anhydrous THF (50 mL) was added via syringe and the solution was stirred at 80° C. for 16 h. Upon cooling to room temperature, the reaction mixture was concentrated in vacuo. The residue was purified by column chromatography on silica gel (hexanes), yielding a yellow solid as compound 9 (650 mg, 34%). $^1$H NMR, 400 MHz, $C_2D_2Cl_4$. 0.88 (12H, t, J=6.8 Hz), 1.25 (80H, m, br), 1.69 (2H, m, br), 2.64 (4H, d, J=6.4 Hz), 7.16 (2H, d, J=11.6 Hz), 7.43 (1H, s), 7.73 (1H, d, J=12 Hz), 7.99 (1H, s).

Step 4: Compound 9 (400 mg, 0.40 mmol) was dissolved in a mixture of THF (10 mL) and acetic acid (1 mL) under nitrogen at room temperature. NBS (160 mg, 0.89 mmol) was added in one portion. The resulting mixture was stirred overnight and the product was precipitated with MeOH/water (1:1, 20 mL). The precipitate was washed with methanol and this crude product was recrystallized from ethyl acetate (about 5 mL) in the fridge, yielding a yellow solid as the product (430 mg, 86%). $^1$N NMR, 400 MHz, $CDCl_3$. 0.87 (12H, t, J=6.8 Hz), 1.24 (80H, m, br), 1.74 (2H, m, br), 2.57 (4H, d, J=8.8 Hz), 7.25 (1H, d, J=8 Hz), 7.63 (1H, d, J=12 Hz), 7.82 (1H, s).

Step 5: Compound 10 (100.0 mg, 0.079 mmol), 5,5'-bis(trimethylstannyl)-2,2'-bithiophene (39.4 mg, 0.079 mmol), $Pd_2dba_3$ (3.0 mg, 0.003 mmol), $tol_3P$ (3.1 mg, 0.01 mmol) were placed in a Schlenk flask. The system was vacuumed and back-filled with argon four times, before anhydrous chlorobenzene (10 mL) was added via syringe. The resulting mixture was warmed and stirred at 90° C. for 18 h. The reaction was cooled to room temperature and precipitated in methanol (50 mL). The crude product was collected by filtration, washed with methanol, and subject to Soxhlet extraction under nitrogen with methanol (16 h), ethyl acetate (16 h), and hexanes (16 h). The polymer product was extracted into chlorobenzene (100 mL), and the extract was precipitated in methanol (100 mL). The precipitate was collected by filtration, washed with methanol, and dried under vacuum to afford a brown solid as the final product P4 (55 mg, 60.4%). Based on cyclic voltammetry (FIG. 8), the energy level of HOMO of P4 is −5.55 eV. The optical band gap from UV-Vis data (FIG. 9) was found to be 1.85 eV. The energy level of LUMO was estimated to be −3.70 eV.

Figure 6:
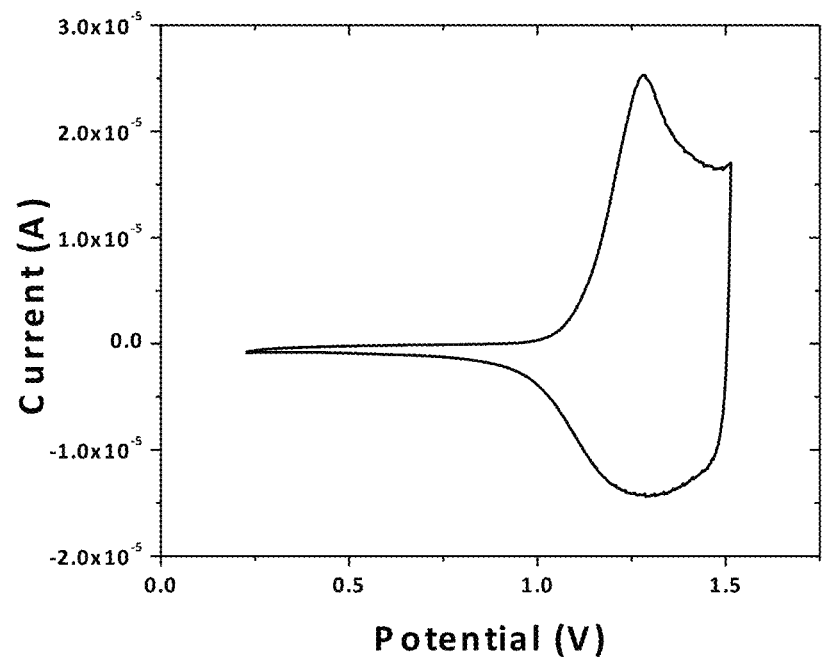
FIG. 6 shows a cyclic voltammogram of yet another exemplary polymer, P4, according to the present teaching in $CH_2Cl_2$.

FIG. 6 shows a cyclic voltammogram of P4 in $CH_2Cl_2$.

Example 6. Synthesis of Polymer P5

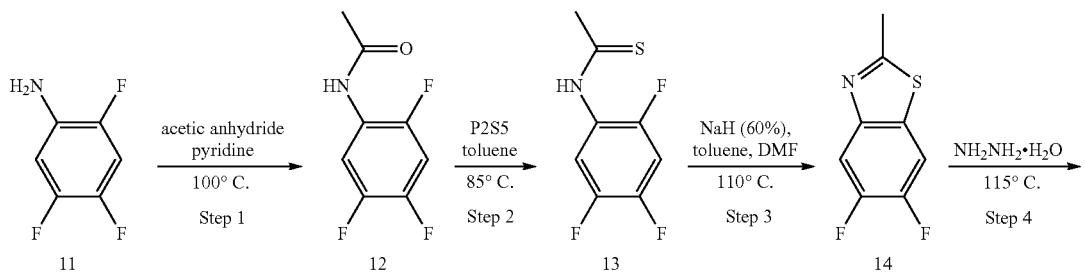

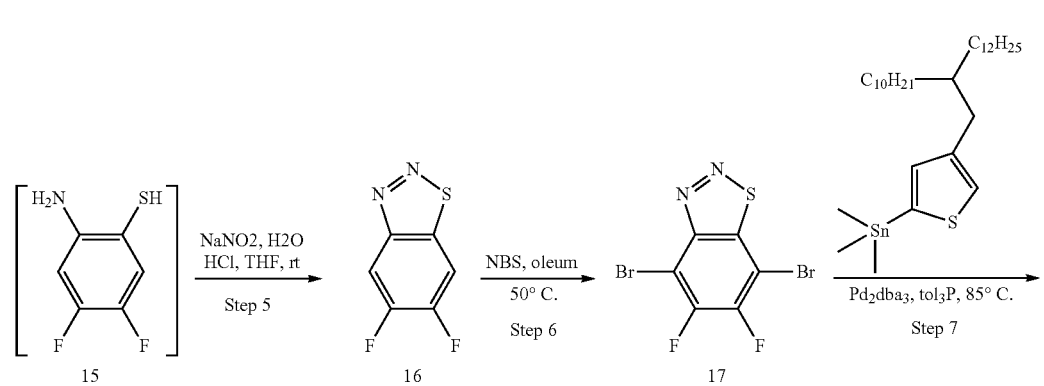

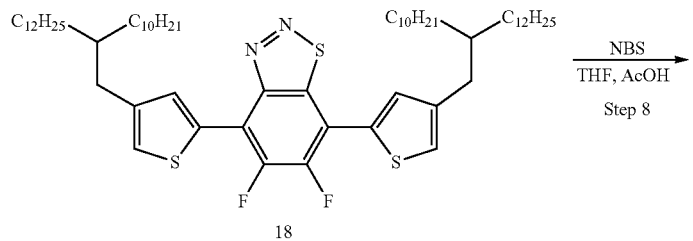

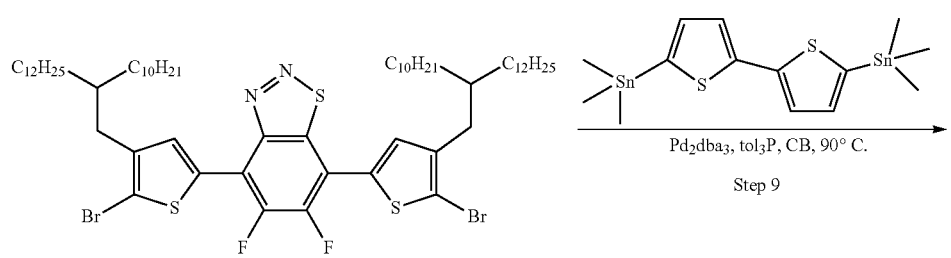

19

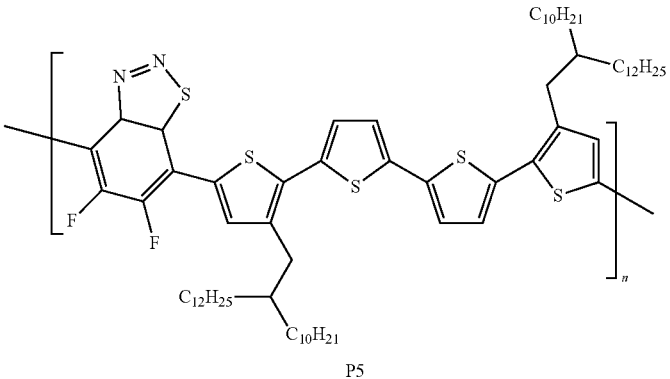

P5

Step 1: A solution of 2,4,5-trifluoroaniline 11 (25 g, 170 mmol) in anhydrous pyridine (14.4 mL, 178 mmol) was treated with acetic anhydride (16.9 mL, 178 mmol) and heated to 120° C. for 2 hours. After cooling to room temperature, the solution was poured into ice-cold water (150 mL). The resulting precipitate was filtered, dissolved in ethyl acetate, dried over anhydrous $Na_2SO_4$, filtered, and concentrated. The residue was dried to give 2,4,5-trifluoroacetanilide (12) (29.63 g, 92%) as a yellow solid. $^1$H NMR (CDCl3, 400 MHz) δ 8.35-8.26 (m, 1H), 7.01-6.93 (m, 1H), 2.22 (s, 3H); $^{19}$F NMR (CDCl3) δ −133.45−−133.54 (m, 1F), −139.56−−139.67 (m, 1F), −140.14−−140.28 (m, 1F).

Step 2: A dried 3-neck, 1 L round-bottom flask was charged with phosphorus pentasulfide (34.08 g, 153 mmol) and diluted with anhydrous toluene (500 mL). Compound 2,4,5-trifluoroacetanilide (12) (29 g, 153 mmol) was added in one portion and the bright yellow suspension was heated to 90° C. for 15 hours. After cooling to room temperature, the reaction was washed with aqueous NaOH (15%, 250 mL). The aqueous phase was extracted with ethyl acetate (200 mL). The organic phases were combined, dried over anhydrous $Na_2SO_4$, filtered, and concentrated. The crude product was passed through a silica gel column prepared with chloroform and concentrated to give 2,4,5-trifluorothioacetanilide (13) (23.23 g, 74%) as a yellow solid. $^1$H NMR (CDCl3, 400 MHz) δ 8.69-8.62 (m, 1H), 8.47 (s, 1H), 7.08-7.01 (m, 1H), 2.76 (s, 3H). $^{19}$F NMR (CDCl3) δ −128.45−−128.53 (m, 1F), −134.34−−134.45 (m, 1F), −139.39−−139.54 (m, 1F).

Step 3: A flame-dried, 1 L round-bottom flask with a condenser was charged with sodium hydride (5.15 g, 129 mmol, 60% by wt) and diluted with anhydrous toluene (500 mL). The suspension was treated with 2,4,5-trifluorothioacetanilide (13) (22 g, 107 mmol) in one portion and stirred at room temperature for 2 hours. Dimethylformamide (100 mL) was added and the reaction was heated to reflux at 110° C. for 3 hours. The solution was cooled to room temperature and washed with brine (500 mL). The aqueous phase was extracted with ethyl acetate (300 mL). The organic phases were combined, dried over anhydrous $Na_2SO_4$, filtered, and concentrated. The crude product was passed through a silica gel column prepared with chloroform and concentrated to give 5,6-difluoro-2-methylbenzothiazole (14) (16.54 g, 83%) as a yellow solid. $^1$H NMR (CDCl3) δ 7.73 (dd, 1H, J=7.08 Hz, J=10.48 Hz), 7.59 (dd, 1H, J=7.52 Hz, J=8.96 Hz), 2.83 (s, 3H); $^{19}$F NMR (CDCl3) δ −138.43−−138.54 (m, 1F), −139.35−−139.45 (m, 1F).

Steps 4 and 5: A solution of 5,6-difluoro-2-methylbenzothiazole (14) (10 g, 54 mmol) and hydrazine monohydrate (40 mL, 820 mmol) was stirred for 2 days at 115° C. The reaction was cooled to room temperature, neutralized to pH 7 with concentrated HCl solution, and extracted with dichloromethane (4×250 mL). The organic phases were combined, dried over anhydrous $Na_2SO_4$, and concentrated. The yellow oil crystallized overnight to give 4,5-difluoro-2-aminothiophenol (15) (7.52 g), which was mixed with water (100 mL). A solution of 12M HCl (26 mL) was added slowly at room temperature, followed by addition of sodium nitrite (4.82 g, 70 mmol). Tetrahydrofuran (50 mL) was added to facilitate the dissolution of solids and the reaction was stirred at room temperature overnight. The reaction mixture was neutralized with saturated aqueous $K_2CO_3$ (200 mL) and extracted with dichloromethane (2×300 mL). The organic phases were combined, dried over anhydrous $Na_2SO_4$, and concentrated to give the product (16) (6.59 g, 82%). 1H NMR (CDCl3, 400 MHz) δ 8.40 (dd, 1H, J=6.92 Hz, J=9.12 Hz), 7.88 (dd, 1H, J=7.16 Hz, J=8.08 Hz); 19F NMR (CDCl3) δ −129.58−−129.67 (m, 1F), −134.10−−134.19 (m, 1F).

Step 6: Compound 16 (550 mg, 3.2 mmol) was dissolved in oleum (40 mL). NBS (1.2 g, 7.0 mmol) was added in one portion and the reaction mixture was heated to 50° C. overnight. The solution was then cooled to rt and poured over 200 mL of ice water. Precipitation was observed and the suspension was filtered. The brown precipitate was then dissolved in DCM and flushed through a short pad of $SiO_2$. The solvent was evaporated and the product was dried to a light tan powder as the product (17) (380 mg, 36%), which was directly used for next step without further purifications. $^{19}$F NMR (CDCl$_3$): −120.7 (1F, d, J=17.6 Hz), −124.1 (1F, d, J=21.5 Hz).

Step 7: Compound 17 (370 mg, 1.12 mmol), 4-(2-decyltetradecyl)-2-trimethylstannyl thiophene (1.43 mg, 2.45 mmol), $Pd_2dba_3$ (41 mg, 0.04 mmol), and tri(2-furyl)phosphine (41 mg, 0.18 mmol) were added to an air free flask which was then purged and backfilled with vacuum/argon four times. Under Ar, anhydrous THF (40 mL) was added via syringe and the solution was stirred at 85° C. for 16 h. Upon cooling to rt, the reaction mixture was flushed through a pad of $SiO_2$ with the aid of DCM and then concentrated in vacuo. The concentrated solid was then recrystallized in 10 mL of heptane in the freezer, leading to a yellow solid as the product (18) (407.6 mg, 36%). $^1$H NMR, (400 MHz, $CD_2Cl_2$): 8.15 (1H, s). 7.48 (1H, d, J=6 Hz), 7.28 (1H, s), 7.20 (1H, s), 2.67 (2H, dd J=10.4 Hz, J=6.8), 1.71 (2H, m, br), 1.32 (2H, m, br), 1.26 (80H, m, br), 0.87 (12H, t, J=6.0 Hz). $^{19}$F NMR (CD$_2$Cl$_2$): −131.9 (1F, d, J=17.3 Hz), −134.3 (1F, d, J=17.3 Hz).

Step 8: Compound 19 (400 mg, 0.40 mmol) was dissolved in a mixture of THF (10 mL) and acetic acid (1 mL) at RT. NBS (155 mg, 0.87 mmol) was added in one portion. The resulting mixture was stirred overnight and the product was extracted with DCM and washed with water. The organic layer was dried over anhydrous Na$_2$SO$_4$, filtered and concentrated. The solid was then subjected to a short hexanes column to yield a yellow solid as the product (20) (322 mg, 70%). $^1$H NMR (400 MHz, CD$_2$Cl$_2$): 8.03 (1H, s). 7.33 (1H, s), 2.62 (4H, dd, J=8.8 Hz, J=7.2), 1.26 (82H, m, br), 0.87 (12H, t, J=6.0 Hz). $^{19}$F NMR, 400 MHz, CD$_2$Cl$_2$. −131.4 (1F, d, J=16.9 Hz), −133.9 (1F, d, J=9.4 Hz).

Step 9: Compound 20 (150 mg, 0.13 mmol), 5,5'-bis (trimethylstannyl)-2,2'-bithiophene (63.2 mg, 0.13 mmol), Pd$_2$dba$_3$ (4.6 mg, 0.005 mmol), tol$_3$P (6.2 mg, 0.02 mmol) were placed in a Schlenk flask. The system was vacuumed and backfilled with argon four times, before anhydrous chlorobenzene (12 mL) was added via syringe. The resulting mixture was warmed and stirred at 90° C. for 18 h. The reaction was cooled to rt and precipitated in methanol (100 mL). The crude product was collected by filtration, washed with methanol, and subject to Soxhlet extraction under nitrogen with methanol (10 h), ethyl acetate (13 h), and hexanes (9 h). Finally, the polymer product was extracted into chloroform (120 mL), and the extract was precipitated in methanol (200 mL). The precipitate was collected by filtration, washed with methanol, and dried under vacuum to afford a dark-blue solid as the final product P5 (135 mg). Based on CV, the energy level of HOMO of P5 is −5.74 eV. The optical band gap from UV-Vis was found to be 1.80 eV. The energy level of LUMO was estimated to be −3.94 eV.

Figure 7:
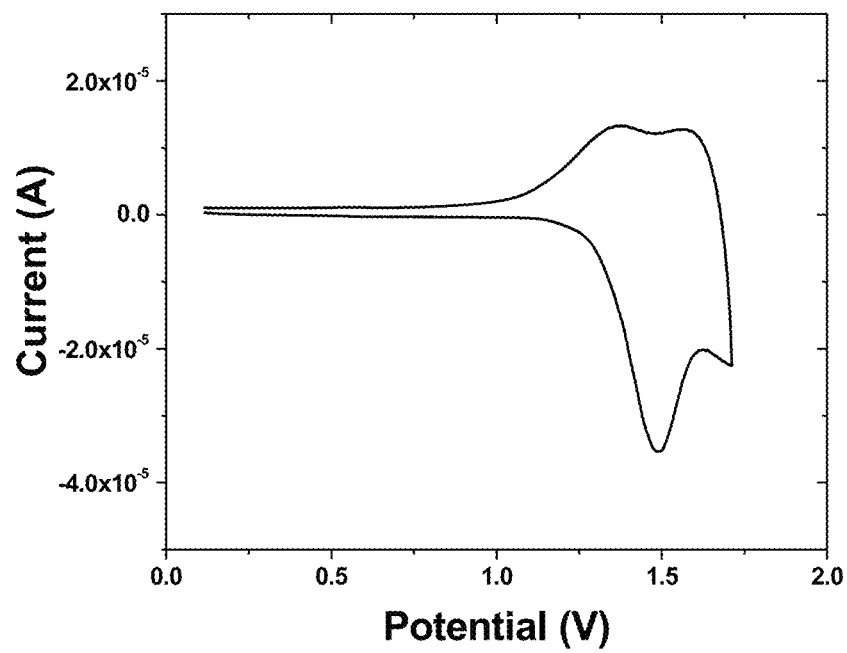
FIG. 7 shows a cyclic voltammogram of yet another exemplary polymer, P5, according to the present teaching in $CH_2Cl_2$.

FIG. 7 shows a cyclic voltammogram of P5 in CH$_2$Cl$_2$.

Figure 8:
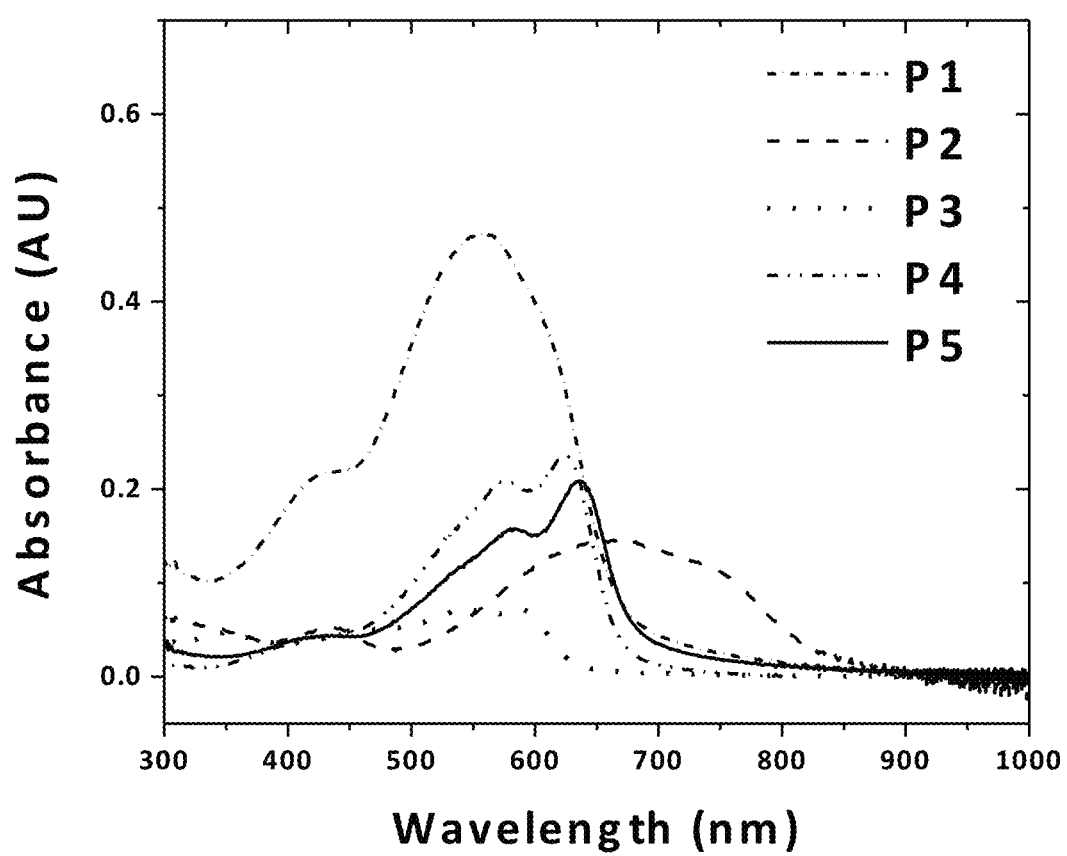
FIG. 8 compares the optical absorption spectra of exemplary polymers P1, P2, P3, P4 and P5 as spin-coated thin films.

FIG. 8 compares the optical absorption spectra of P1, P2, P3, P4 and P5 as spin-coated thin films. Table 1 below summarizes the characterization data of P1, P2, P4 and P5.

TABLE 1

Summary of Characterization Data of P1, P2, P4 and P5.

| Polymer | HOMO (eV) | LUMO (eV) | Optical Band Gap (eV) |
|---|---|---|---|
| P1 | −5.62 | −3.77 | 1.85 |
| P2 | −4.82 | −3.33 | 1.49 |
| P4 | −5.55 | −3.70 | 1.85 |
| P5 | −5.74 | −3.94 | 1.80 |

Example 7. Fabrication of Organic Thin Film Transistor Devices

Top-gate bottom-contact TFT devices were fabricated using P1, P4 and P5 as the semiconductor layer. Eagle™ 100 glass (Corning Inc.) coated with a buffer layer were used as device substrates. Prior to the deposition of the semiconductor layer, 500 Å gold source and drain electrodes were thermally evaporated through a stencil mask to define the transistor channel. Polymers P1, P4 and P5 were dissolved in 1,2-dichlorobenzene at a concentration of 6 mg/ml. The formulations were spin-coated onto the substrates at 1000 rpm for 60 sec, and baked on a 100° C. hot plate for 5 minutes to form semiconductor films approximately 30-100 nm in thickness. The TFT devices were completed by spin-coating a 400-700 nm thick Cytop (809M, AGC) layer as dielectric, followed with thermal evaporation of 500 Å gold gate electrode. The TFT devices were tested in the dark in a probe station (Signatone) ambient environment using Keithley 4200 two source electrometer.

Figure 9:
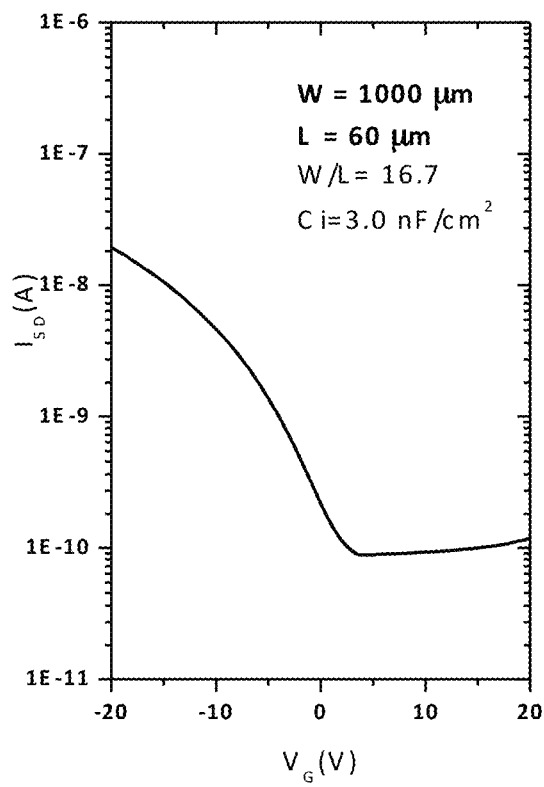
FIG. 9 shows the transfer characteristics of a representative organic thin film transistor incorporating P1 as the semiconductor layer.
Figure 10:
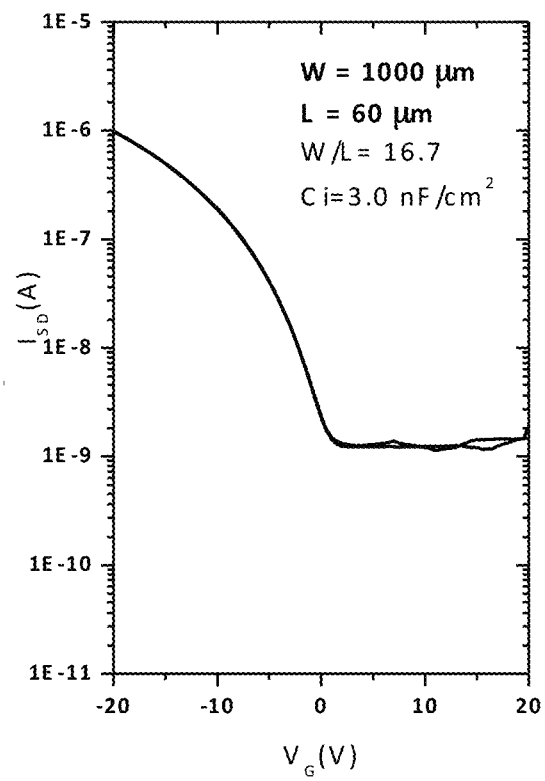
FIG. 10 shows the transfer characteristics of a representative organic thin film transistor incorporating P4 as the semiconductor layer.
Figure 11:
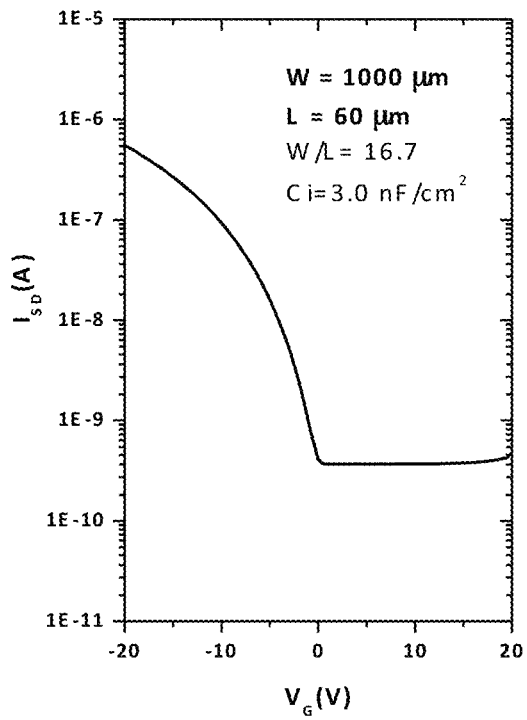
FIG. 11 shows the transfer characteristics of a representative organic thin film transistor incorporating P5 as the semiconductor layer.
Figure 12:
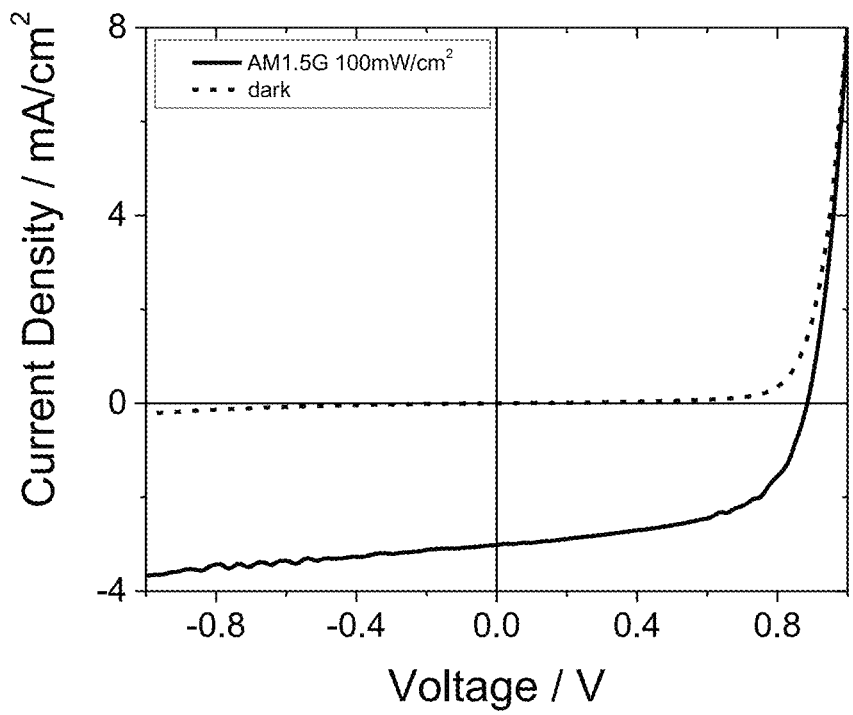
FIG. 12 shows the current-voltage scan of a representative organic solar cell incorporating a donor-acceptor blend material (P1 as the donor, C70PCBM as the acceptor) as the bulk-heterojunction photoactive layer.
Figure 13:
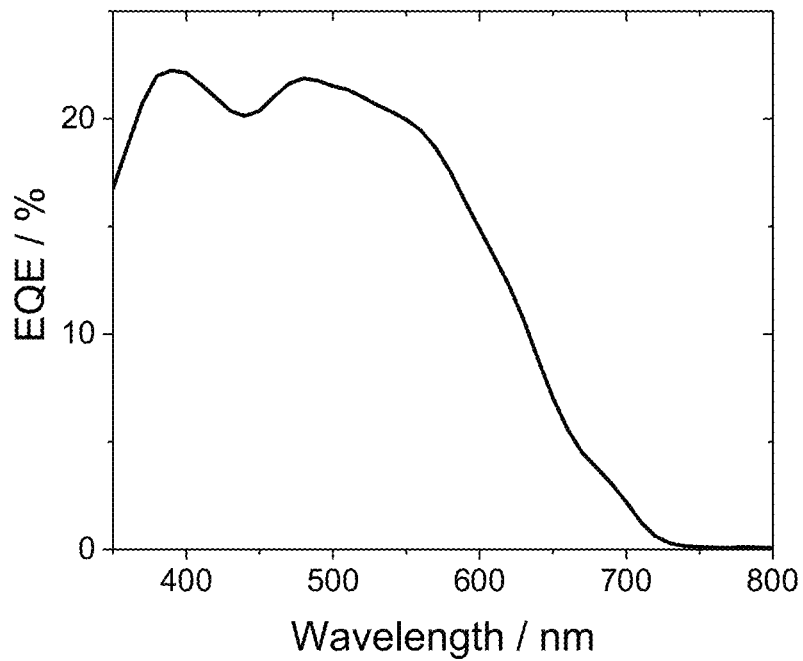
FIG. 13 plots the external quantum efficiency of a representative organic solar cell incorporating a donor-acceptor blend material (P1 as the donor, C70PCBM as the acceptor) as the bulk-heterojunction photoactive layer.
Figure 14:
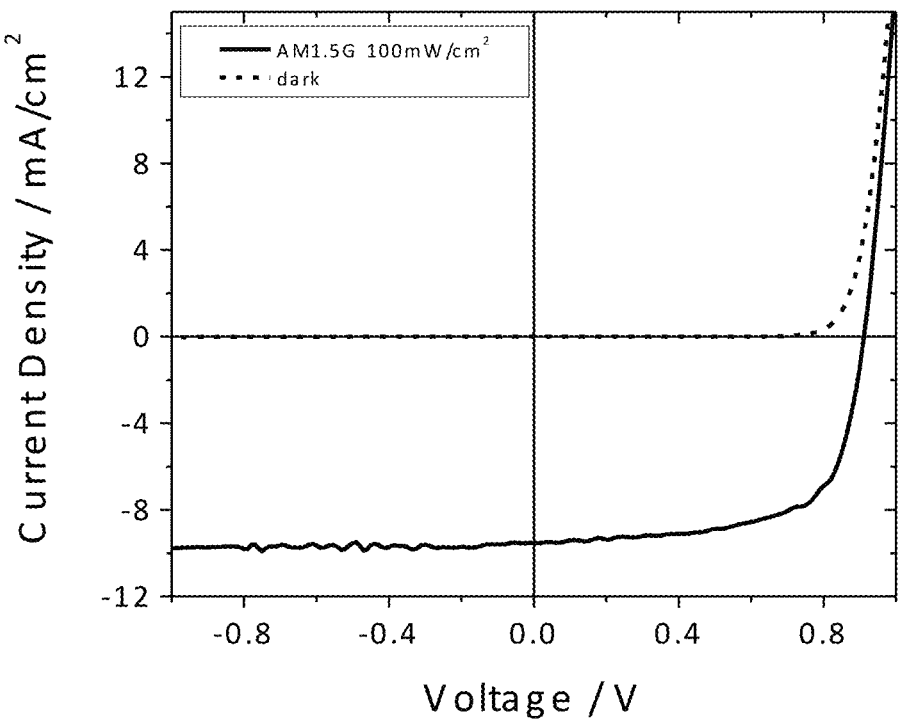
FIG. 14 shows the current-voltage scan of a representative organic solar cell incorporating a donor-acceptor blend material (P4 as the donor, C70PCBM as the acceptor) as the bulk-heterojunction photoactive layer.
Figure 15:
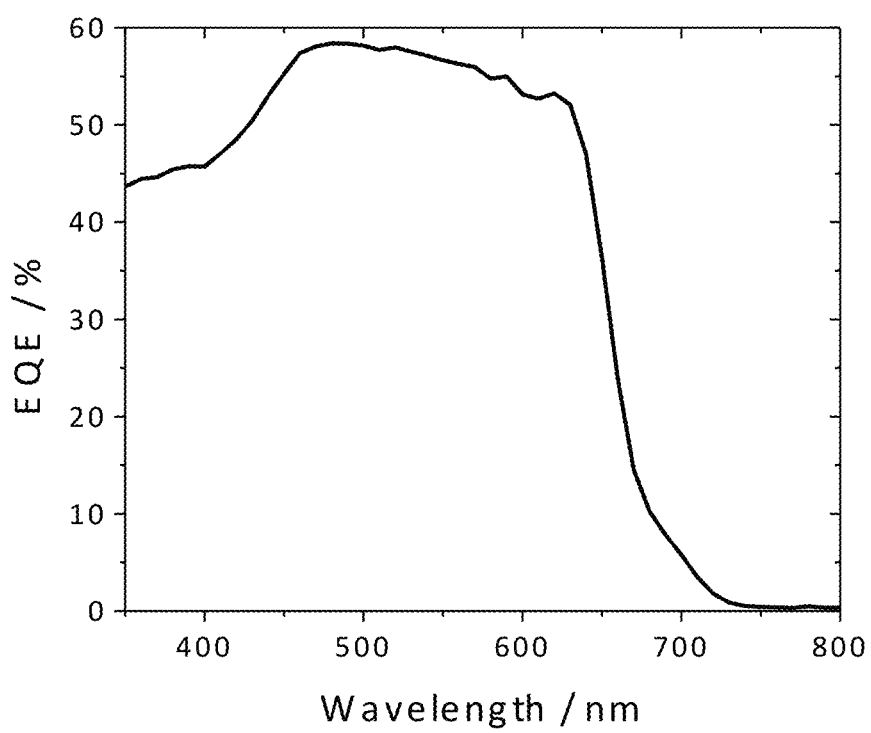
FIG. 15 plots the external quantum efficiency of a representative organic solar cell incorporating a donor-acceptor blend material (P4 as the donor, C70PCBM as the acceptor) as the bulk-heterojunction photoactive layer.

FIGS. 9, 10 and 11 show the transfer characteristics of a representative organic thin film transistor incorporating as the semiconductor layer polymer P1, P4, or P5, respectively. Table 2 summarizes the key device data.

TABLE 2

Summary of mobilities and threshold voltages for TFTs based on P1, P4 and P5.

| Semiconductors | Average mobility [cm$^2$/Vs] | $V_{on}$ (V) |
|---|---|---|
| P1 | 0.0019 | 1.5-3.0 |
| P4 | 0.14 | 0.5 |
| P5 | 0.08 | 0.0-0.5 |

Example 8. Fabrication of Organic Solar Cells

The polymer semiconductor (P1, P4 or P5) and C70PCBM were dissolved in a CHCl$_3$:DCB solvent mixture (9:1 by volume). Diiodooctane (2% by volume) were added to the solution before spin-coating the active layers. Conventional OPV devices were fabricated by evaporating 8 nm of MoO$_3$ onto pre-cleaned ITO substrates. Active layers were spin-coated in a N$_2$ glove box. Finally, 0.6 nm of LiF and 100 nm of Al were evaporated as the top electrode under a vacuum of about 10$^{-6}$ mbar. Devices were encapsulated using a blanket of EPOTEK OG116-31 UV-curable epoxy (Epoxy Technologies) and a glass cover slip.

The photovoltaic characteristics of encapsulated devices were tested in air. The current-voltage (I-V) curves were obtained by a Keithley 2400 source-measure unit. The photocurrent was measured under simulated AM1.5G irradiation (100 mW cm$^{-2}$) using a Xenon lamp-based solar simulator (Newport 91160A 300W Class-A Solar Simulator, 2 inch by 2 inch uniform beam). The light intensity was set using an NREL-calibrated silicon photodiode with a color filter. The external quantum efficiency was measured using Newport's QE setup. Incident light from a Xenon lamp (300 W) passing through a monochromator (Newport, Cornerstone 260) was focused on the active area of the cell. The output current was measured using a current pre-amplifier (Newport, 70710QE) and a lock-in amplifier (Newport, 70105 Dual channel Merlin). A calibrated silicon diode (Newport 70356) was used as the reference.

The JV characteristics for typical devices are summarized in Table 3. FIGS. 12-15 illustrate the JV scan and EQE curve for representative devices.

TABLE 3

JV characteristics of P1: C70PCBM, P4: C70PCBM and P5: C70PCBM blend devices measured under simulated AM1.5 (100 mW/cm$^2$)

| Polymer | $V_{oc}$ [V] | $J_{sc}$ [mA/cm$^2$] | FF [%] | PCE [%] |
|---|---|---|---|---|
| P1 | 0.88 | 3.1 | 56.9 | 1.5 |
| P4 | 0.91 | 9.4 | 66.4 | 5.7 |
| P5 | 0.92 | 10.7 | 62.4 | 6.1 |

All publications, including but not limited to patents and patent applications, cited in this specification are herein incorporated by reference as if each individual publication were specifically and individually indicated to be incorporated by reference herein as though fully set forth.

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

What is claimed is:

1. An organic thin film transistor comprising a substrate, a thin film semiconductor, a dielectric layer, a gate electrode, and source and drain electrodes, wherein the thin film semiconductor comprises a polymer having a first repeating unit $M_1$, said polymer having a degree of polymerization (n) ranging from 3 to 1,000, wherein $M_1$ comprises one or more divalent benzo[d][1,2,3]thiadiazole units represented by formula (I):

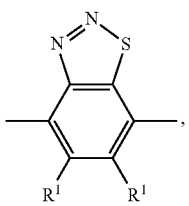
(I)

wherein each $R^1$ independently is selected from the group consisting of H, F, Cl, Br, I, —CN, —NO$_2$, CH$_3$, OCH$_3$, CF$_3$, and a phenyl group, provided at least one $R^1$ is selected from F, Cl, Br, I, —CN, —NO$_2$, and CF$_3$.

2. The organic thin film transistor of claim 1, wherein said polymer has a degree of polymerization (n) ranging from 8 to 100.

3. The organic thin film transistor of claim 1, wherein $M_1$ is selected from the group consisting of:

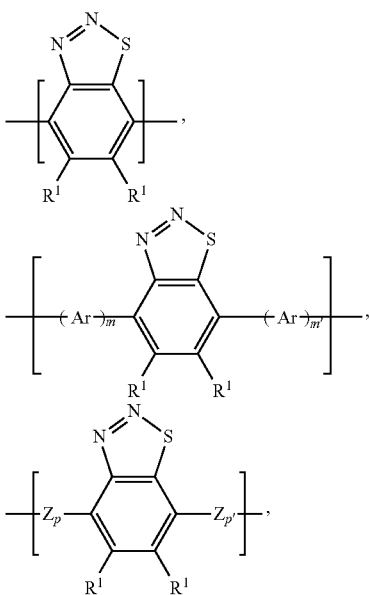

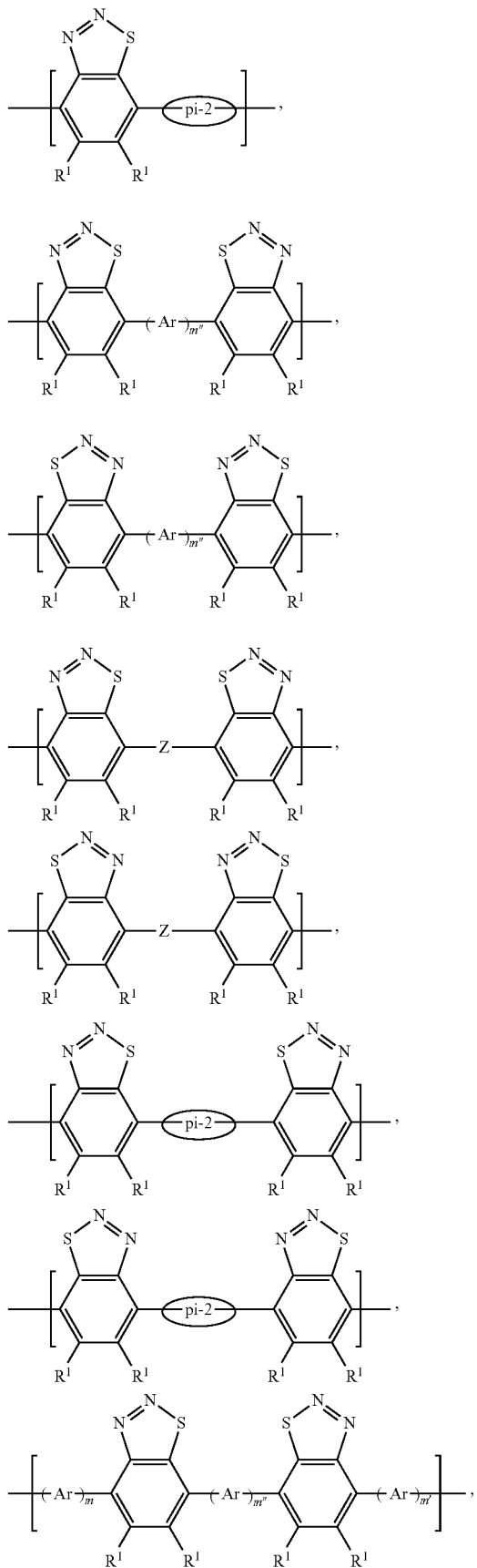

-continued

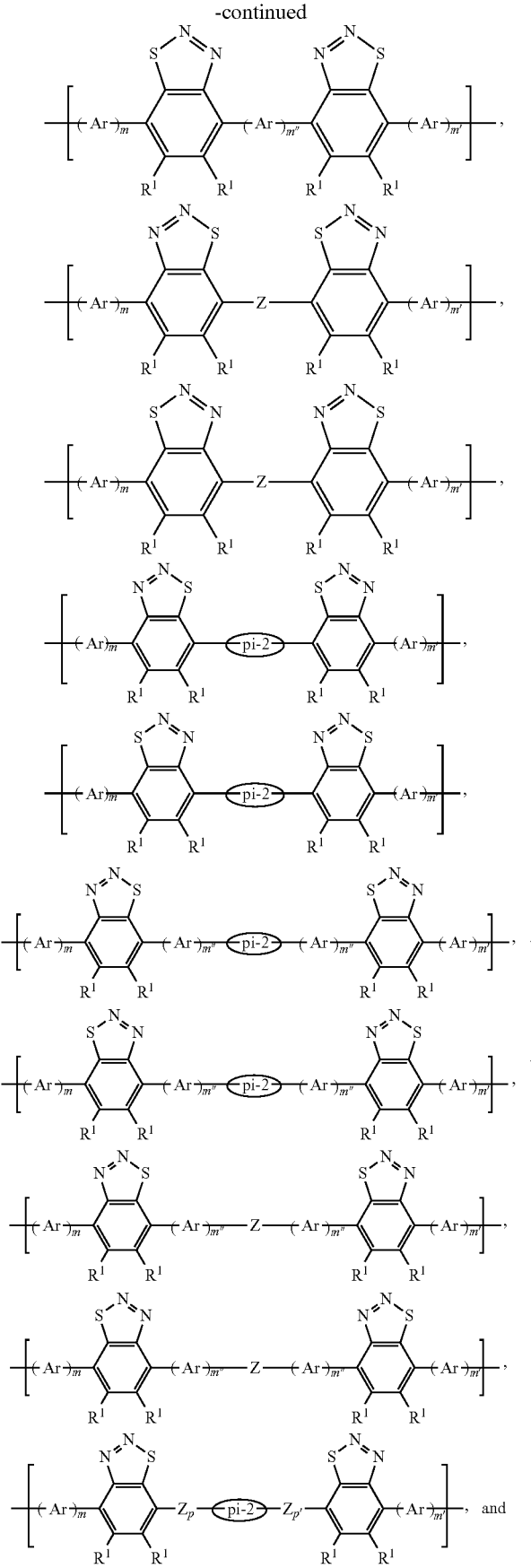

-continued

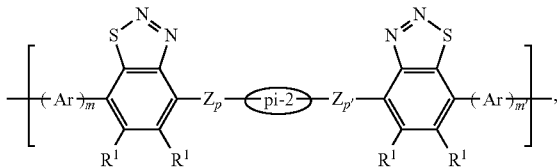

wherein:
pi-2 is an optionally substituted conjugated polycyclic moiety;
Ar, at each occurrence, is independently an optionally substituted 5- or 6-membered aryl or heteroaryl group;
Z is a conjugated noncyclic linker;
m and m' independently are 0, 1, 2, 3, 4, 5 or 6, provided that at least one of m and m' is not 0;
m" is 1, 2, 3, 4, 5 or 6; and
p and p' independently are 0 and 1, provided that at least one of p and p' is 1.

4. The organic thin film transistor of claim 3, wherein pi-2 is an optionally substituted $C_{8-26}$ aryl group or 8-26 membered heteroaryl group.

5. The organic thin film transistor of claim 4, wherein pi-2 is selected from the group consisting of:

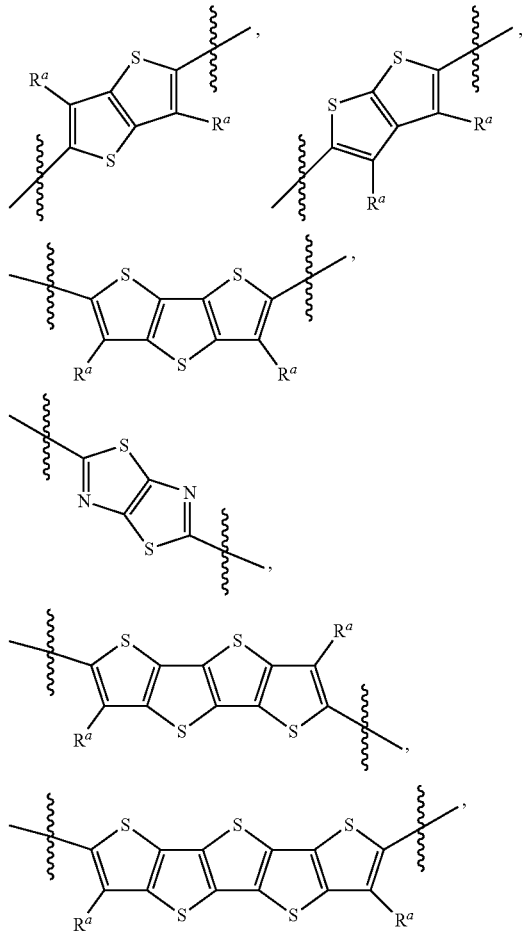

91
-continued
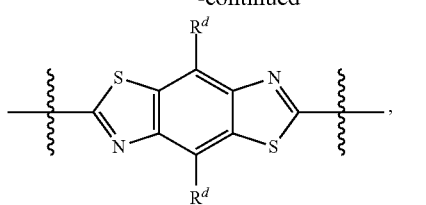
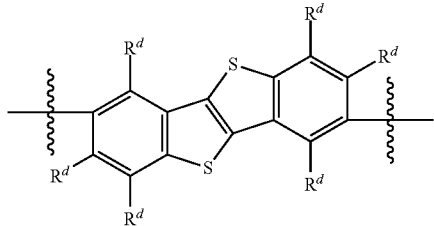
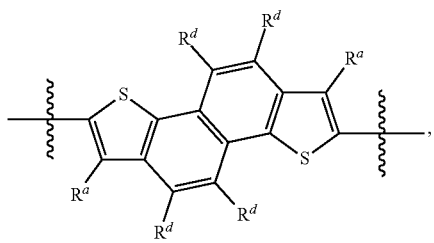
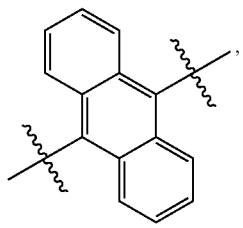
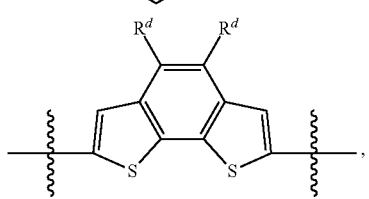
,
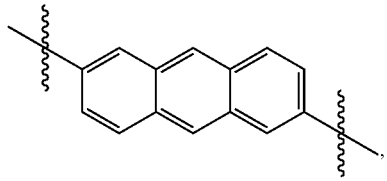
,
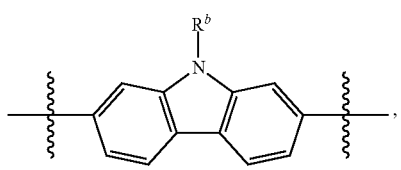
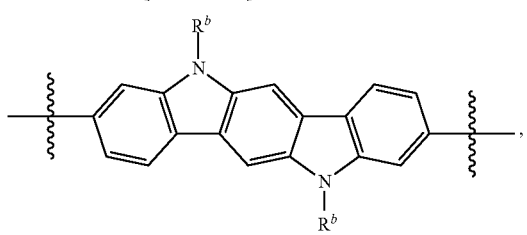
,
92
-continued
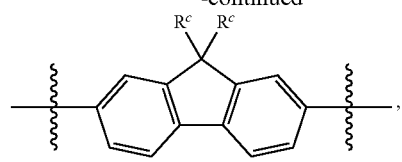
,
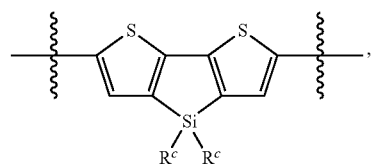
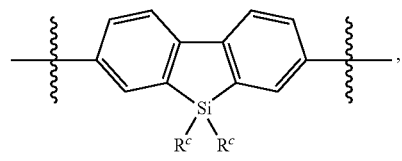
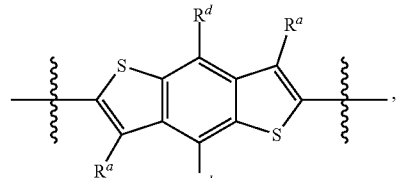
,
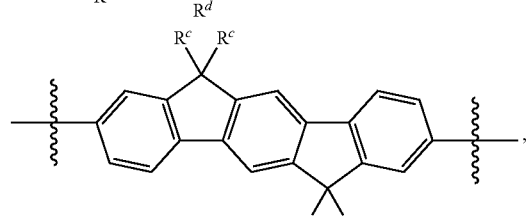
,
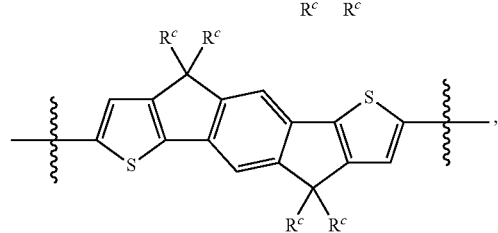
,
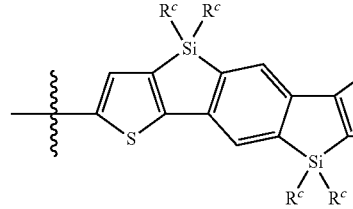
,
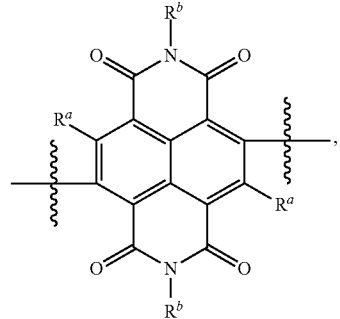

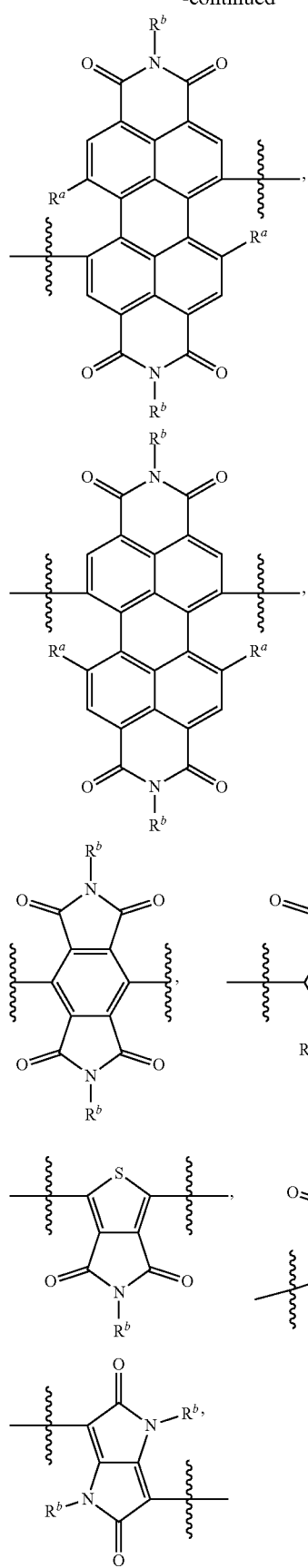
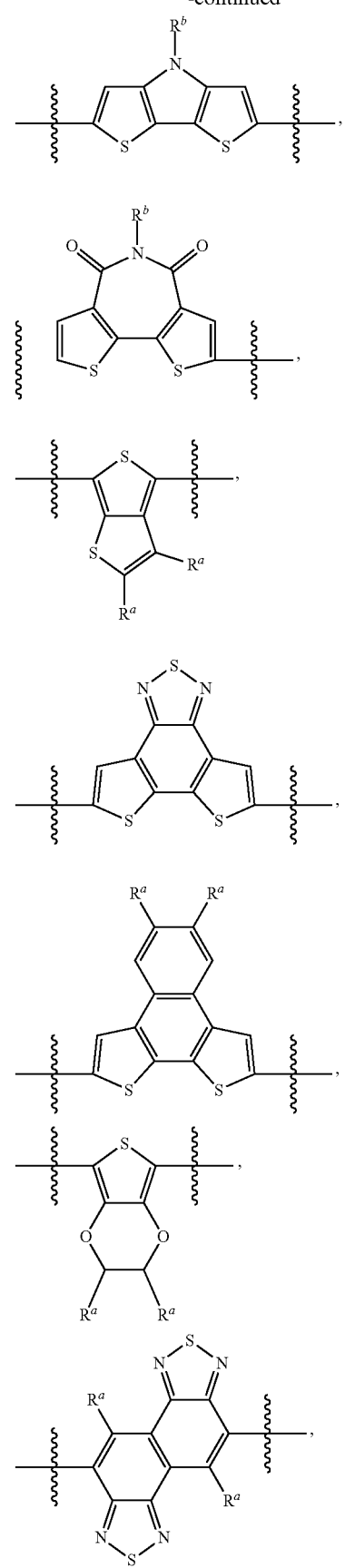

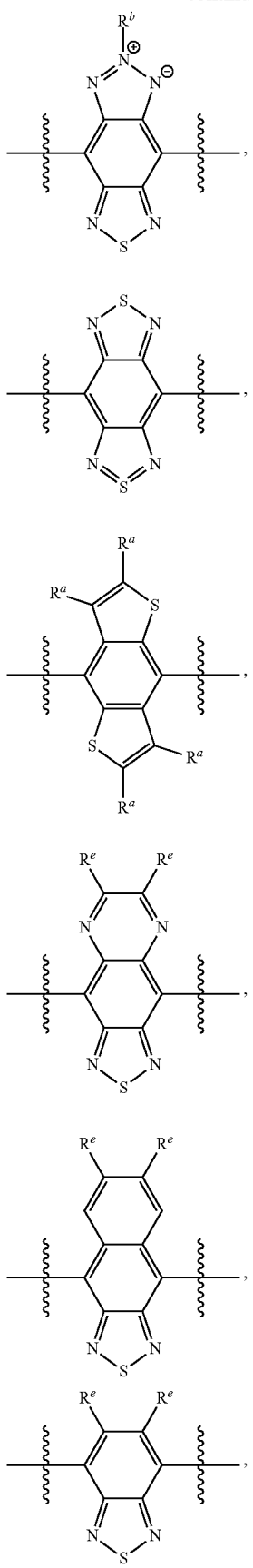

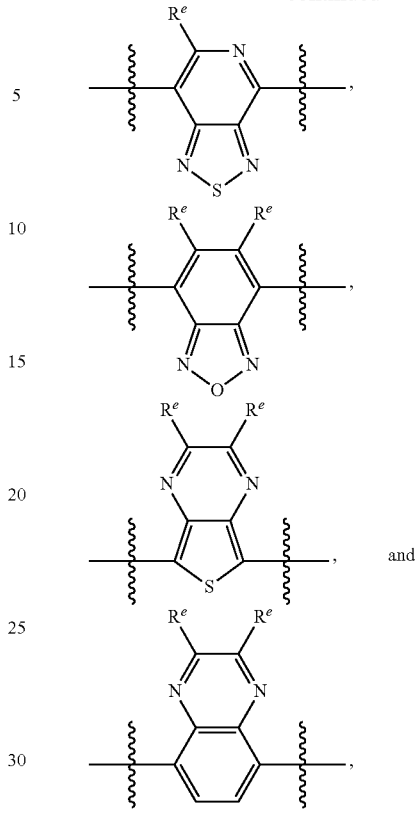

and wherein:
R$^a$ is selected from the group consisting of H, F, Cl, —CN, R, —OR, —SR, —C(O)R, —OC(O)R, and —C(O)OR;
R$^b$ is selected from the group consisting of H, R, and -L-R$^f$;
R$^c$ is H or R;
R$^d$ is selected from the group consisting of H, F, Cl, —CN, R, —OR, —SR, —C(O)R, —OC(O)R, —C(O)OR, and -L-R$^f$;
R$^e$ is selected from the group consisting of H, F, Cl, —CN, R, —OR, —SR, —C(O)R, —OC(O)R, —C(O)OR, and R$^f$;
R$^f$ is a C$_{6-20}$ aryl group or a 5-20-membered heteroaryl group, each optionally substituted with 1-8 groups independently selected from the group consisting of F, Cl, —CN, R, —OR, and —SR;
L is selected from the group consisting of —O—, —S—, —C(O)—, —OC(O)—, —O(O)O—, and a covalent bond; and
R is selected from the group consisting of a C$_{1-40}$ alkyl group, a C$_{1-40}$ haloalkyl group, a C$_{2-40}$ alkenyl group, and a C$_{2-40}$ alkynyl group.

6. The organic thin film transistor of claim 3, wherein Ar in (Ar)$_m$, (Ar)$_{m'}$, and (Ar)$_{m''}$ is represented by:

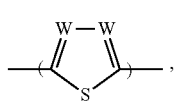

wherein each W independently is selected from the group consisting of N, CH, and CR$^4$, wherein R$^4$ is selected from the group consisting of F, Cl, —CN, $R^2$, $OR^2$, $SR^2$, $C(O)R^2$, $OC(O)R^2$, and $C(O)OR^2$, and wherein $R^2$ is selected from the group consisting of a $C_{1-40}$ alkyl group, a $C_{2-40}$ alkenyl group, a $C_{2-40}$ alkynyl group, and a $C_{1-40}$ haloalkyl group.
7. The organic thin film transistor of claim 6, wherein $(Ar)_m$, $(Ar)_{m'}$, and $(Ar)_{m''}$ independently are selected from the group consisting of:
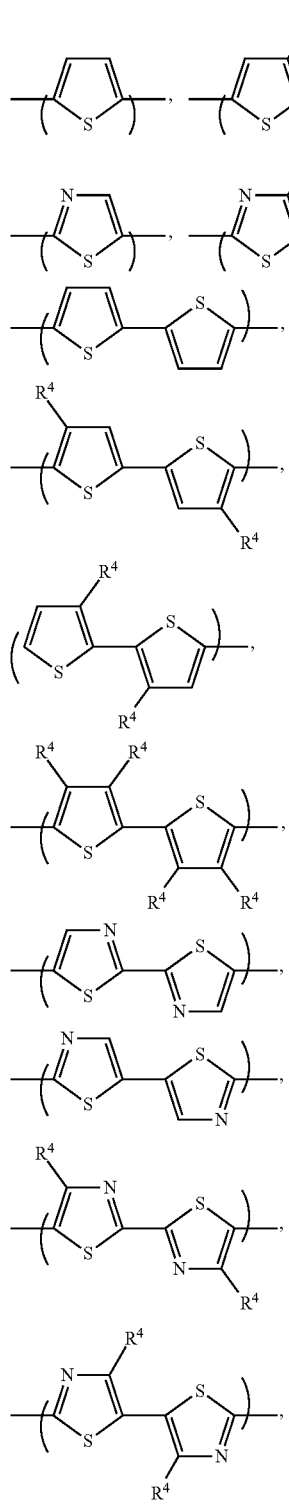
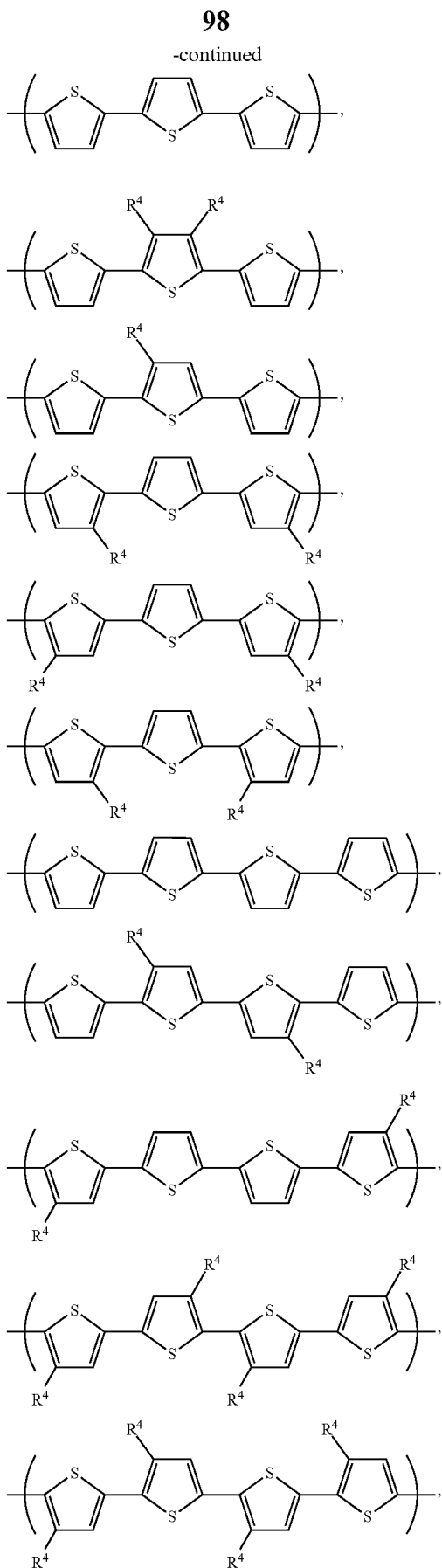

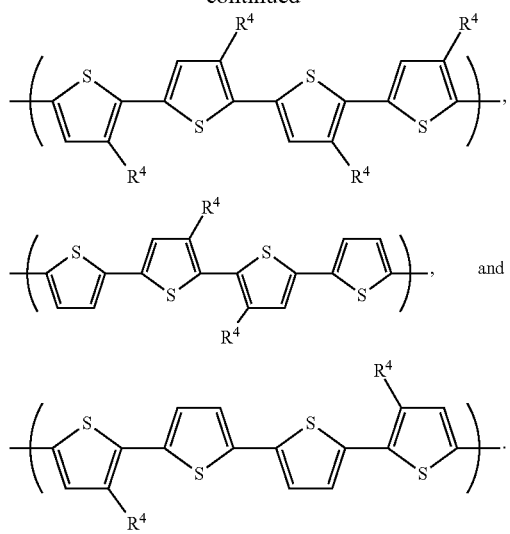

8. The organic thin film transistor of claim 3, wherein Z is selected from the group consisting of:

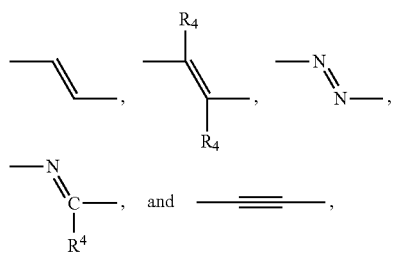

wherein $R^4$ is selected from the group consisting of F, Cl, —CN, $R^2$, $OR^2$, $SR^2$, $C(O)R^2$, $OC(O)R^2$, and $C(O)OR^2$, and wherein $R^2$ is selected from the group consisting of a $C_{1-40}$ alkyl group, a $C_{2-40}$ alkenyl group, a $C_{2-40}$ alkynyl group, and a $C_{1-40}$ haloalkyl group.

9. The organic thin film transistor of claim 3, wherein the polymer further comprises one or more repeating units other than $M_1$, the one or more other repeating units ($M_2$) being selected from the group consisting of:

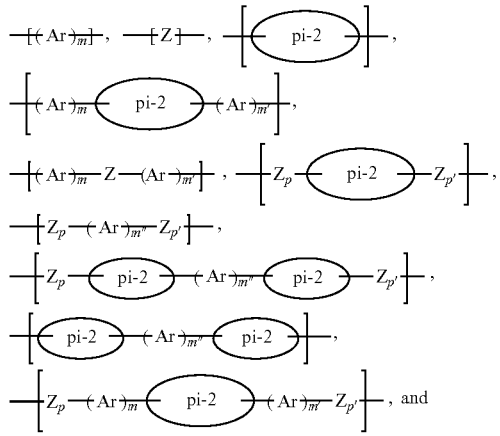

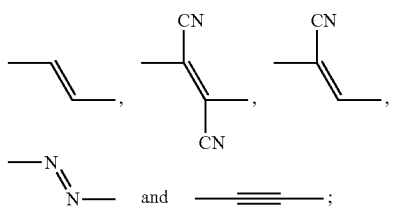

wherein:
pi-2 is an optionally substituted conjugated polycyclic moiety;
Ar, at each occurrence, is independently an optionally substituted 5- or 6-membered aryl or heteroaryl group;
Z is a conjugated noncyclic linker;
m and m' independently are 0, 1, 2, 3, 4, 5 or 6, provided that at least one of m and m' is not 0;
m" is 1, 2, 3, 4, 5 or 6; and
p and p' independently are 0 and 1, provided that at least one of p and p' is 1.

10. The organic thin film transistor of claim 9, wherein:
Z is selected from the group consisting of:

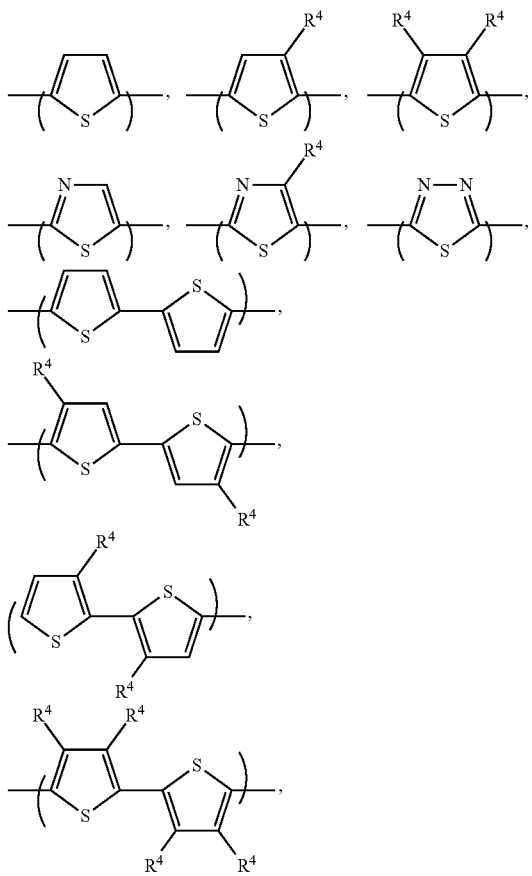

$(Ar)_m$, $(Ar)_{m'}$, and $(Ar)_{m''}$ independently are selected from the group consisting of:

101
-continued
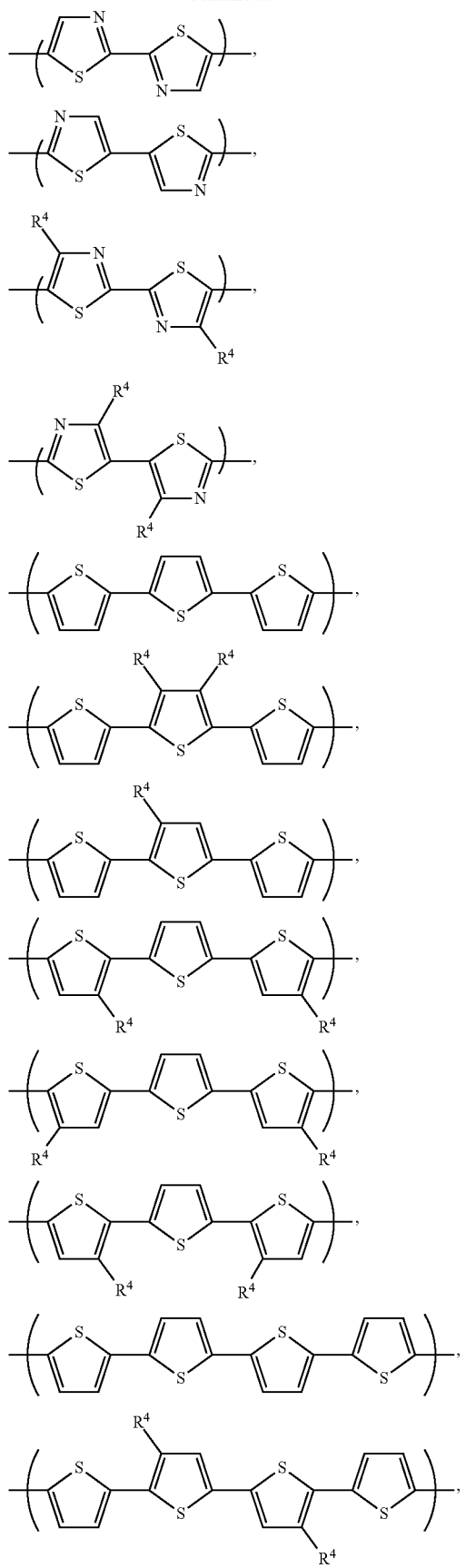
102
-continued
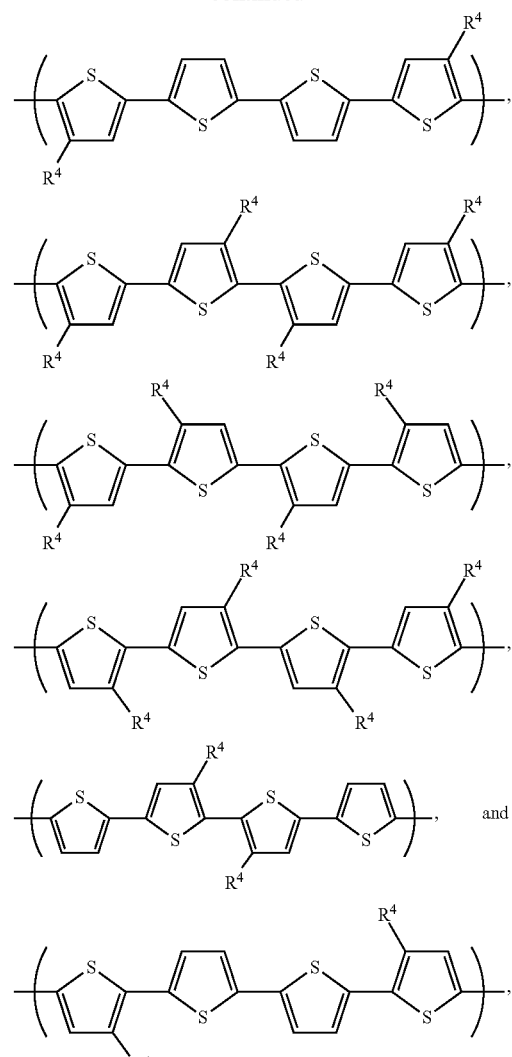
wherein $R^4$ is selected from F, Cl, —CN, $R^2$, $OR^2$, $SR^2$, $C(O)R^2$, $OC(O)R^2$, and $C(O)OR^2$, and wherein $R^2$ is selected from a $C_{1-40}$ alkyl group, a $C_{2-40}$ alkenyl group, a $C_{2-40}$ alkynyl group, and a $C_{1-40}$ haloalkyl group; and
pi-2 is selected from the group consisting of:
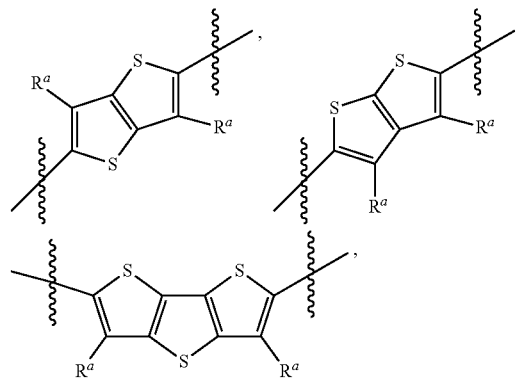

103
-continued
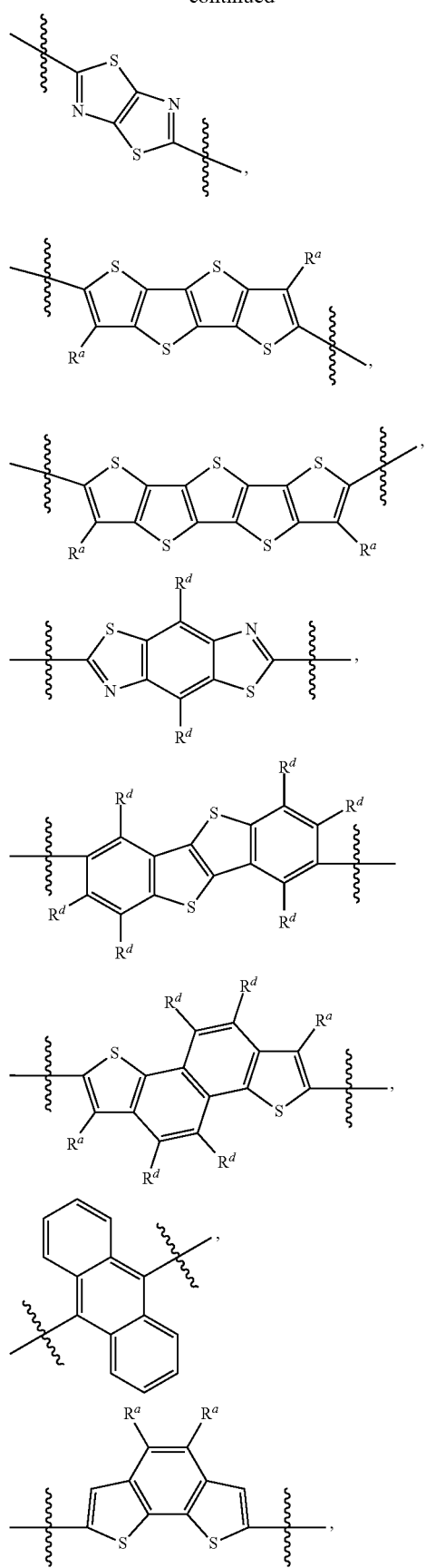
104
-continued
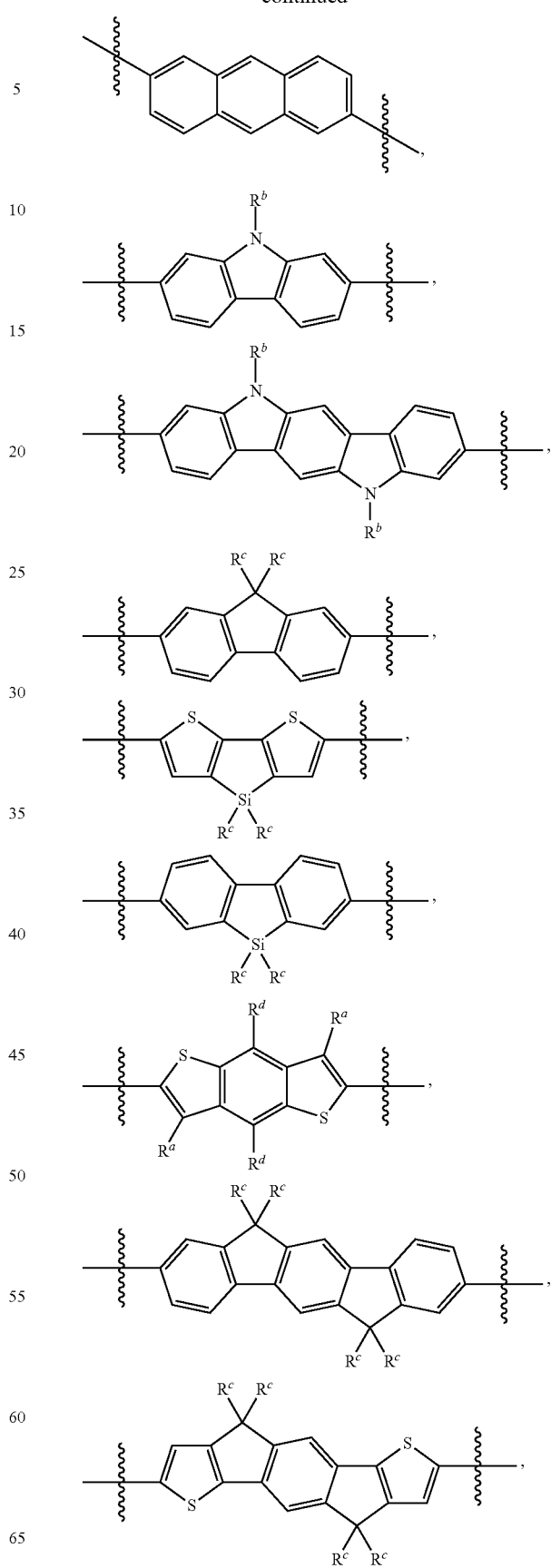

105
-continued
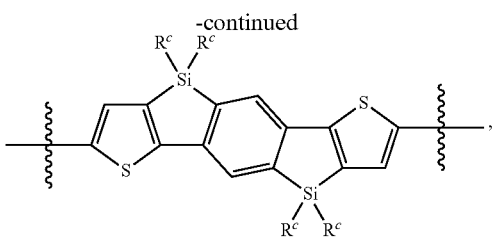
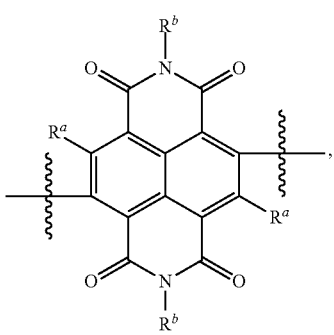
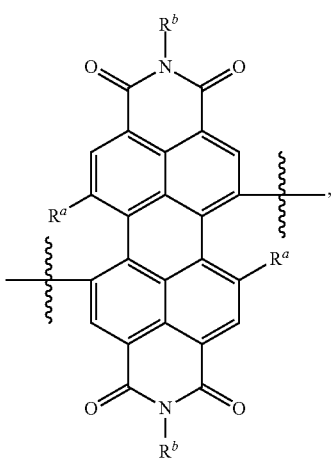
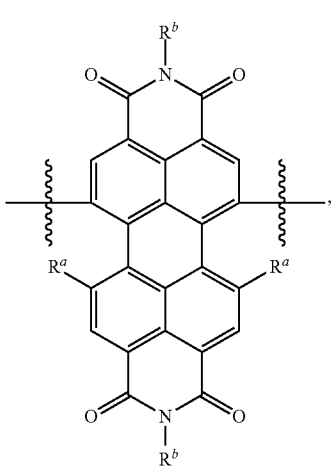
106
-continued
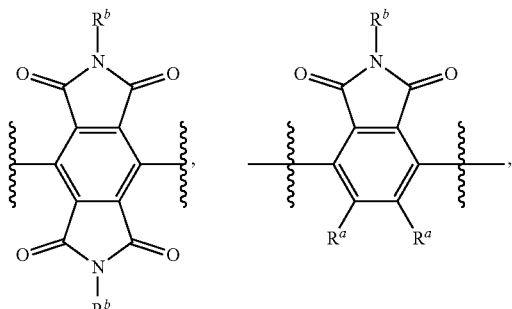
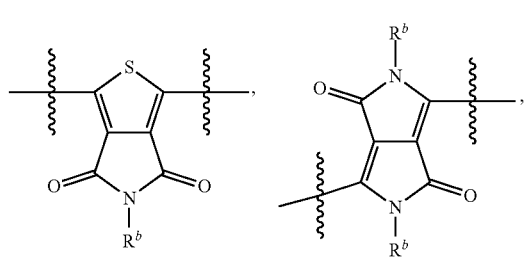
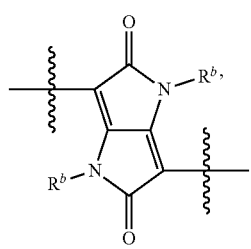
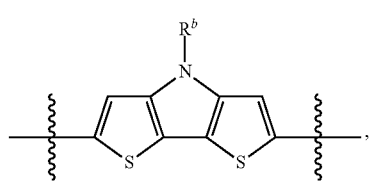
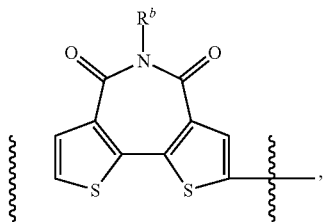
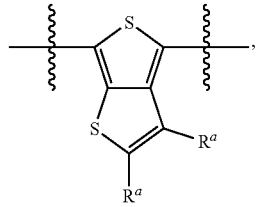
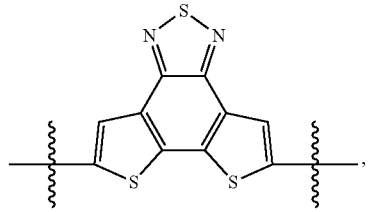

-continued
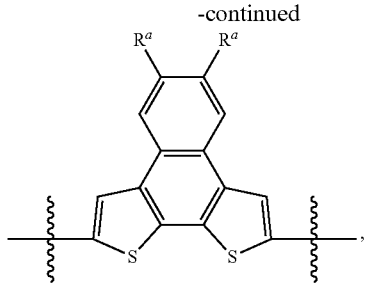
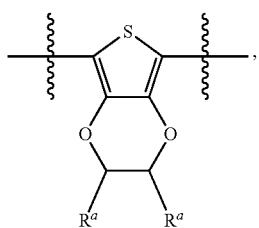
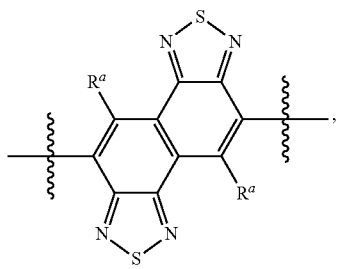
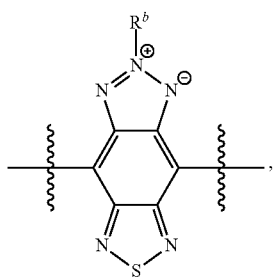
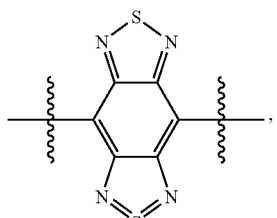
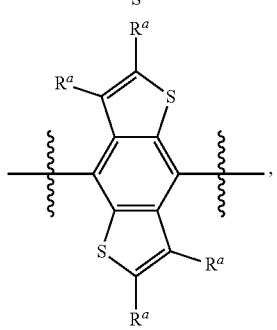
-continued
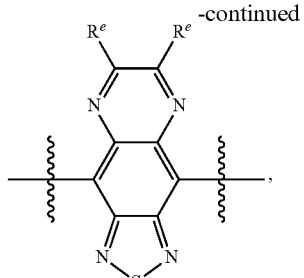
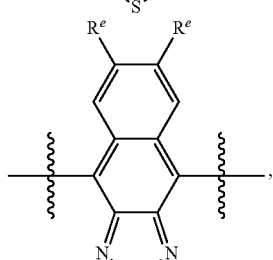
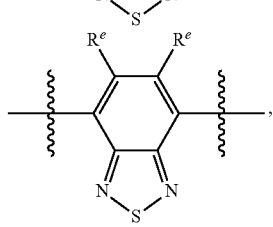
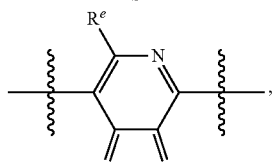
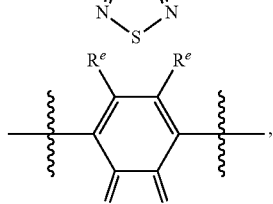
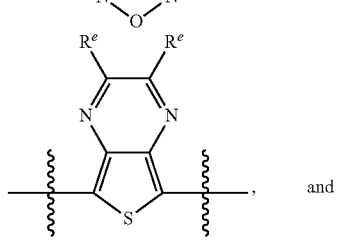
and
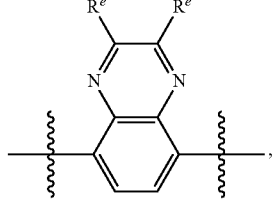
wherein:
$R^a$ is selected from the group consisting of H, F, Cl, —CN, R, —OR, —SR, —C(O)R, —OC(O)R, and —C(O)OR;
$R^b$ is selected from the group consisting of H, R, and -L-$R^f$;

$R^c$ is H or R;

$R^d$ is selected from the group consisting of H, F, Cl, —CN, R, —OR, —SR, —C(O)R, —OC(O)R, —C(O)OR, and -L-$R^f$; and $R^e$ is selected from the group consisting of H, F, Cl, —CN, R, —OR, —SR, —C(O)R, —OC(O)R, —C(O)OR, and $R^f$; wherein $R^f$ is a $C_{6-20}$ aryl group or a 5-20-membered heteroaryl group, each optionally substituted with 1-8 groups independently selected from the group consisting of F, Cl, —CN, R, —OR, and —SR;

L is selected from the group consisting of —O—, —S—, —C(O)—, —OC(O)—, —C(O)O—, and a covalent bond; and R is selected from the group consisting of a $C_{1-40}$ alkyl group, a $C_{1-40}$ haloalkyl group, a $C_{2-40}$ alkenyl group, and a $C_{2-40}$ alkynyl group; and R is selected from the group consisting of a $C_{1-40}$ alkyl group, a $C_{1-40}$ haloalkyl group, a $C_{2-40}$ alkenyl group, and a $C_{2-40}$ alkynyl group.

11. The organic thin film transistor of claim 10, wherein $M_1$ is selected from the group consisting of:

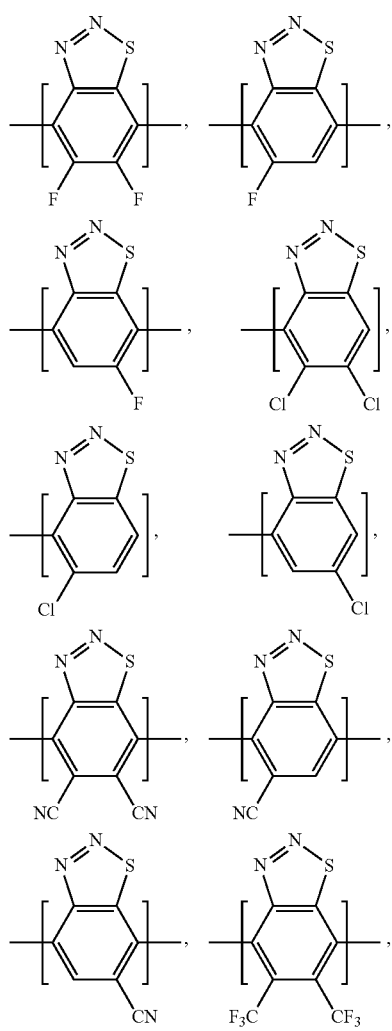

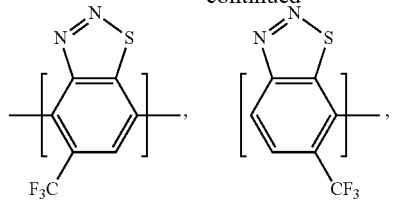

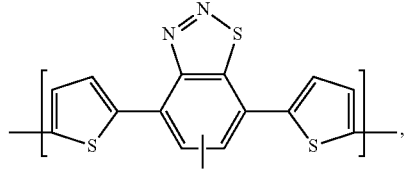

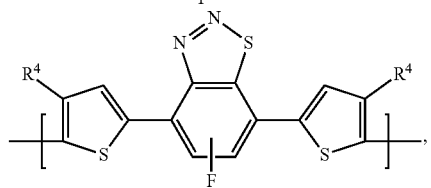

wherein
$R^4$ is selected from $R^2$, $OR^2$, and $SR^2$, where $R^2$ is a linear or branched $C_{1-40}$ alkyl or haloalkyl group; and
$M_2$ is selected from the group consisting of:

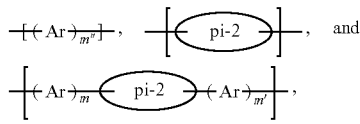

wherein $(Ar)_m$ and $(Ar)_{m'}$ are selected from the group consisting of:

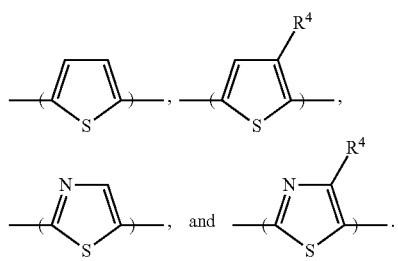

12. The organic thin film transistor of claim 11, wherein the compound is a copolymer having a formula selected from the group consisting of:

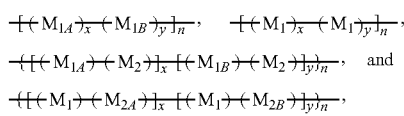

wherein $M_{1A}$ and $M_{1B}$ represent different repeating units $M_1$, and $M_{2A}$ and $M_{2B}$ represent different repeating units $M_2$, x and y are real numbers representing molar ratios, and n is the degree of polymerization.

13. The organic thin film transistor of claim 12, wherein the compound is a random copolymer.

14. The organic thin film transistor of claim 1, wherein $M_1$ is selected from the group consisting of:
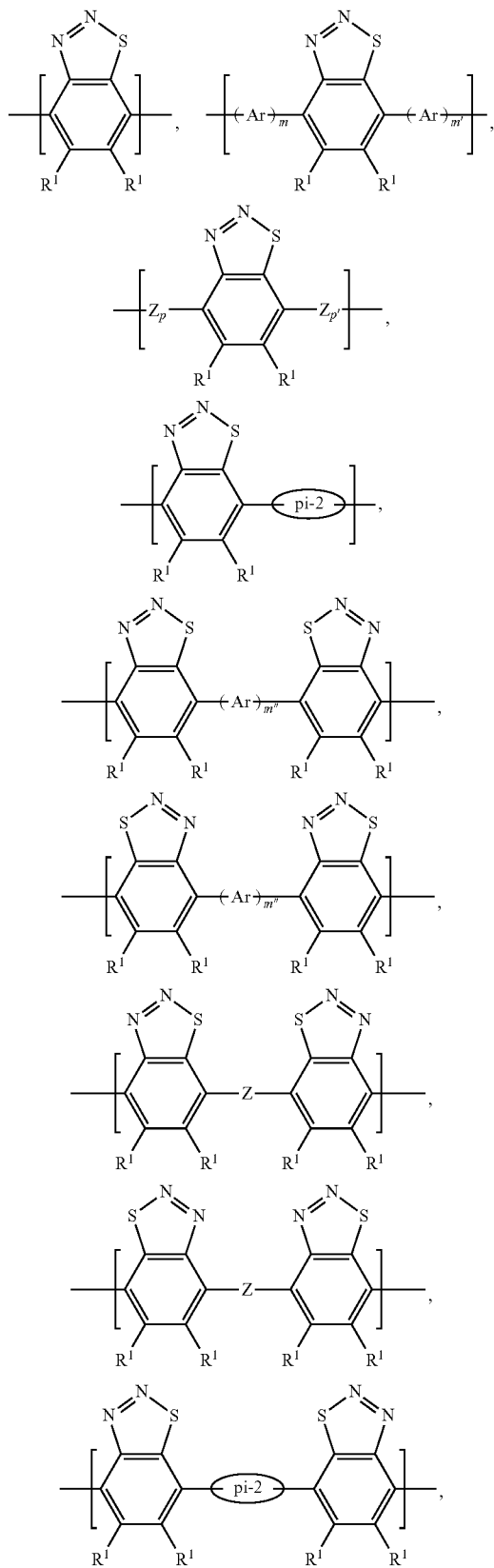
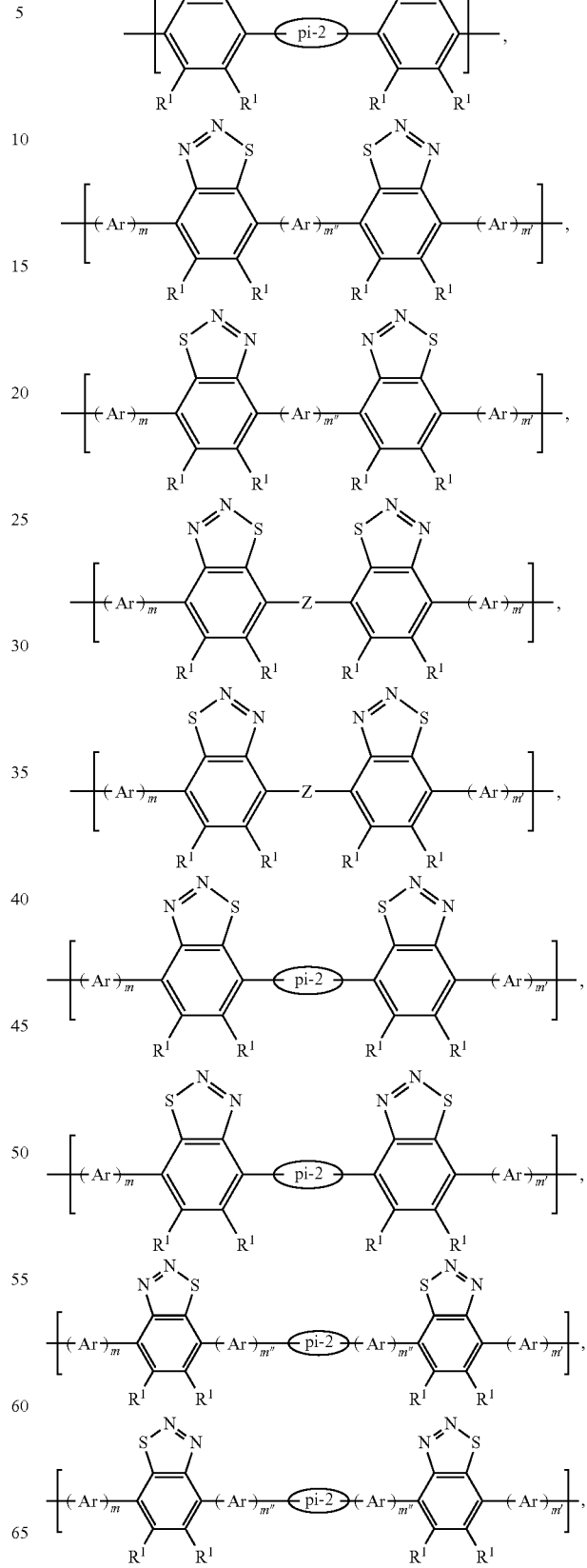

113
-continued
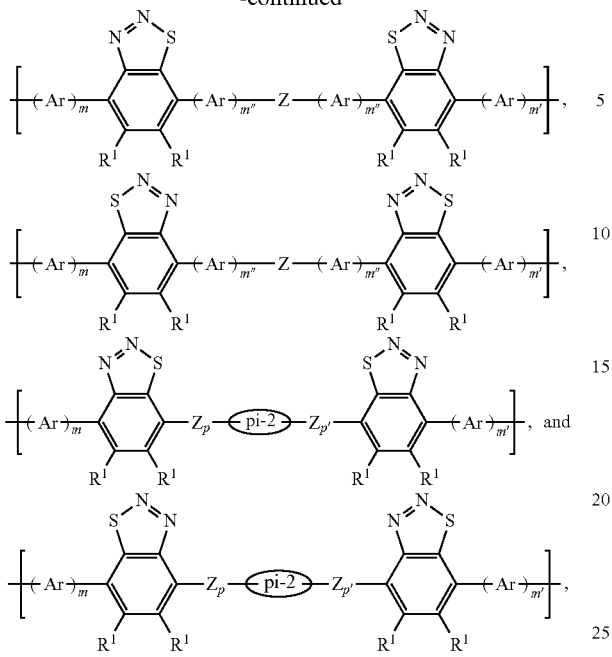
wherein:
pi-2 is selected from the group consisting of:
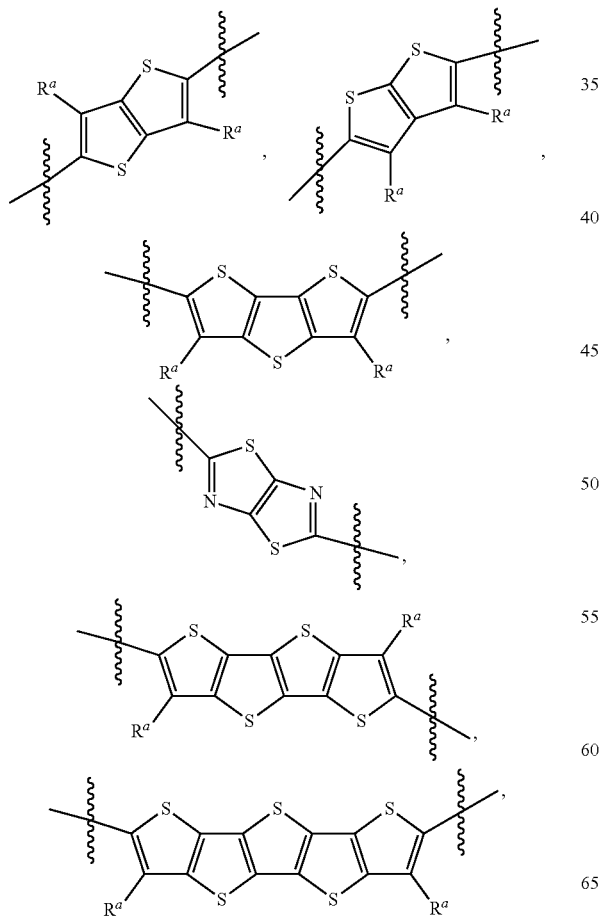
114
-continued
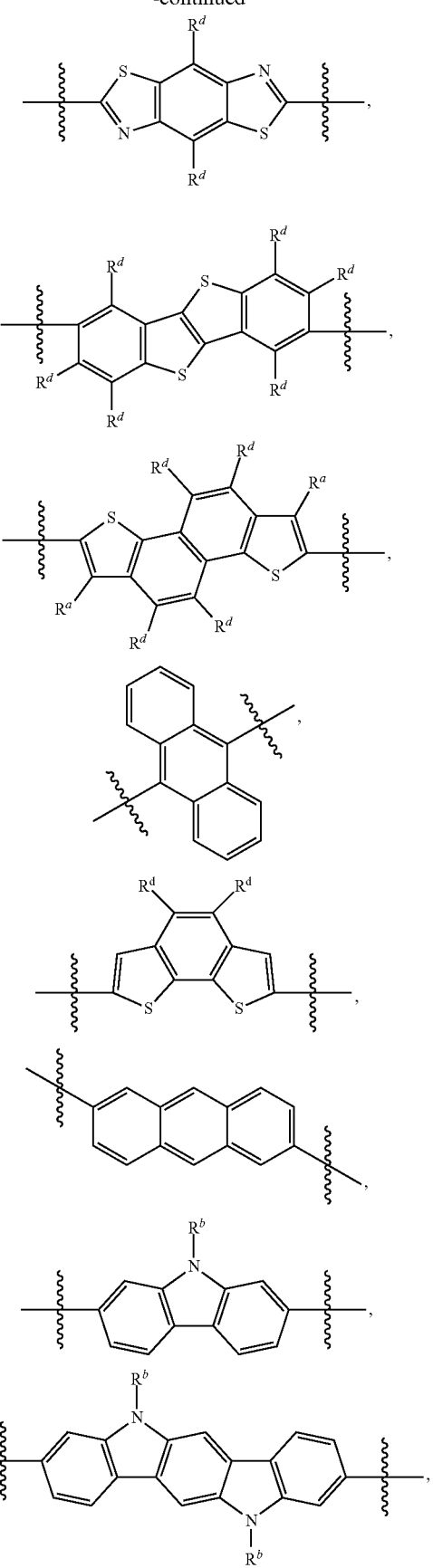

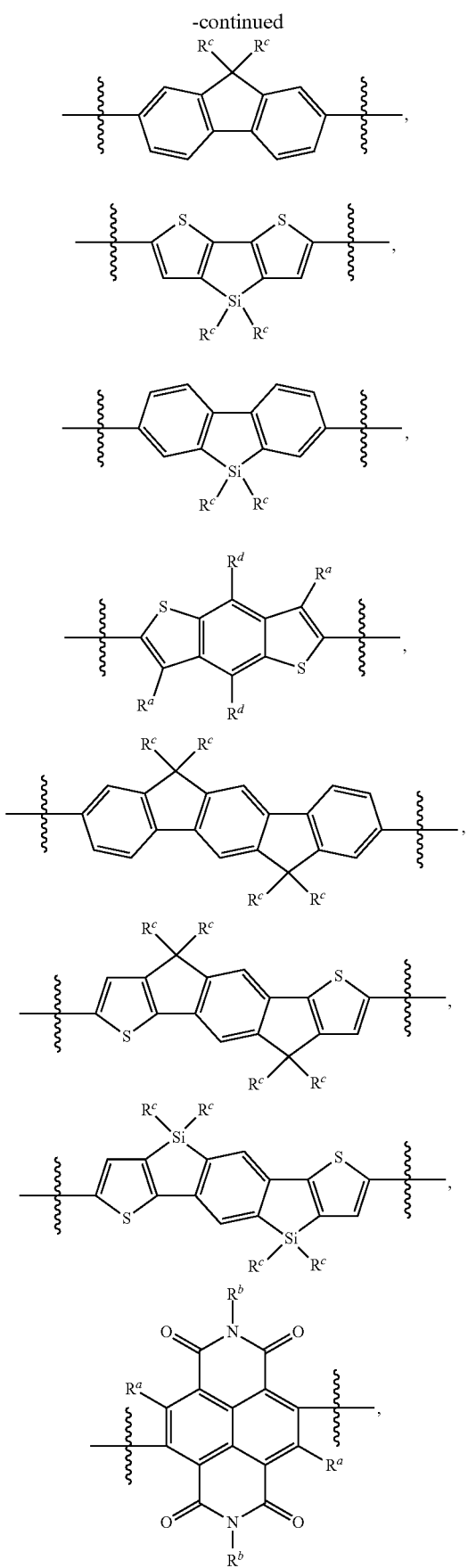
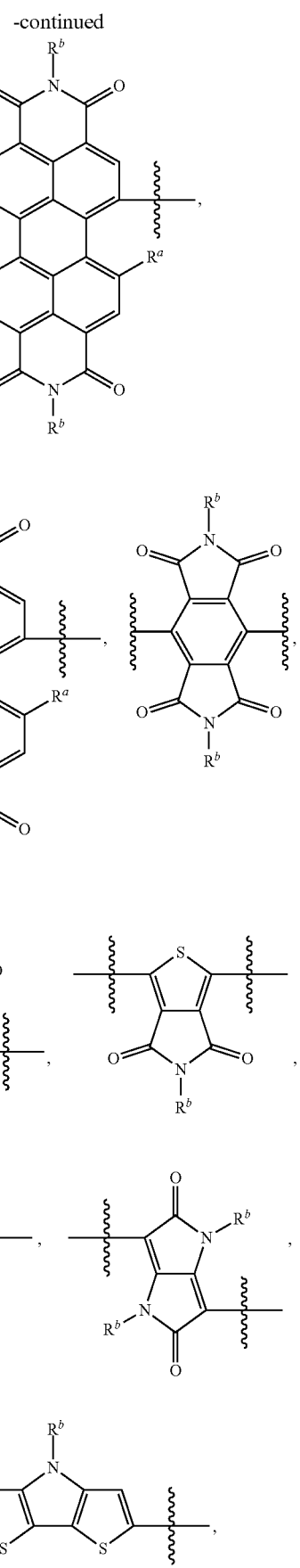

-continued

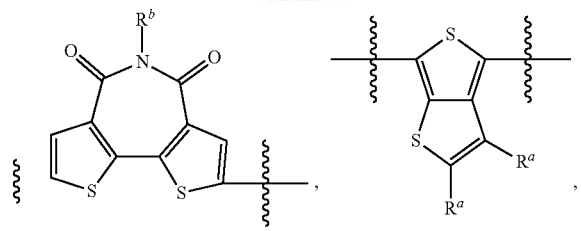

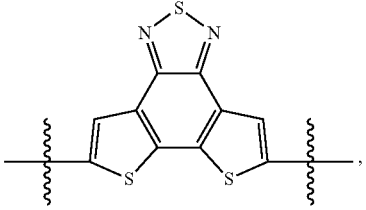

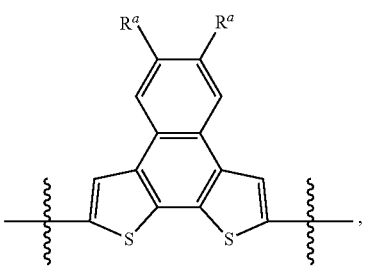

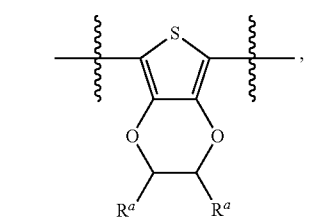

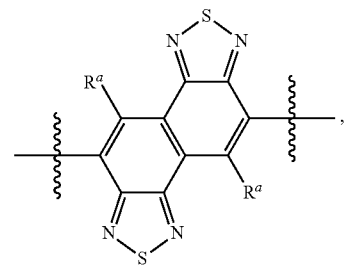

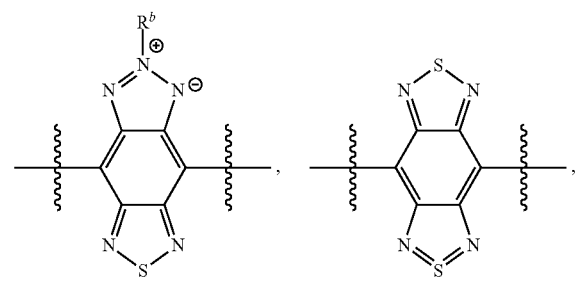

-continued

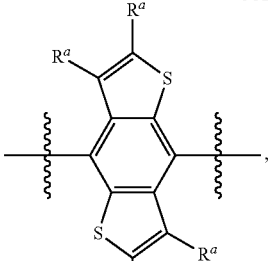

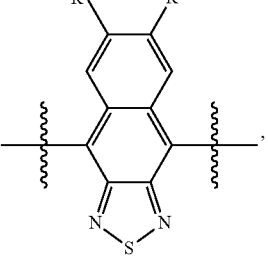

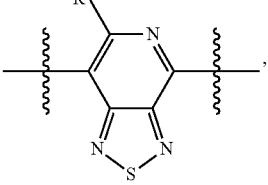

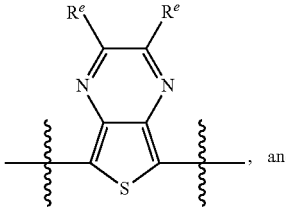

, and wherein:
$R^a$ is selected from the group consisting of H, F, Cl, —CN, R, —OR, —SR, —C(O)R, —OC(O)R, and —C(O)OR;
$R^b$ is selected from the group consisting of H, R, and -L-$R^f$;
$R^c$ is H or R;
$R^d$ is selected from the group consisting of H, F, Cl, —CN, R, —OR, —SR, —C(O)R, —OC(O)R, —C(O)OR, and -L-$R^f$;
$R^e$ is selected from the group consisting of H, F, Cl, —CN, R, —OR, —SR, —C(O)R, —OC(O)R, —C(O)OR, and $R^f$;
$R^f$ is a $C_{6-20}$ aryl group or a 5-20-membered heteroaryl group, each optionally substituted with 1-8 groups independently selected from the group consisting of F, Cl, —CN, R, —OR, and —SR;
L is selected from the group consisting of —O—, —S—, —C(O)—, —OC(O)—, —C(O)O—, and a covalent bond; and
R is selected from the group consisting of a $C_{1-40}$ alkyl group, a $C_{1-40}$ haloalkyl group, a $C_{2-40}$ alkenyl group, and a $C_{2-40}$ alkynyl group;
Ar, at each occurrence, is independently a 5- or 6-membered aryl or heteroaryl group each optionally substituted with 1-4 $R^5$ groups independently selected from a halogen, CN, a $C_{1-40}$ alkyl group, a $C_{1-40}$ haloalkyl group, a $C_{1-40}$ alkoxy group, and a $C_{1-40}$ alkylthio group;

Z is a conjugated noncyclic linker;

m and m' independently are 0, 1, 2, 3, 4, 5 or 6, provided that at least one of m and m' is not 0;

m" is 1, 2, 3, 4, 5 or 6; and p and p' independently are 0 and 1, provided that at least one of p and p' is 1.

15. The organic thin film transistor of claim 14, wherein $M_1$ is selected from:

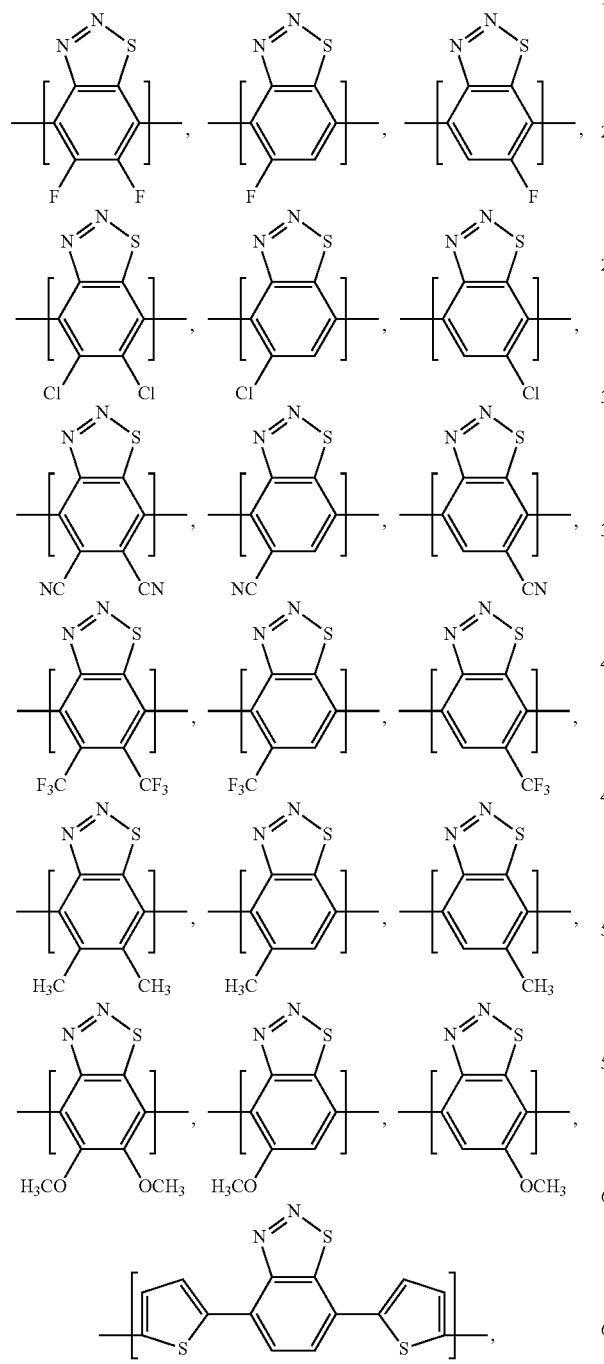

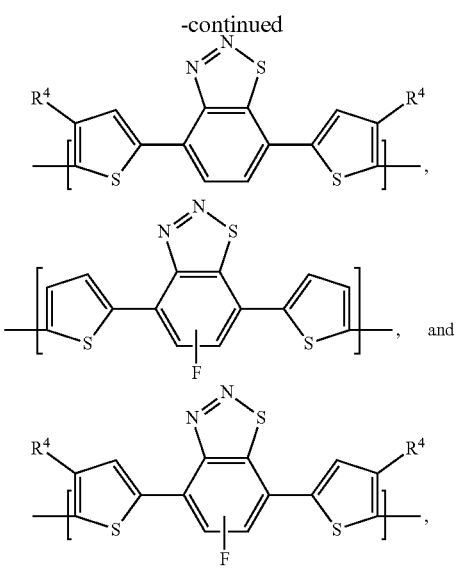

wherein $R^4$ is selected from $R^2$, $OR^2$, and $SR^2$, where $R^2$ is a linear or branched $C_{1-40}$ alkyl or haloalkyl group.

16. The organic thin film transistor of claim 14, wherein the polymer is a homopolymer of a single repeating unit $M_1$ or copolymer only of two or more different repeating units $M_1$.

17. The organic thin film transistor of claim 14, wherein the polymer further comprises one or more repeating units other than $M_1$, the one or more other repeating units ($M_2$) being selected from the group consisting of:

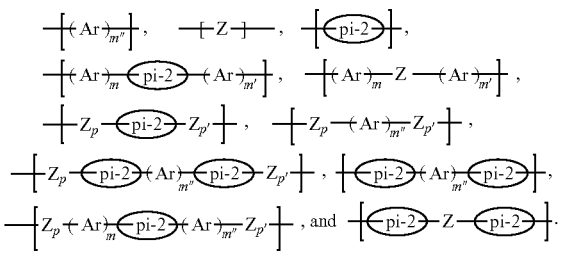

18. The organic thin film transistor of claim 14, wherein the one or more other repeating units ($M_2$) have the formula

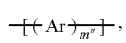

wherein m" is selected from 1, 2, 3, or 4, and wherein each Ar of $(Ar)_{m''}$ is represented by:

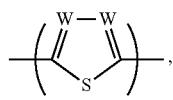

wherein each W independently is selected from the group consisting of N, CH, and $CR^4$, wherein $R^4$ is selected from the group consisting of F, Cl, —CN, $R^2$, $OR^2$, $SR^2$, $C(O)R^2$, $OC(O)R^2$, and $C(O)OR^2$, and wherein $R^2$ is selected from the group consisting of a $C_{1-40}$ alkyl group, a $C_{2-40}$ alkenyl group, a $C_{2-40}$ alkynyl group, and a $C_{1-40}$ haloalkyl group.

19. An organic photovoltaic device comprising an anode, a cathode, optionally one or more anode interlayers, optionally one or more cathode interlayers, and in between the anode and the cathode a semiconductor component comprising a blend material, the blend material comprising an electron-acceptor compound and an electron-donor compound, wherein the electron-acceptor compound is a fullerene compound or an electron-transporting polymer, and wherein the electron-donor compound is a polymer having a first repeating unit $M_1$, said polymer having a degree of polymerization (n) ranging from 3 to 1,000, wherein $M_1$ comprises one or more divalent benzo[d][1,2,3]thiadiazole units represented by formula (I):

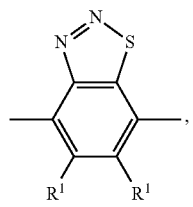

(I)

wherein each $R^1$ independently is selected from the group consisting of H, F, Cl, Br, I, —CN, —NO$_2$, CH$_3$, OCH$_3$, CF$_3$, and a phenyl group, provided at least one $R^1$ is selected from F, Cl, Br, I, —CN, —NO$_2$, and CF$_3$.

20. The organic photovoltaic device of claim 19, wherein $M_1$ is selected from the group consisting of:

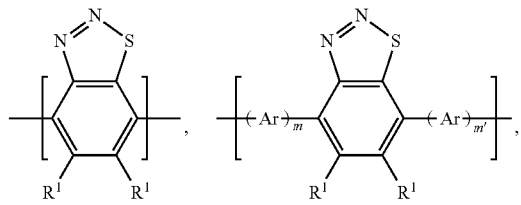

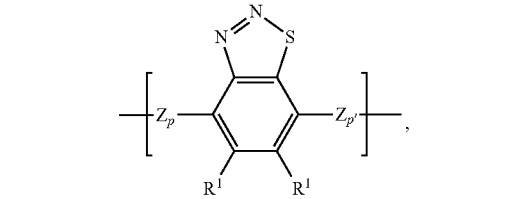

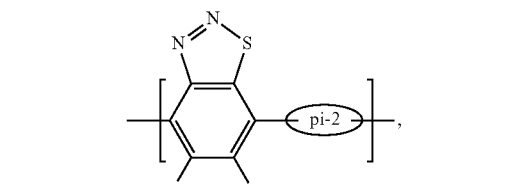

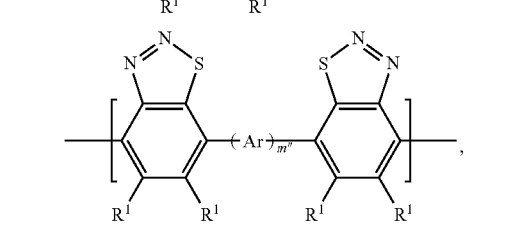

-continued

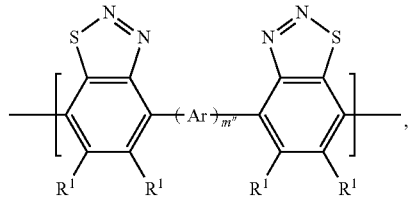

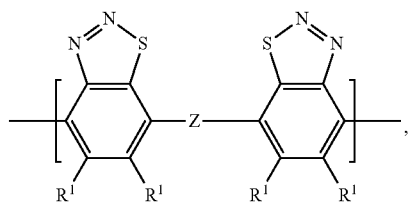

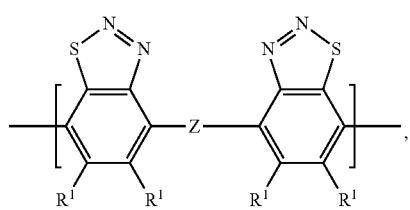

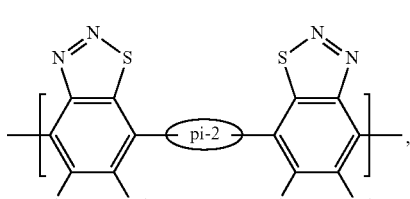

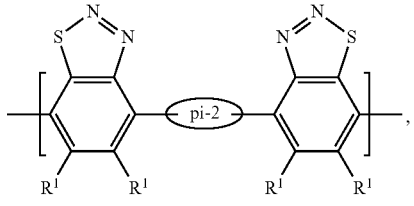

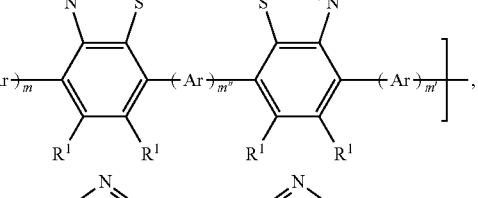

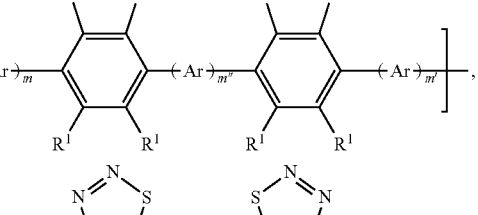

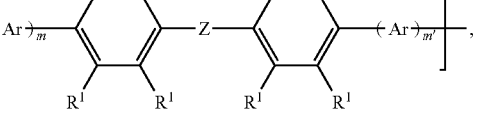

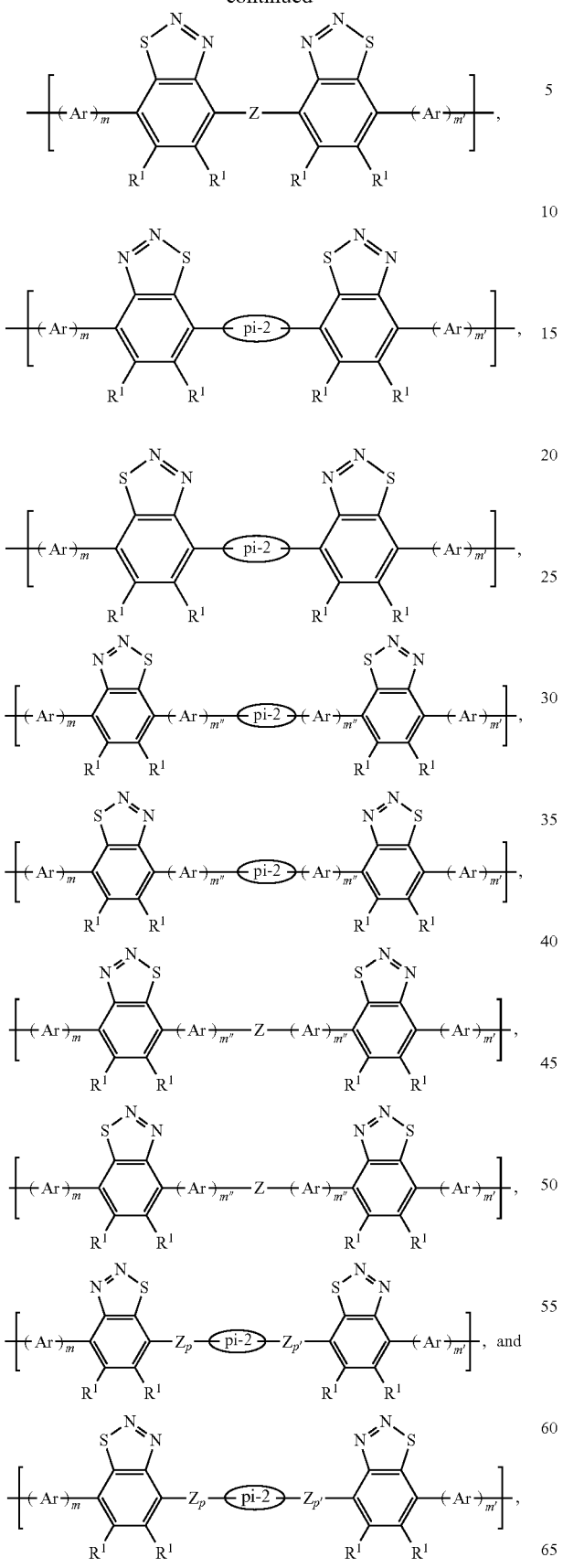
wherein:
pi-2 is selected from the group consisting of:
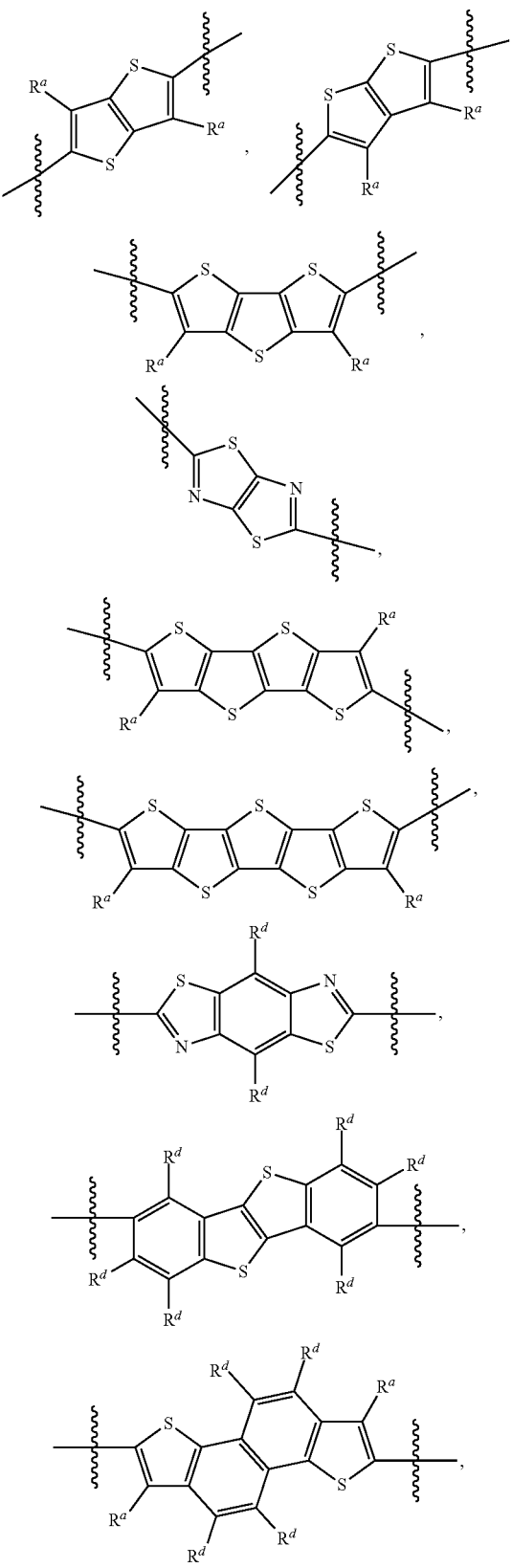

125
-continued
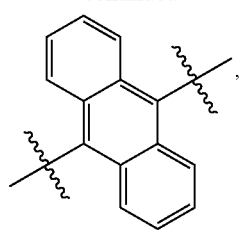
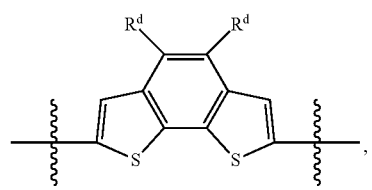
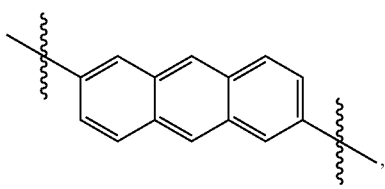
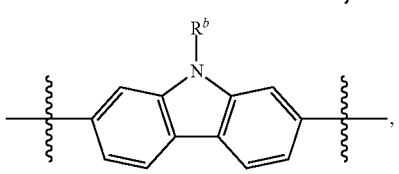
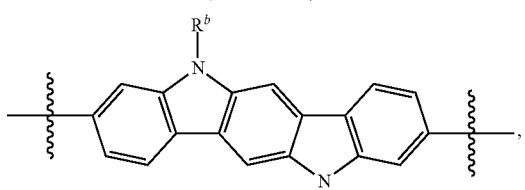
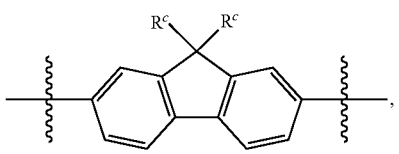
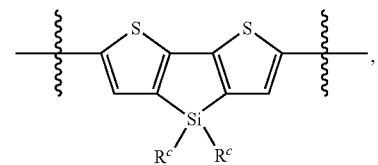
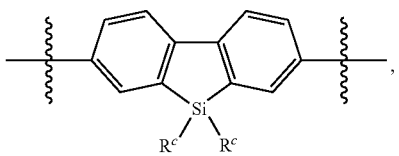
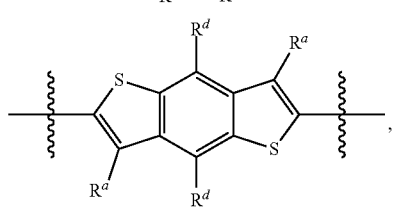
126
-continued
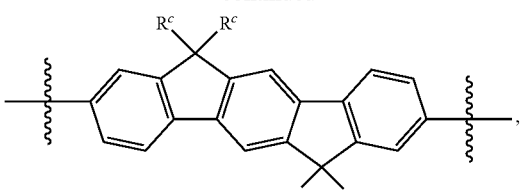
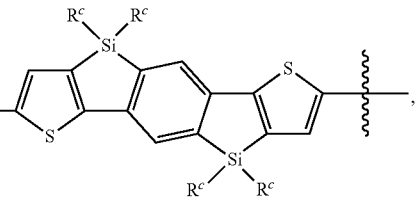
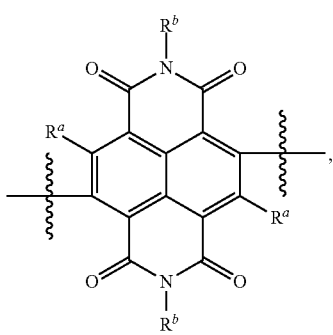
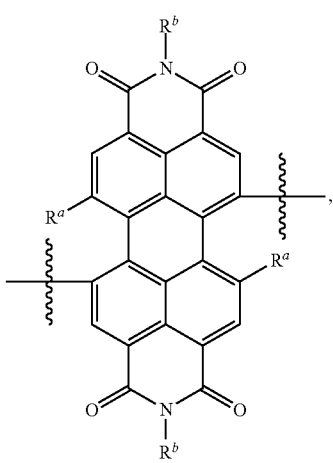

127
-continued
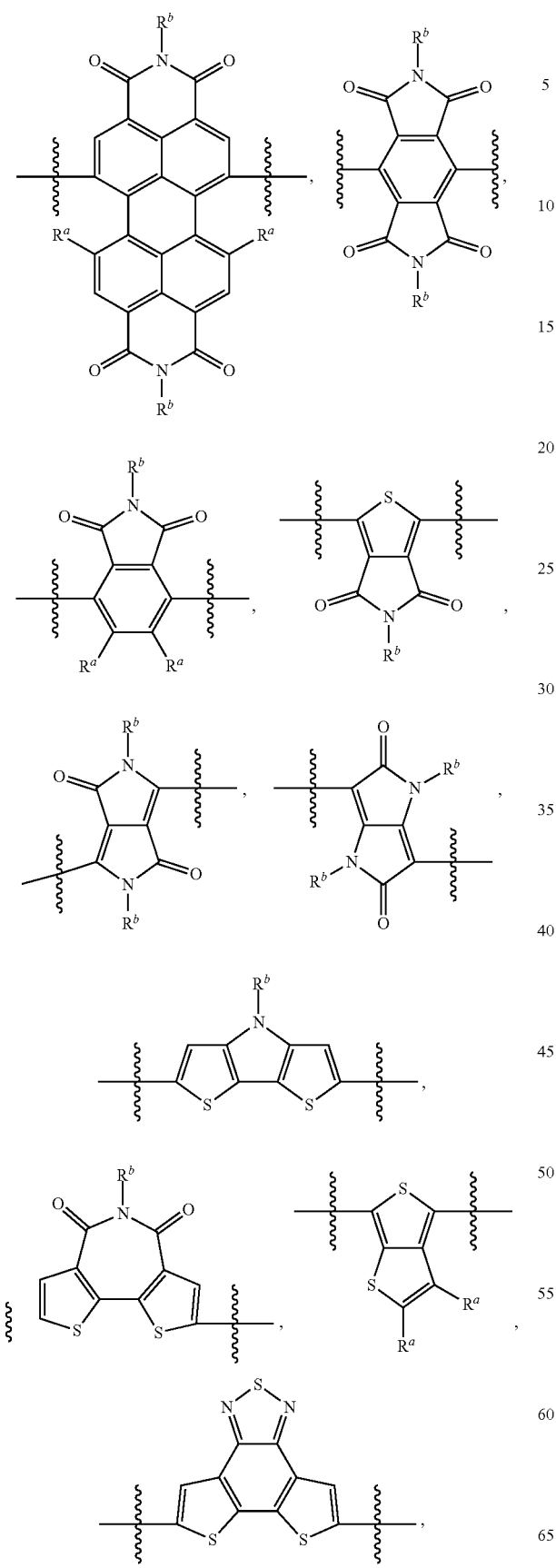
128
-continued
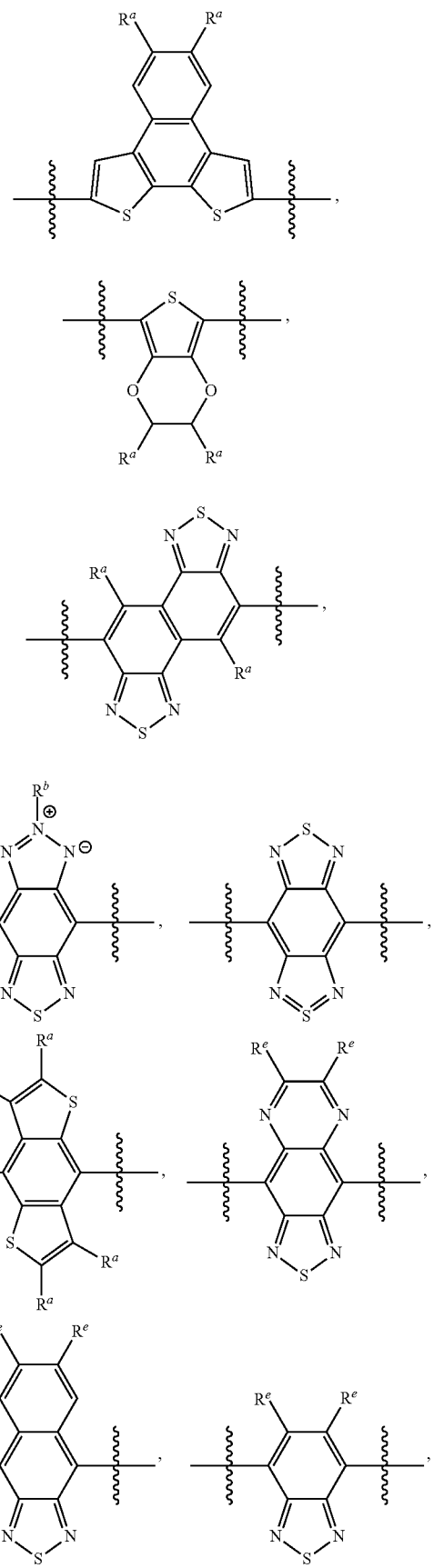

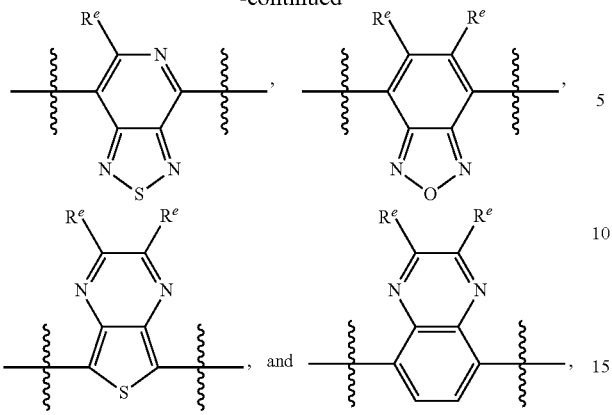

wherein:
- $R^a$ is selected from the group consisting of H, F, Cl, —CN, R, —OR, —SR, —C(O)R, —OC(O)R, and —C(O)OR;
- $R^b$ is selected from the group consisting of H, R, and -L-$R^f$;
- $R^c$ is H or R;
- $R^d$ is selected from the group consisting of H, F, Cl, —CN, R, —OR, —SR, —C(O)R, —OC(O)R, —C(O)OR, and -L-$R^f$;
- $R^e$ is selected from the group consisting of H, F, Cl, —CN, R, —OR, —SR, —C(O)R, —OC(O)R, —C(O)OR, and $R^f$;
- $R^f$ is a $C_{6-20}$ aryl group or a 5-20-membered heteroaryl group, each optionally substituted with 1-8 groups independently selected from the group consisting of F, Cl, —CN, R, —OR, and —SR;
- L is selected from the group consisting of —O—, —S—, —C(O)—, —OC(O)—, —C(O)O—, and a covalent bond; and
- R is selected from the group consisting of a $C_{1-40}$ alkyl group, a $C_{1-40}$ haloalkyl group, a $C_{2-40}$ alkenyl group, and a $C_{2-40}$ alkynyl group;

Ar, at each occurrence, is independently a 5- or 6-membered aryl or heteroaryl group each optionally substituted with 1-4 $R^5$ groups independently selected from a halogen, CN, a $C_{1-40}$ alkyl group, a $C_{1-40}$ haloalkyl group, a $C_{1-40}$ alkoxy group, and a $C_{1-40}$ alkylthio group;

Z is a conjugated noncyclic linker;

m and m' independently are 0, 1, 2, 3, 4, 5 or 6, provided that at least one of m and m' is not 0;

m" is 1, 2, 3, 4, 5 or 6; and p and p' independently are 0 and 1, provided that at least one of p and p' is 1.

* * * * *